(12) United States Patent
Apicella et al.

(10) Patent No.: US 7,250,172 B2
(45) Date of Patent: Jul. 31, 2007

(54) VACCINE AND COMPOSITIONS FOR THE PREVENTION AND TREATMENT OF NEISSERIAL INFECTIONS

(75) Inventors: Michael A. Apicella, Solon, IA (US); Jennifer L. Edwards, Iowa City, IA (US); Bradford W. Gibson, Berkeley, CA (US); Karoline Scheffler, Munich (DE)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/066,551

(22) Filed: Jan. 31, 2002

(65) Prior Publication Data

US 2003/0100071 A1    May 29, 2003

Related U.S. Application Data

(60) Provisional application No. 60/344,452, filed on Oct. 23, 2001, provisional application No. 60/310,356, filed on Aug. 6, 2001, provisional application No. 60/266,070, filed on Jan. 31, 2001.

(51) Int. Cl.
*A61K 39/095* (2006.01)
*A61K 30/02* (2006.01)
*C12P 21/04* (2006.01)
*C07H 21/04* (2006.01)
*C07K 1/00* (2006.01)

(52) U.S. Cl. .............. 424/249.1; 424/190.1; 435/69.7; 536/23.7; 530/350; 530/300

(58) Field of Classification Search ............. 424/184.1, 424/185.1, 190.1, 249.1, 250.1; 530/300, 530/350; 536/23.1, 23.7, 26.1, 26.32; 435/69.1, 435/69.3, 243, 252.3, 69.7
See application file for complete search history.

(56) References Cited

U.S. PATENT DOCUMENTS

| 4,533,630 A | 8/1985 | Wilkins et al. |
|---|---|---|
| 4,554,101 A | 11/1985 | Hopp |
| 4,559,157 A | 12/1985 | Smith et al. |
| 4,608,392 A | 8/1986 | Jacquet et al. |
| 4,820,508 A | 4/1989 | Wortzman |
| 4,873,192 A | 10/1989 | Kunkel |
| 4,938,949 A | 7/1990 | Borch et al. |
| 4,992,478 A | 2/1991 | Geria |
| 2004/0253222 A1 | 12/2004 | Apicella et al. |

FOREIGN PATENT DOCUMENTS

| EP | 0 184 187 | 6/1986 |
|---|---|---|
| WO | WO-98/02547 | 1/1998 |
| WO | WO-99/24578 | 5/1999 |
| WO | WO-99/57280 | 11/1999 |
| WO | WO-00/71725 | 11/2000 |

OTHER PUBLICATIONS

Paz et al 1995, Microbiology 141, 913-920.*
Accession-No. AAY 75751.*
Accession No. B81859.*
Cann et al 1989, J.Med.Microbiology 30, 23-30.*
Barritt et al, Infection and Immunity 1987, 55:2026-2031.*
Caron, Emmanuelle, et al., "Identification of Two Distinct Mechanisms of Phagocytosis Controlled by Different Pho GTPases", *Science*, vol. 282, (Nov. 27, 1998),1717-1721.
Christodoulides, Myron, et al., "Interaction of primary human endometrial cells with *Neisseria gonorrhoeae* expressing green flourescent protein", *Molecular Microbiology*, vol. 35, (2000),32-43.
Cooper, Neil, "Complement evasion strategies of microorganisms", *Immunology Today*, vol. 12, No. 9, (1991),327-331.
De La Paz, Helen, et al., "Effect of sialyation of lipopolysaccharide of *Neisseria gonorrhoeae* on recognition and complement-mediated killing by monoclonal antibodies directed against different outermembrane antigens", *Microbiology*, vol. 141, No. 4, (Apr. 1995),913-920.
Densen, Peter, et al.,"Dissemination of Gonococcal Infection is Associated with Delayed Stimulation of Complement-Dependent Neutrophil Chemotaxis In Vitro", *Infection and Immunity*, vol. 38, No. 2, (Nov. 1982),563-572.
Densen, Peter, "Interaction of Complement with *Neisseria meningitidis* and *Neisseria gonorrhoeae*", *Clinical Microbiology Reviews*, vol. 2, (Apr. 1989),S11-S17.
Edwards, J.L., et al., "*Neiserria gonorrhoeae* Elicits Membrane Ruffling and Cytoskeletal Rearrangements upon Infection of Primary Human Endocervical and Ectocervical Cells", *Infection and Immunity*, 68, (2000),5354-5363.
Frank, Michael, et al., "Complement Interactions and Functions, The role of complement in inflammation and phagocytosis", *Immunology Today*, vol. 12, No. 9, (1991),322-326.
Harvey, Hillery, et al., "Ultrastructural Analysis of Primary Human Urethral Epithelial Cell Cultures Infected with *Neisseria gonorrhoeae*", *Infection and Immunity*, vol. 65, No. 6, (Jun. 1997),2420-2427.
Hayashi, Tomoko, et al., "Binding of the 68-Kilodalton Protein of *Mycobacterium avium* to $\alpha_v\beta_3$ on Human Monocyte-Derived Macrophages Enhances Complement Receptor Type 3 Expression", *Infection and Immunity*, vol. 65, No. 4, (Apr. 1997),1211-1216.
Hussain, L.A., et al.,"Investigation of the complement receptor 3 (CD11b/CD18) in human rectal epithelium", *Clinical and Experimental Immunology*, vol. 102, (1995),384-388.
Hynes, Richard,"Integrins: A Family of Cell Surface Receptors", *Cell*, vol. 48, No. 4, (Feb. 27, 1987), 549-554.
Ingalls, Robin, et al.,"The CD11/CD18 Integrins: Characterization of Three Novel LPS Signling Receptors", *Prog. Clin. Biol. Res.*, vol. 397, (1998),107-117.

(Continued)

*Primary Examiner*—Susan Ungar
*Assistant Examiner*—Padma Baskar
(74) *Attorney, Agent, or Firm*—Viksnins Harris & Padys PLLP

(57) ABSTRACT

The present invention is directed to novel polypeptides, polynucleotides and vaccines for use against *Neisseria gonorrhoeae* colonization or infection. The vaccines contain an immunogenic amount of a neisserial protein.

Figure 1:
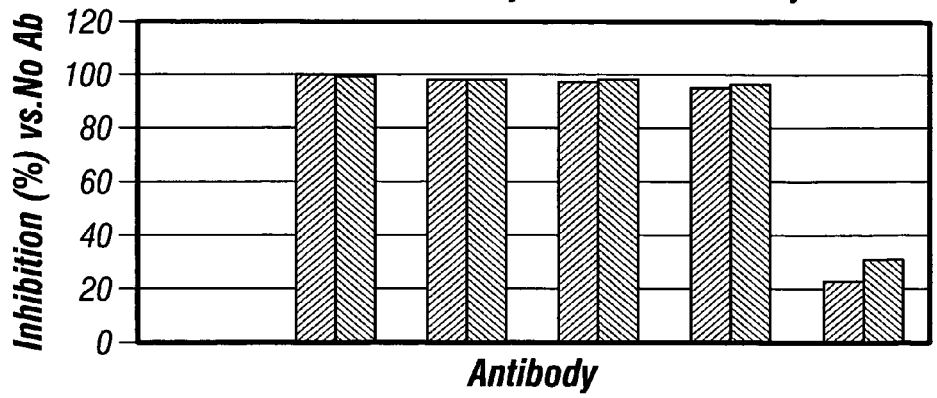

18 Claims, 9 Drawing Sheets
(7 of 9 Drawing Sheet(s) Filed in Color)

OTHER PUBLICATIONS

Jarvis, Gary, et al. ,"Invasion of Human Mucosal Epithelial Cells by *Neisseria gonorrhoeae* Upregulates Expression on Intercellular Adhesion Molecule 1 (ICAM-1)", *Infection and Immunity*, vol. 67, No. 3, (Mar. 1999),1149-1156.

Jerse, Ann, et al. ,"Adhesion and invasion by the pathogenic neisseria", *Trends in Microbiology*, vol. 5, No. 6, (Jun. 1997),217-221.

Jones, J.L.,et al. ,"Integrins: a role as cell signalling molecules", *Journal of Clinical Pathology: Molecular Pathology*, vol. 52, (1999),208-213.

Jones, Samuel, et al. ,"Two Signaling Mechanisms for Activation of $\alpha_M\beta_2$ Avidity in Polymorphonuclear Neutrophils", *Journal of Biological Chemistry*, vol. 273, No. 17, (Apr. 24, 1998),10556-10566.

Kishimoto, Takashi, et al. ,"The Leukocyte Integrins", *Advances in Immunology*, vol. 46, (1989),149-182.

Kragsbjerg, P., et al. ,"The effects of live *Neisseria menigitidis* and tumour necrosis factor-$\alpha$ on neutrophil oxidative burst and $\beta$2-integrin expression", *APMIS*, vol. 108, (2000),276-282.

Mcquillen, Daniel, et al. ,"Complement Processing and Immunoglobulin Binding to *Neisseria gonorrhoeae* Determined In Vitro Simulates In Vivo Effects", *The Journal of Infectious Diseases*, vol. 179, No. 1, (Jan. 1999), 124-135.

Mesri, Mehdi, et al. ,"Dual regulation of Ligand Binding by CD11b I Domain", *The Journal of Biological Chemistry*, vol. 273, No. 2, (Jan. 9, 1998),744-748.

Meyer, Thomas,"Pathogenic Neisseriae: Complexity of Pathogen—Host Cell Interplay", *Clinical Infectious Diseases*, vol. 28, No. 3, (Mar. 1999),433-441.

Mosser, David, et al. ,"The third component of complement (C3) is responsible for the intracellular survival of *Leishmania major"*, *Nature*, vol. 327, No. 6210, (May 28, 1987),329-331.

Nassif, Xavier, et al. ,"Interaction of Pathogenic Neisseriae with Nonphagocyctic Cells", *Clinical Microbiology Reviews*, (Jul. 1995),376-388.

Nassif, Xavier, et al. ,"Interactions of Pathogenic Neisseria with host cells. Is it possible to assemble the puzzle?", *Molecular Microbiology*, vol. 32, No. 6, (Jun. 1999),1124-1132.

Naumann, Michael, et al. ,"Host cell interactions and Signalling with *Neisseria gonorrhoeae"*, *Curr. Opin. Microbiol.*, vol. 2, (1999),62-70.

Ram, Sanjay, et al. ,"A Novel Sialic Acid Binding Site on Factor H Mediates Serum Resistance of Sialylated *Neisseria gonorrhoeae"*, *Journal of Experimental Medicine*, vol. 187, No. 5, (Mar. 2, 1998),743-752.

Ram, S., et al. ,"The contrasting mechanisms of serum resistance of *Neisseria gonorrhoeae* and group B *Neisseria meningitidis"*, *Molecular Immunology*, vol. 36, No. 13-14, (1999),915-928.

Van Kooyk, Yvette, et al. ,"The Actin Cytoskeleton Regulates LFA-1 Ligand Binding through Avidity Rather than Affinity Changes", *The Journal of Biological Chemistry*, vol. 274, No. 38, (Sep. 17, 1999),26869-26877.

Vogel, Ulrich, et al. ,"Mechanism of neisserial serum resistance", *Molecular Microbiology*, vol. 32, No. 6, (Jun. 1999),1133-1139.

Wurzner, Reinhard, "Evasion of pathogens by avoiding recognition or eradication by complement, in a part via molecular mimicry", *Molecular Immunology*, vol. 36, (1999),249-260.

Edwards, J..L. , et al. ,"Complement Receptor Type 3 (CR3) on Primary Cervical Epithelial Cells Serves as a Receptor for *Neisseria Gonorrhoeae"*, *Abstracts of the 101st General Meeting of the American Society for Microbiology*, Orlando, FL,(May 20-24, 2001),p. 303.

Krishnan Thankavel et al., "Localization of a Domain in the FimH Adhesin of *Escherichia coli* Type 1 Fimbriae Capable of Receptor Recognition and Use of a Domain-specific antibody to Confer Protection against Experimental Urinary Tract Infection", *J. Clin. Invest.*, vol. 100, No. 5, Sep. 1997, pp. 1123-1136.

P. M. Steed et al., "Intracellular Signaling by Phospholipase D as A Therapeutic Target", *Current Pharmaceutical Biotechnology*, 2001, vol. 2, 241-256.

Edwards, J. L., et al., "The Role of Complement Receptor 3 (CR3) in *Neisseria gonorrhoeae* Infection of Human Cervical Epithelia", *Cellular Microbiology*, 3, (Sep. 2001), 611-622.

Fijen, C. A., et al., "The Role of Fc-gamma Receptor Polymorphisms and C3 in the Immune Defence Against *Neisseria meningitidis* in Complement-Deficient Individuals", *Clinical and Experimental Immunology*, 120, (May 2000), 338-345.

Cohen et al., Human Experimentation with *Neisseria gonorrhoeae*: Progress and Goals, J. Infect. Dis. 1999; 179(Suppl. 2):S375-9.

Accession No. AAY75753.

Accession No. AL162756.

Accession No. ABP79466.

Accession No. AAZ54515.

Accession No. ABZ40436.

International Search Report for International Application Serial No. PCT/US02/02881, (2004).

International Search Report for International Application Serial No. PCT/US2004/022708, (2004).

Alpuche-Aranda et al., "*Salmonella* Stimulate Macrophage Macropinocytosis and Persist within Spacious Phagosomes," *J. Exp. Med.*, 1994, 179:601-608.

Altieri, "Occupancy of CD11b/Cd18 (Mac-1) Divalent Ion Binding Site(s) Induces Leukocyte Adhesion," *J. Immunol.*, 1991, 147:1891-1898.

Altschul et al., "Basic Local Alignment Search Tool," *J. Mol. Biol.*, 1990, 215:403-410.

Altschul et al., "Gapped BLAST and PSI-BLAST: a new generation of protein database search programs," *Nucl. Acids Res.*, 1997, 25:3389-3402.

Apicella, "Antigenically Distinct Populations of *Neisseria gonorrhoeae*: Isolation and Characterization of the Responsible Determinants," *J. Infect. Dis.*, 1974, 130:619-625.

Batzer et al., "Enhanced evolutionary PCR using oligonucleotides with inosine at the 3'-terminus," *Nucl. Acids. Res.*, 1991, 19:5081.

Becherer et al., "Cell Surface Proteins Reacting with Activated Complement Components," *Complement Inflamm.*, 1989, 6:142-165.

Bessen and Gotschlich, "Interactions of Gonococci with HeLa Cells: Attachment, Detachment, Replication, Penetration, and the Role of Protein II," *Infect. Immun.*, 1986, 54:154-160.

Bjerknes et al., "Neisserial Porins Inhibits Human Neutrophil Actin Polymerization, Degranulation, Opsonin Receptor Expression, and Phagocytosis but Prime the Neutrophils To Increase Their Oxidative Burst," *Infect. Immun.*, 1995, 63:160-167.

Carrea et al., "Purification and Properties of two phospholipases D from *Streptomyces* sp.," *Biochim. Biophys. Acta.*, 1995, 1255:273-279.

Chen et al., "Heparin Protects Opa$^+$ *Neisseria gonorrhoeae* from the Bactericidal Action of Normal Human Serum," *Infect. Immun.*, 1995, 63:1790-1795.

Clarke and Spudich, "Nonmuscle Contractile Proteins: The Role of Actin and Myosin in Cell Motility and Shape Determination," *Ann. Rev. Biochem.*, 1977, 46:797-822.

Clauser et al., "Role of Accurate Mass Measurement ($\pm$10 ppm) in Protein Identification Strategies Employing MS or MS/MS and Database Searching," *Anal. Chem.*, 1999, 71:2871-2882.

Clerc and Sansonetti, "Entry of *Shigella flexneri* into HeLa Cells: Evidence for Directed Phagocytosis Involving Actin Polymerization and Myosin Accumulation," *Infect. Immun.*, 1987, 55:2681-2688.

Cohen et al., "Human Experimentation with *Neisseria gonorrhoeae*: Rationale, Methods, and Implications for the Biology of Infection and Vaccine Development," *J. Infect. Dis.*, 1994, 169:532-537.

Colley et al., "Phospholipase D2, a distinct phospholipase D isoform with novel regulatory properties that provokes cytoskeletal reorganization," *Curr. Biol.*, 1997, 7:191-201.

Corpet, "Multiple sequence alignment with hierarchical clustering," *Nucl. Acids Res.*, 1988, 16:10881-10890.

Dayhoff et al., "A Model of Evolutionary Change in Proteins," *Atlas of Protein Sequence and Structure*, Natl. Biomed. Res. Found., 1978, pp. 345-352.

Dehio et al., "The role of neisserial Opa proteins in interactions with host cells," *Trends Microbiol.*, 1998, 6:489-495.

DiPaolo et al., "Cellular and Molecular Alterations in Human Epithelial Cells Transformed by Recombinant Human Papillomavirus DNA," *Crit. Rev. Oncogen.*, 1993, 4:337-360.

Dramsi and Cossart, "Intracellular Pathogens and the Actin Cytoskeleton," *Annu. Rev. Cell Dev. Biol.*, 1998, 14:137-166.

Draper et al., "Scanning electron microscopy of attachment of *Neisseria gonorrhoeae* colony phenotypes to surfaces of human genital epithelia," *Am. J. Obstet. Gynecol.*, 1980, 138:818-826.

Dudas and Apicella, "Selection and Immunochemical Analysis of Lipoligosaccharide Mutants of *Neisseria gonorrhoeae*,"*Infect. Immun.*, 1988, 56:499-504.

Edwards and Apicella, "The role of lipooligosaccharide in *Neisseria gonorrhoeae* pathogenesis of cervical epithelia: lipid A serves as a C3 acceptor molecule," *Cell. Microbiol.*, 2002, 4:585-598.

Edwards et al., "A co-operative interaction between *Neisseria gonorrhoeae* and complement receptor 3 mediates infection of primary cervical epithelial cells," *Cell. Microbiol.*, 2002, 4:571-584.

Edwards et al., "Gonococcal phospholipase D modulates the expression and function of complement receptor 3 in primary cervical epithelial cells", *Infect Immun*, 71, 6381-6391 (2003).

Edwards et al., "*Neisseria gonorrhoeae* PLD directly interacts with Akt kinase upon infection of primary, human, cervical epithelial cells", *Cell Microbiol.*, 8(8), 1253-1271 (2006).

Elemer and Edgington, "Microfilament Reorganization Is Associated with Functional Activation of $\alpha_M\beta_2$ on Monocytic Cells," *J. Biol. Chem.*, 1994, 269:3159-3166.

Erdei et al., "The role of C3 in the immune response," *Immun. Today*, 1991, 12:332-337.

Evans, "Ultrastructural Study of Cervical Gonorrhea," *J. Infect. Dis.*, 1977, 136(2):248-255.

Exton, "New Developments in Phospholipase D," *J. Biol. Chem.*, 1997, 272:15579-15582.

Fällman et al., "Complement Receptor-mediated Phagocytosis Is Associated with Accumulation of Phosphatidylcholine-derived Diglyceride in Human Neutrophils," *J. Biol. Chem.*, 1992, 267:2656-2663.

Finlay and Falkow, "Common Themes in Microbial Pathogenicity Revisited," *Microbiol. Mo. Biol. Rev.*, 1997, 61:136-169.

Finlay and Ruschkowski, "Cytoskeletal rearrangements accompanying *Salmonella* entry into epithelial cells," *J. Cell. Sci.*, 1991, 99:283-296.

Fluhmann, "The Squamocolumnar Transitional Zone of the Cervix Uteri," *Obstet. Gynecol.*, 1959, 14:133-148.

Francis et al., "Ruffles induced by *Salmonella* and other stimuli direct macropinocytosis of bacteria," *Nature*, 1993, 364:639-642.

Fukami et al., "$\alpha$-Actinin and Vinculin Are $PIP_2$-binding Proteins Involved in Signaling by Tyrosine Kinase," *J. Biol. Chem.*, 1994, 169:1518-1522.

Gazdar et al., "Characterization of Paired Tumor and Non-Tumor Cell Lines Established from Patients with Breast Cancer," *Int. J. Cancer*, 1998, 78:766-774.

Garcia-del Portillo and Finlay, "*Salmonella* Invasion of Nonphagocytic Cells Induces Formation of Macropinosomes in the Host Cell," *Infect. Immun.*, 1994, 62:4641-4645.

Goeddel et al., "Synthesis of human fibroblast interferon by *E. coli*," *Nucl. Acids. Res.*, 1980, 8:4057-4074.

Grassmé et al., "Gonococcal Opacity Protein Promotes Bacterial Entry-Associated Rearrangments of the Epithelial Cell Actin Cytoskeleton," *Infect. Immun.*, 1996, 64(5):1621-1630.

Griffin, Jr. et al., "Studies on the Mechanism of Phagocytosis: The Interaction of Macrophages with Anti-Immunoglobulin IgG-Coated Bone Marrow-Derived Lymphocytes," *J. Exp. Med.*, 1976, 144:788-809.

Griffin, Jr. et al., "Studies on the Mechanism of Phagocytosis: Requirements for Circumferential Atachment of Particle-Bound Ligands to Specific Receptors on the Macrophage Plasma Membrane," *J. Exp. Med.*, 1975, 142:1263-1282.

Ha and Exton, "Activation of Actin Polymerization by Phosphatidic Acid Derived from Phosphatidylcholine in IIC9 Fibroblasts," *J. Cell. Biol.*, 1993, 123:1789-1796.

Harkness, "The Pathology of Gonorrhoea," *Br. J. Vener. Dis.*, 1948, 24:137-147.

Harvey et al., "Receptor-mediated endocytosis of *Neisseria gonorrhoeae* into primary human urethral epithelial cells: the role of the asialoglycoprotein receptor," *Mol. Microbiol.*, 2001, 42:659-672.

Harvey et al., "Immortalization of Human Urethral Epithelial Cells: a Model for the Study of the Pathogenesis of and the Inflammatory Cytokine Response to *Neisseria gonorrhoeae* Infection," *Infect. Immun.*, 2002, 70:5808-5815.

Hauck et al., "CD66-mediated-phagocytosis of $Opa_{52}$ *Neisseria gonorrhoeae* requires a Src-like tyrosine kinase- and Rac1-dependent signaling pathway," *EMBO J.*, 1998, 17:443-454.

Higgins and Sharp, "CLUSTAL: a package for performing multiple sequence alignment on a microcomputer," *Gene*, 1988, 73:237-244.

Higgins and Sharp, "Fast and sensitive multiple sequence alignments on a microcomputer," *CABIOS*, 1989, 5:151-153.

Hildreth and August, "The Human Lymphocyte Function-Associated (HLFA) Antigen and a Related Macrophage Differentiation Antigen (HMac-1): Functional Effects of Subunit-Specific Monoclonal Antibodies," *J. Immunol.*, 1985, 134:3272-3280.

Hinnebusch et al., "Role of Yersinia Murine Toxin in Survival of *Yersinia pestis* in the Midgut of the Flea Vector," *Science*, 2002, 296:733-735.

Hodgson et al., "Rational Attentuation of *Corynebacterium pseudotuberculosis*: Potential Cheesy Gland Vaccine and Live Delivery Vehicle," *Infect. Immun.*, 1992, 60:2900-2905.

Hondalus et al., "The Intracellular Bacterium *Rhodococcus equi* Requires Mac-1 To Bind to Mammalian Cells," *Infect. Immun.*, 1993, 61:2919-2929.

Huang et al., "Parallelization of a local similarity algorithm," *CABIOS*, 1992, 8:155-165.

Iglesias et al., "Interleukin-6 and Interleukin-6 Soluble Receptor Regulate Proliferation of Normal, Human Papillomavirus-Immortalized, and Carcinoma-Derived Cervical Cells In Vitro," *Am. J. Pathol.*, 1995, 146:944-952.

Jones et al., "Phospholipase D and membrane traffic: Potential roles in regulated exocytosis, membrane delivery and vesicle budding," *Biochim. Biophys. Acta*, 1999, 1439:229-234.

Jurianz et al., "Complement resistance of tumor cells: basal and induced mechanisms," *Mol. Immunol.*, 1999, 36:929-939.

Källström et al., "Membrane cofactor protein (MCP or CD46) is a cellular pilus receptor for pathogenic *Neisseria*," *Mol. Microbiol.*, 1997, 25:639-647.

Källström et al., "Cholera toxin and extracellular $Ca^{2+}$ induce adherence of non-plliated *Neisseria*: evidence for an important role of G-proteins and Rho in the bacteria-cell interaction," *Cell Microbiol.*, 2000, 2:341-351.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Kaur and McDougall, "Characterization of Primary Human Keratinocytes Transformed by Human Papillomavirus Type 18," *J. Virol.*, 1988,. 62:1917-1924.

Ketterer et al.; "Infection of Primary Human Bronchial Epithelial Cells by *Haemophilus influenzae*: Macropinocytosis as a Mechanism of Airway Epithelial Cell Entry," *Infect. Immun.*, 1999, 4161-4170.

Köhler et al., "Continuous cultures of fused cells secreting antibody of predefined specificity," *Nature*, 1975, 256:495.

Kondo et al., "Phospholipase D Mimics Platelet-derived Growth Factor as a Competence Factor in Vascular Smooth Muscle Cells," *J. Biol. Chem.*, 1992, 267:23609-23616.

Kondo et al., "Two-dimensional electrophoretic studies on down-regulated intracellular transferrin in human fibroblasts immortalized by treatment with either 4-nitroquinoline 1-oxide or $^{60}Co$ gamma rays,." *Electrophoresis*, 1996, 17:1638-1642.

Kunkel, "Rapid and efficient site-specific mutagenesis without phenotype selection," *Proc. Natl. Acad. Sci. USA*, 1985, 82:488-492.

Kunkel et al., "Rapid and Efficient Site-Specific Mutagenesis without Phenotypic Selection," *Meth. Enzymol.*, 1987, 154:367-382.

Kusner et al., "Regulation of Phospholipase D Activity by Actin: Actin Exerts Bidirectional Modulation of Mammalian Phospholipase D Activity in a Polymerization-Dependent, Isoform-Specific Manner," *J. Biol.Chem.*, 2002, 277:50683-50692.

Kusner et al., "Evolutionary conservation of physical and functional interactions between phospholipase D and actin," *Arch. Biochem. Biophys.*, 2003, 412:231-241.

Lawn et al., "The sequence of human serum albumin cDNA and its expression in *E. coli*," *Nucl. Acids. Res.*, 1981, 9:6103-6114.

Lehninger, "The amino acid building blocks of proteins," *Biochemistry*, 2nd ed., 1975, 73-75.

Lin et al., "Increased Expression of Luteinizing Hormone/Human Chorionic Gonadotropin Receptor Gene in Human Endometrial Carcinomas," *J. Clin. Endocrinol. Metab.*, 1994, 79:1483-1491.

Lukowski et al., "Inhibition of Phospholipase D Activity by Fodrin: An Active Role for the Cytoskeleton," *J. Biol. Chem.*, 1996, 271:24164-24171.

Lynch et al., "Studies of Porins: Spontaneously Transferred from Whole Cells and Reconstituted from Purified Proteins of *Neisseria gonorrhoeae* and *Neisseria meningitides*," *Biophys. J.*, 1984, 45:104-107.

Maisner et al., "Membrane Cofactor Protein (CD46) Is a Basolateral Protein That Is Not Endocytosed," *J. Biol. Chem.*, 1997, 272:20793-20799.

Maitra et al., "Enrichment of epithelial cells for molecular studies," *Nature Med.*, 1999, 5:459-463.

Mandell et al. (eds), Principles and Practice of Infectious Disease, 3rd ed., 1990, Churchill Livingstone Inc. (TOC only).

McGee et al., "Mechanisms of Mucosal Invasion by Pathogenic *Neisseria*," *Rev. Infect. Dis.*, 1983, 5:S708-S714.

McGhee et al., "New Perspectives in Mucosal Immunity with Emphasis on Vaccine Development," *Sem. Hematol.*, 1993, 30:3-15.

McNamara et al., "Toxic phospholipases D of *Corynebacterium pseudotuberculosis, C. ulcerans* and *Arcanobacterium haemolyticum*: cloning and sequence homology," *Gene*, 1995, 156:113-118.

McNeely, Jr., et al., "Treatment of Chlamydial Infections of the Cervix During Pregnancy," *Sex. Trans. Dis.* 1989, 16:60-62.

Meinkoth and Wahl, "Hybridization of Nucleic Acids Immobilized on Solid Supports," *Anal. Biochem.*, 1984, 138:267-284.

Moll et al., "The Catalog of Human Cytokeratins: Patterns of Expression in Normal Epithelia, Tumors and Cultured Cells," *Cell*, 1982, 31:11-24.

Morse and Bartenstein, "Purine metabolism in *Neisseria gonorrhoeae*: the requirement for hypoxanthine," *Can. J. Microbiol.*, 1980, 26:13-20.

Moulder, "Comparative Biology of Intracellular Parasitism," *Microbiol. Rev.*, 1985, 49:298-337.

Mukherjee et al., "Endocytosis," *Physiol. Rev.*, 1997, 77:759-803.

Myers and Miller, "Optimal alignments in linear space," *CABIOS*, 1998, 4:11-17.

Needleman and Wunsch, "A General Method Applicable to the Search for Similarities in the Amino Acid Sequence of Two Proteins," *J. Mol. Biol.*, 1970, 48:443-453.

Obermeier et al., "PAK promotes morphological changes by acting upstream of Rac," *EMBO J.*, 1998, 17:4328-4339.

Oelschlaeger et al., "Unusual microtubule-dependent endocytosis mechanisms triggered by *Campylobacter jejuni* and *Citrobacter freundii*," *Proc. Natl. Acad. Sci. USA*, 1993, 90:6884-6888.

O'Gorman et al., "Decreased Insulin-like Growth Factor-II/Mannose 6-Phosphate Receptor Expression Enhances Tumorigenicity in JEG-3 Cells," *Cancer Res.*, 1999, 59:5692-5694.

Ohtsuka et al., "An Alternative Approach to Deoxyoligonucleotides as Hybridization Probes by Insertion of Deoxyinosine at Ambiguous Codon Positions," *J. Biol. Chem.*, 1985, 260:2605-2608.

Parkhill et al., "Complete DNA sequence of a serogroup A strain of *Neisseria meningitidis* Z2491," *Nature*, 2000, 404:502-506.

Pearson and Lipman, "Improved tools for biological sequence comparison," *Proc. Natl. Acad. Sci. USA*, 1988, 85:2444-2448.

Pearson et al., "Using the FASTA Program to Search Protein and DNA Sequence Databases," *Meth. Mol. Biol.*, 1994, 24:307-331.

Ponting and Kerr, "A novel family of phospholipase D homologues that includes phospholipid synthases and putative endonucleases: Identification of duplicated repeats and potential active site residues," *Prot. Science*, 1996, 5:914-922.

Price and Boettcher, "The Presence of Complement in Human Cervical Mucus and its Possible Relevance to Infertility in Women with Complement-Dependent Sperm-Immobilizing Antibodies," *Fertil. Steril.*, 1979, 32:61-66.

Rabinovitch, "Professional and non-professional phagocytes: an introduction," *Trends Cell Biol.*, 1995, 5:85-88.

Ramos et al., "The Elevated Natural Killer Sensitivity of Targets Carrying Surface-Attached C3 Fragments Require the Availability of the iC3b Receptor (CR3) on the Effectors," *J. Immunol.*, 1988, 140:1239-1243.

Ramos et al., "Complement-dependent cellular cytotoxicity: Lymphoblastoid lines that activate complement component 3 (C3) and express C3 receptors have increased sensitivity to lymphocyte-mediated lysis in the presence of fresh human serum," *Proc. Natl. Acad. Sci. USA*, 1985, 82:5470-5474.

Relman et al., "Recognition of a Bacterial Adhesin by an Integrin: Macrophage CR3 ($\alpha_M\beta_2$, CD11b/CD18) Binds Filamentous Hemagglutinin of *Bordetella pertussis*," *Cell*, 1990, 61:1375-1382.

Richardson and Sadoff, "Induced Engulfment of *Neisseria gonorrhoeae* by Tissue Culture Cells," *Infect. Immun.*, 1988, 56:2512-2514.

Robinson, "The role of clathrin, adaptors and dynamin in endocytosis," *Curr. Opin. Cell Biol.*, 1994, 6:538-544.

Rosqvist et al., "Functional conservation of the secretion and translocation machinery for virulence proteins or yersiniae, salmonellae and shigellae," *EMBO J.*, 1995, 14:4187-4195.

Ross and Densen, "Opsonophagocytosis of *Neisseria gonorrhoeae*: Interaction of Local and Disseminated Isolated with Complement and Neutrophils," *J. Infect. Dis.*, 1985, 151:33-41.

Rossolini et al., "Use of deoxyinosine-containing primers vs degenerate primers for polymerase chain reaction based on ambiguous sequence information," *Mol. Cell Probes*, 1994, 8:91-98.

Schmidt and Hall, "Signaling to the Actin Cytoskeleton," *Annu. Rev. Cell Dev. Biol.*, 1998, 14:305-338.

Schoolnik et al., "Gonococcal Pili: Primary Structure and Receptor Binding Domain," *J. Exp. Med.*, 1984, 159:1351-1370.

Segal et al., "Role of Chromosomal Rearrangement in *N. gonorrhoeae* Pilus Phase Variation," *Cell*, 1985, 40:293-300.

Sells et al., "Human p21-activated kinase (Pak1) regulates actin organization in mammalian cells," *Curr. Biol.*, 1997, 7:202-210.

Seya et al., "Quantitative Analysis of Membrane Cofactor Protein (MCP) of Complement," *J. Immunol.*, 1990, 145:238-245.

Silverstein et al., "Endocytosis," *Ann. Rev. Biochem.*, 1977, 46:669-722.

Simmons et al., "Vaccine Potential Attenuated Mutants of *Corynebacterium pseudotuberculosis* in Sheep," *Infect. Immun.*, 1998, 66:474-479.

Sizemore and Rorke, "Human Papillomavirus 16 Immortalization of Normal Human Ectocervical Epithelial Cells Alters Retinoic Acid Regulation of Cell Growth and Epidermal Growth Factor Receptor Expression," *Cancer Res.*, 1993, 53:4511-4517.

Skoudy et al., "A functional role for ezrin during *Shigella flexneri* entry into epithelial cells," *J. Cell. Sci.*, 1999, 112:2059-2068.

Smedts et al., "Changing Patterns of Keratin Expression During Progression of Cervical Intraepithelial Neoplasia,", *Am. J. Pathol.*, 1990, 136:657-668.

Smedts et al., "Keratin Expression in Cervical Cancer," *Am. J. Pathol.*, 1992, 141:497-511.

Smith and Waterman, "Comparison of Biosequences," *Adv. Appl. Math.*, 1981, 2:482-489.

Stephens, "Gonococcal and Meningococcal Pathogenesis as Defined by Human Cell, Cell Culture, and Organ Culture Assays," *Clin. Microbiol. Rev.*, 1989, 2:S104-S111.

Stewart et al., "T Cell Adhesion to Intercellular Adhesion Molecule-1 (ICAM-1) Is Controlled by Cell Spreading and the Activation of Integrin LFA-1[1]," *J. Immunol.*, 1996, 156:1810-1817.

Stock et al., "CD66-dependent neutrophil activation: a possible mechanism for vascular selectin-mediated regulation of neutrophil adhesion," *J. Leuk. Biol.*, 1995, 58:40-48.

Stock et al., "CD66: role in the regulation of neutrophil effector function," *Eur. J. Immunol.*, 1996, 26:2924-2932.

Stryer, "Conformation and Dynamics," *Biochemistry*, 2nd ed., 1981, 14-15.

Sülz et al., "The expression of $\alpha_v$ and $\beta_3$ integrin subunits in the normal human Fallopian tube epithelium suggests the occurence of a tubal implantation window," *Hum. Reprod.*, 1998, 13:2916-2920.

Sun et al., "In Vivo Cytokeratin-Expression Pattern of Stratified Squamous Epithelium from Human Papillomavirus-Type-16-Immortalized Ectocervical and Foreskin Keratinocytes," *Int. J. Cancer*, 1993, 54:656-662.

Swanson and Baer, "Phagocytosis by zippers and triggers," *Trends Cell Biol.*, 1995, 5:89-93.

Swanson and Watts, "Macropinocytosis," *Trends Cell Biol.*, 1995, 5:424-428.

Tettelin et al., "Complete Genome Sequence of *Neisseria meningitidis* Serogroup B Strain MC58," *Science*, 2000, 287:1809-1815.

Tran Van Nhieu and Sansonetti, "Mechanism of *Shigella* entry into epithelial cells," *Curr. Opin. Microbiol.*, 1999, 2:51-55.

Turner and Foster, "The Potential Exploitation of Plant Viral Translational Enhancers in Biotechnology for Increased Gene Expression," *Mol. Biotech.*, 1995, 3:225-236.

van Dijk et al., "Exogenous phospholipase D generates lysophosphatidic acid and activates Ras, Rho and $Ca^{2+}$ signaling pathways," *Curr. Biol.*, 1998, 8:386-392.

Vanderpuye et al., "The Complement System in Human Reproduction," *Am. J. Reprod. Immunol.*, 1992, 27:145-155.

Violette et al., "Differences in the Binding of Blocking Anti-CD11b Monoclonal Antibodies to the A-Domain of CD11b," *J. Immunol.*, 1995, 155:3092-3101.

Wåhlin et al., "C3 Receptors on Human Lymphocyte Subsets and Recruitment of ADCC Effector Cells by C3 Fragments," *J. Immunol.*, 1983, 130:2831-2836.

Waite, "The PLD superfamily: insights into catalysis," *Biochim. Biophys. Acta*, 1999, 1439:187-197.

Watarai et al., "Interaction of Ipa Proteins of *Shigella flexneri* with $\alpha_5\beta_1$ Integrin Promotes Entry of the Bacteria into Mammalian Cells," *J. Exp. Med.*, 1996, 183:991-999.

Wen et al., "Interaction of the Gonococcal Porin P.IB with G- and F-Actin," *Biochem.*, 2000, 39:8638-8647.

Wetzler et al., "Gonococcal Lipooligosaccharide Sialylation Prevents Complement-Dependent Killing by Immune Sera," *Infect. Immun.*, 1992, 60:39-43.

Wright et al., "Identification of the C3bi receptor of human monocytes and macrophages by using monoclonal antibodies," *Proc. Natl. Acad. Sci. USA*, 1983, 80:5699-5703.

Zhang and Chait, "Pro-Found: An Expert System for Protein Identification Using Mass Spectrometric Peptide Mapping Information," *Anal. Chem.*, 2000, 72:2482-2489.

Zhang et al., "Enhanced immunogenicity of a genetic chimeric protein consisting of two virulence antigens of *Streptococcus mutans* and protection against infection", *Infect Immun.*, 70(12), 6779-6787 (2002).

Zipfel et al., "Factor H and disease: a complement regulator affects vital body functions," *Mol. Immunol.*, 1999, 36:241-248.

\* cited by examiner

The Effect of Clostridium C3 Toxin on Gonococcal Invasion of Primary Cervical Cells

|         | Ectocervical | Endocervical |
|---------|--------------|--------------|
| No Toxin | 2.5868 | 1.6153 |
| C3 Toxin | 0.0945 | 0.3123 |

*FIG. 3*

1 μm    10 min

1 μm    10 min

2 μm    20 min

1 μm    30 min

5 μm    30 min

1 μm    90 min

1 μm     30 min

8 μm     90 min

VACCINE AND COMPOSITIONS FOR THE PREVENTION AND TREATMENT OF NEISSERIAL INFECTIONS

CLAIM OF PRIORITY

This application claims priority under 35 USC 119(e) from U.S. Provisional Application Ser. No. 60/266,070, filed Jan. 31, 2001; U.S. Provisional Application Ser. No. 60/310,356, filed Aug. 6, 2001; and U.S. Provisional Application Ser. No. 60/344,452, filed Oct. 23, 2001; all of which applications are incorporated herein by reference.

The invention was made with the support of NIH Grant No. 5UI9AI43924. The U.S. government has certain rights in the invention.

BACKGROUND OF THE INVENTION

*Neisseria gonorrhoeae* is the causative agent of the disease gonorrhea. Approximately 300,000 women a year contract gonorrhea in the U.S. Worldwide, the number of women with this infection is in the millions. It is a major cause of infertility and pelvic inflammatory disease. It is also a major co-factor in the spread of HIV1.

In men, gonococcal infection develops as an acute urethritis that is typically characterized by a purulent discharge that results as a consequence of the concurrent inflammatory response to infection. In women, gonococcal infection can develop as an ascending infection of the genital tract that can lead to an acute pelvic inflammatory disease, infertility, or ectopic pregnancy. High proportions of women, however, initially develop asymptomatic gonococcal infections, in contrast to *N. gonorrhoeae* infection in men.

The mechanisms by which the gonococcus infects and invades the female genital tract are only beginning to be understood. Research has shown that gonococci are capable of invading primary human epithelial cells derived from both the endo- and the ectocervix. These studies implied that the mechanism(s) used by the gonococcus to breech the cervical epithelium are distinct from those mechanisms used to invade the urethral epithelium of men and that several endocytic mechanisms appear to play a role in gonococcal invasion of the female genital tract.

Currently there is no vaccine for the prevention of gonorrhea in men or women. Therefore, there is a need for an effective means to prevent or ameliorate neisserial infections in women.

SUMMARY OF THE INVENTION

The present invention provides a polypeptide, polynucleotide, vaccine, and methods of vaccination effective to immunize a susceptible female patient against *Neisseria gonorrhoeae*. Such immunization can prevent, ameliorate or reduce the incidence of gonorrhea in women. The vaccine contains an immunogenic amount of polypeptide comprising polypeptide p177, p88, p64, p55 or p46 from *N. gonorrhoeae*, in combination with a physiologically-acceptable, non-toxic vehicle. An example of p177 is amino acid sequence SEQ ID NO:1; an example of p88 is SEQ ID NO:2; an example of p64 is SEQ ID NO:3; an example of p55 is SEQ ID NO:4; and an example of p46 is SEQ ID NO:5. The polynucleotides of the present invention include nucleic acid sequences encoding polypeptide p177, p88, p64, p55 or p46 from *N. gonorrhoeae*. Polypeptide p177 may be encoded by SEQ ID NO:6; p88 may be encoded by SEQ ID NO:7; p64 may be encoded by SEQ ID NO:8; p55 may be encoded by SEQ ID NO:9; and p46 may be encoded by SEQ ID NO:10. The vaccine may further comprise an effective amount of an immunological adjuvant.

Also provided are methods of preventing infection or colonization of *Neisseria gonorrhoeae* in a female patient by administering to the patient a compound that inhibits CR3. The compound may be an antibody (monoclonal, polyclonal, or humanized) specific for CR3. Alternatively, the compound may be chemical or synthetic inhibitors e.g. peptides, carbohydrates, glycoproteins, glycolipids, or divalent cation chelators.

As used herein, the term "neisserial protein" includes variants or biologically active or inactive fragments of p177, p88, p64, p55 or p46 from *N. gonorrhoeae*. A "variant" of the polypeptide is a neisserial protein that is not completely identical to a native neisserial protein. A variant neisserial protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Stryer, L. *Biochemistry* (2d edition) W. H. Freeman and Co. San Francisco (1981), p. 14-15; Lehninger, A. *Biochemistry* (2d ed., 1975), p. 73-75.

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. Alternatively, amino acid substitutions in certain polypeptides may be used to provide residues that may then be linked to other molecules to provide peptide-molecule conjugates that retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a protein, as governed by the hydrophilicity of its adjacent amino acids, correlates with its immunogenicity. U.S. Pat. No. 4,554,101. Accordingly, it is noted that substitutions can be made based on the hydrophilicity assigned to each amino acid. In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant neisserial protein comprises at least seven amino acid residues, preferably about 20 to about 2000 residues, and more preferably about 50 to about 1000 residues, and even more preferably about 80 to about 200 residues, wherein the variant neisserial protein has at least 50%, preferably at least about 80%, and more preferably at least about 90% but less than 100%, contiguous amino acid sequence homology or identity to the amino acid sequence of a corresponding native neisserial protein.

The amino acid sequence of the variant neisserial protein corresponds essentially to the native neisserial protein amino acid sequence. As used herein "correspond essentially to" refers to a polypeptide sequence that will elicit a protective immunological response substantially the same as the response generated by native neisserial protein. Such a response may be at least 60% of the level generated by native neisserial protein, and may even be at least 80% of the level generated by native neisserial protein. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

A variant of the invention may include amino acid residues not present in the corresponding native neisserial protein, or may include deletions relative to the corresponding native neisserial protein. A variant may also be a truncated "fragment" as compared to the corresponding native neisserial protein, i.e., only a portion of a full-length protein. Neisserial protein variants also include peptides having at least one D-amino acid.

The neisserial protein of the present invention may be expressed from an isolated nucleic acid (DNA or RNA) sequence encoding the neisserial protein. Amino acid changes from the native to the variant neisserial protein may be achieved by changing the codons of the corresponding nucleic acid sequence. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The neisserial protein as described above may be operably linked to an amino acid sequence for a therapeutic agent. An amino acid or nucleic acid is "operably linked" when it is placed into a functional relationship with another amino acid or nucleic acid sequence. For example, DNA a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the amino acid or nucleic acid sequences being linked are contiguous, and, in the case of a secretory leader in DNA, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "therapeutic agent" refers to any agent or material that has a beneficial effect on the mammalian recipient. Thus, "therapeutic agent" embraces both therapeutic and prophylactic molecules having nucleic acid or protein components.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1. Anti-CR3 antibodies inhibit gonococcal attachment and invasion of CR3-transfected CHO cells. CHO-CR3 cell monolayers were pretreated with antibodies to the CR3 alpha subunit CD11b (H5A4, Bear1) or CD18 (anti-CD18, IB4) or anti-CD18 antibody and an anti-CD18 blocking peptide as outlined in the text. Antibody-treated cell monolayers were challenged for two hours with gonococci prior to gentimicin addition, cervical cell lysis, and plating of serial dilutions to determine colony-forming units. Gentamicin treatment was omitted from attachment assays. Percent inhibition was determined as a normalized function of the ability of gonococci to adhere to or invade CHO-CR3 cells in the absence of antibody. Values given are the mean values of at least three trials. A Kruskal-Wallis analysis of variance was used to determine the statistical significance of the invasion assays. ρ-values were less than 0.05 for all of the antibodies tested alone.

FIG. 2. Anti-CR3 antibodies inhibit gonococcal invasion of primary cervical cells. Invasion of primary, human, ecto- and endocervical cell monolayers by gonococci was performed as outlined in the text. Antibodies H5A4 and Bear1 recognize the CR3 alpha subunit, CD11b. Anti-CD18 and IB4 are specific for the CR3 beta subunit, CD18. Inhibition of invasion was determined as a normalized function of the ability of gonococci to invade primary ecto- and endocervical cells in the absence of antibody. Values given are the mean values of at least three trials. A Kruskal-Wallis analysis of variance was used to determine the statistical significance of the invasion assays. ρ-values were less than 0.05 for all of the antibodies tested.

FIG. 3. The effect of *Clostridium* C3 neurotoxin on the invasion of primary cervical cells by *N. gonorrhoeae*. The ability of gonococci to invade primary ecto- and endocervical cells was determined as outlined in the text. Invasion was determined as a proportion of the original infection inoculum. Values given are the mean values of three trials. A Kruskal-Wallis analysis of variance was used to determine the statistical significance of percent invasion with C3 toxin in comparison to percent invasion without C3 toxin treatment. ρ-values were 0.05 for each assay.

FIG. 4. Laser scanning confocal microscopy (LSCM) demonstrates that the characteristic cytokeratin staining pattern of the tissue biopsies (left panels of FIG. 4) has been retained in the respective primary cervical epithelial cell cultures (right panels of FIG. 4). Sectioned tissue biopsies and primary cervical epithelial cell monolayers were incubated with a FITC-conjugated antibody to the noted specific cytokeratin. Ethidium bromide was used to counter-stain the tissue sections. Endocervical cells labeled intensely with antibody 8.12, which is specific for type I cytokeratins 13, 15, and 16 (panel A1 and A2). The labeling of endocervical cells with an antibody specific for type II cytokeratin 4 (panel C1 and C2) was considerably less intense, and it was not uniformly distributed. Ectocervical cells labeled positive with an antibody specific for cytokeratins 13, 15, and 16 (panel B1 and B2) and cytokeratin 4 (panel D1 and D2).

FIG. 5. Scanning electron microscopy (SEM) analysis shows the predominant changes that occur in the cervical cell membrane over the course of a three hour infection as the result of cervical epithelial cell-gonococcal interactions. At early (0 to 60 minutes) phases of infection *N. gonorrhoeae* could be found on the surface of endocervical cells either associated with microvilli (A) or undergoing an endocytic process (B). As the infection process continued, microvilli appeared to acquire directionality. Filopodia/lamellipodia became evident after thirty minutes post infection (C). Bacteria appeared to be in the process of internalization (D). Loss of microvilli with a smoothing of the cervical cell membrane around the periphery of some sites of gonococcal infection also became evident at approximately thirty minutes post infection (E). Membrane ruffles (F, endocervical; G, ectocervical) appeared at sixty minutes, and they became prevalent at ninety minutes post infection. Ruffles could be induced to occur at approximately thirty minutes post infection with use of a primed infection inoculum (see Example 1) (G). A visible smoothing of the cervical cell membrane encircling membrane ruffles can be seen (H). By three hours post infection large ruffles could readily be observed.

FIG. 6. Bright-field light microscopy (BFLM) and immuno-transmission electron microscopy (TEM) studies demonstrate ruffling of the cervical surface and invasion of the primary cervical epithelial cells at ninety minutes and three hours post infection. For TEM analysis, bacteria were labeled with an antibody specific to the gonococcal surface protein, H.8; cervical cells were labeled with a polyclonal antibody to actin. 30 nm and 10 nm gold bead antibody-conjugates were used to label the bacteria- and host-specific primary antibodies, respectively. Membrane protrusions can be seen that are labeled with actin and that are encompassing gonococci at ninety minutes after the onset of infection (A). Bacteria can also be seen entering the cervical cell as individual entities in actin-lined, spacious vacuoles (B). Large membrane ruffles can be seen associating with gonococci at three hours post infection (C and D). For BFLM (D) thick (1 m) paraffin sections of endocervical cells were stained with hematoxylin and eosin. Arrows denote bacteria. Bar=2 μm.

FIG. 7. This figure shows TEM studies of cervical biopsies from women with gonococcal cervicitis. Panels A and B demonstrate cytoskeletal changes and membrane ruffling occur during naturally acquired gonococcal infection. Panel A and panel B show large and small membrane protrusions associated with gonococci (designated by arrows) that are similar to those seen in FIG. 6.

FIG. 8. Differential interference contrast (DIC) and LSCM analysis demonstrate co-localization of *N. gonorrhoeae* 1291-green with a concentrated accumulation of the actin-associated protein, vinculin. In panel A, vinculin was immunolabeled with a TRITC-conjugated antibody and in a colored version of this figure was visible as a red fluorescence (A); in panel B, bacteria were transformed with green fluorescent protein (GFP) and in a colored version of this figure were visible as a green fluorescence. (C) In a merged image of panels A and B, arrows denote co-localization of bacteria with vinculin, which was visualized in a colored version of this figure as a yellow-orange because of the combined signal of the individual fluorophores. (D) Merged LSCM and DIC image (of the ectocervical cells). Similar results were seen with endocervical cells and for the actin-associated proteins ezrin and myosin, but the focal accumulation of a-actinin and talin was less pronounced. No accumulation of actin-associated proteins was observed in uninfected (control) cervical epithelial cells. Magnification, ×20.

Figure 9A:
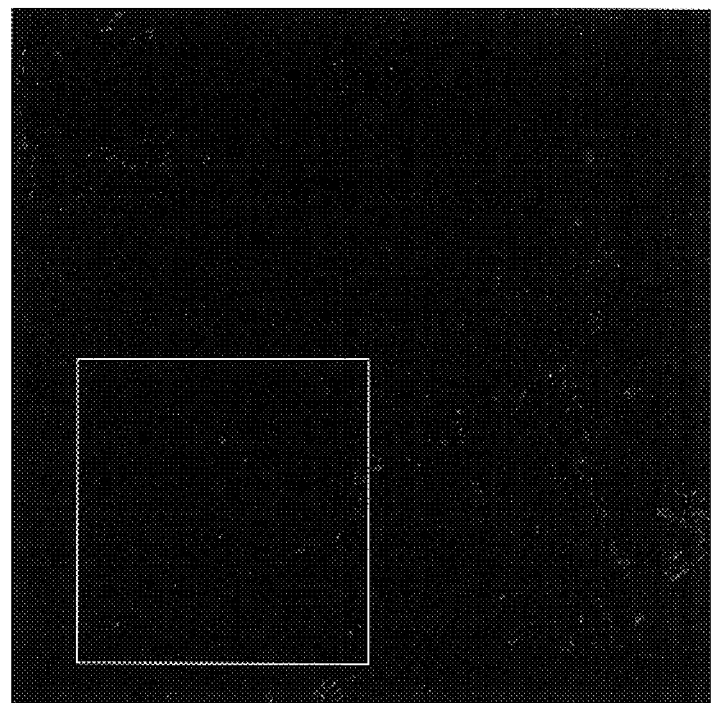
Figure 9B:
Figure 9C:
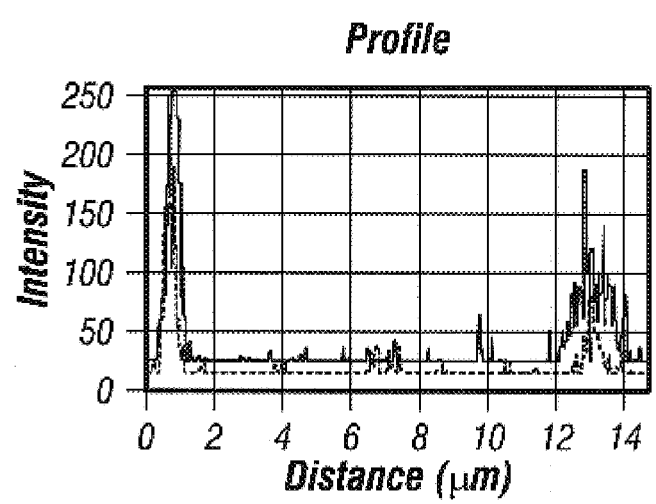

FIG. 9. *Neisseria gonorrhoeae* co-localizes with CR3 in vivo. Cryosections of a clinical biopsy derived from a women with documented gonococcal cervicitis were immunolabeled with anti-CD18 (visible as a green fluorescence) and 2C3 (specific for gonococcal H.8 outer membrane protein, visible as a red fluorescence) antibodies. Co-localization of CR3 with gonococci occurs as a yellow fluorescence because of the combined signal of the two fluorophores. A) 63× oil B) 5× zoom image of the area designated by the white box in A. Co-localization is confirmed as a profile plot of the area designated by the red line where the individual fluorescence of each fluorophore is recorded and plotted, individually, by the viewing system. C) Areas of confirmed co-localization are observed where the peaks of the lines of the graph overlap.

Figure 10:
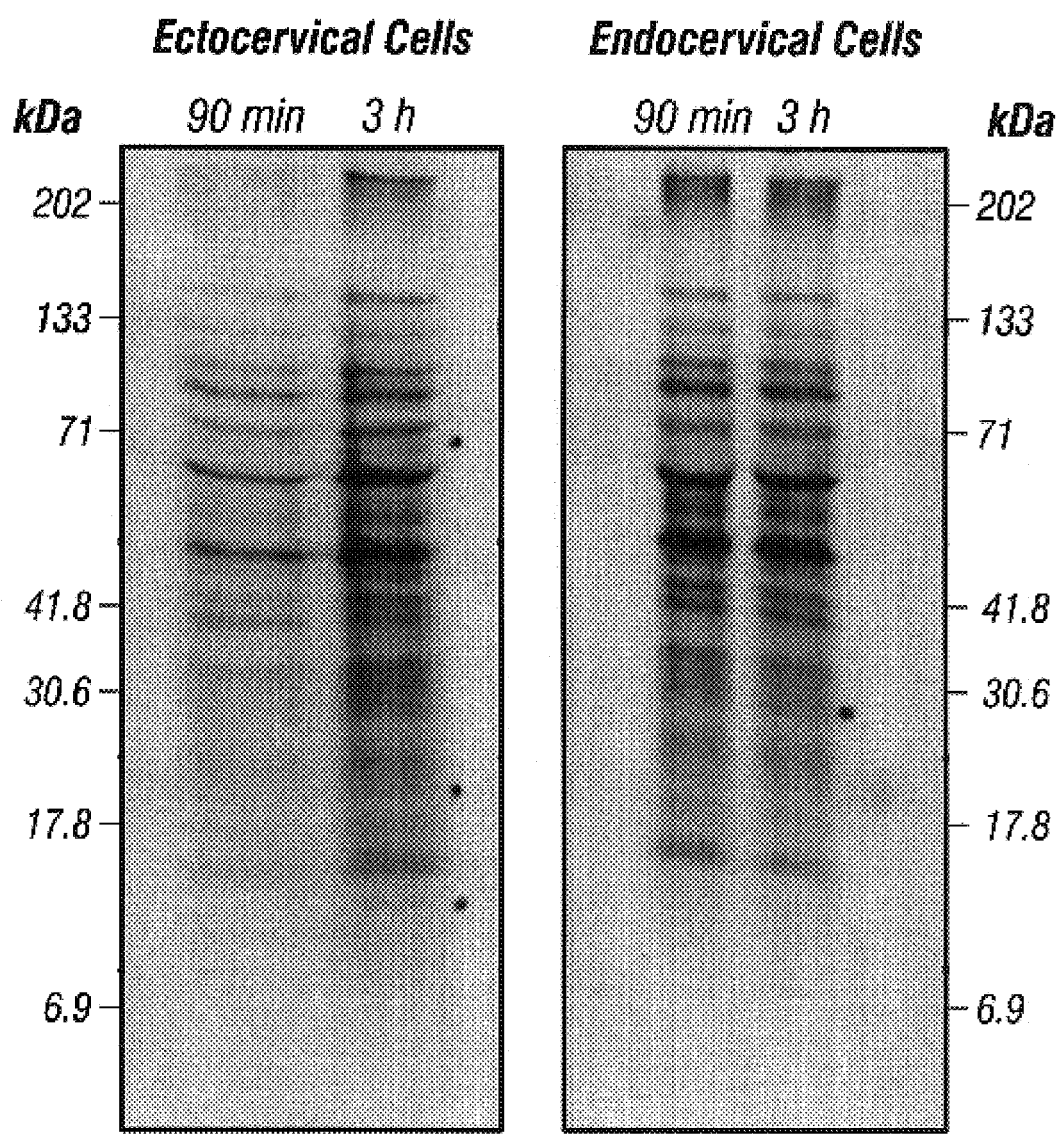

FIG. 10. Bacterial products that are released with gonococcal infection.

Figure 11:
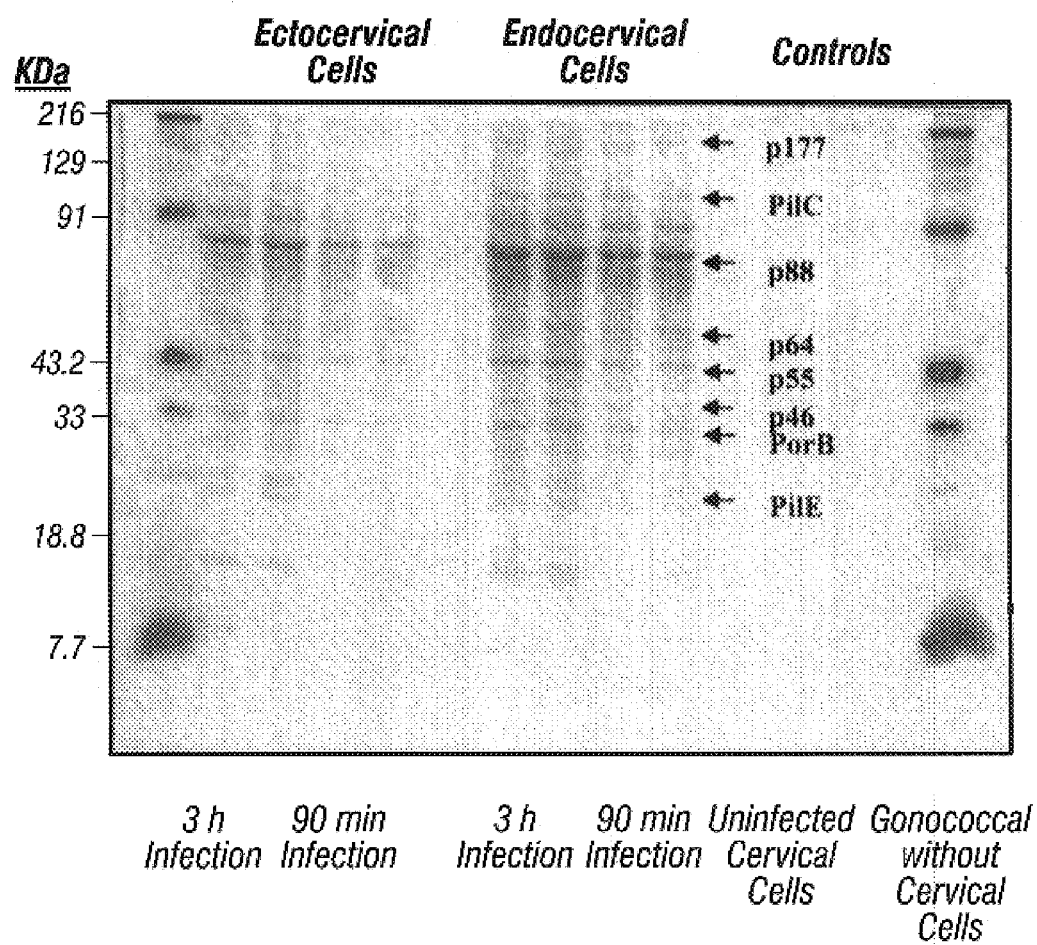

FIG. 11. Proteomic analysis of gonococcal products released with cervical cell infection.

DETAILED DESCRIPTION OF THE INVENTION

Definitions

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.*, 19:508 (1991); Ohtsuka et al., *JBC*, 260:2605 (1985); Rossolini et al., *Mol. Cell. Probes*, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook et al., Cold Spring Harbor, N.Y.: Cold Spring Harbor Laboratory Press (1989).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similaritymethod of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T. is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. *Biochem.*, 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, *Proc. Natl. Acad. Sci. USA*, 82:488 (1985); Kunkel et al., *Meth. Enzymol.*, 154:367 (1987); U.S. Pat. No. 4,873,192; Walker and Gaastra, *Techniques in Mol. Biol.* (MacMillan Publishing Co. (1983), and the references cited therein. Guidance as to appropriate amino acid substitutions that do not affect biological activity of the protein of interest may be found in the model of Dayhoff et al., *Atlas of Protein Sequence and Structure* (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (O). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook et al., *Molecular Cloning: A Laboratory Manual* (2d ed., Cold Spring Harbor Laboratory Press, Plainview, N.Y.) (1989). See also Innis et al., *PCR Protocols*, Academic Press (1995); and Gelfand, *PCR Strategies*, Academic Press (1995); and Innis and Gelfand, *PCR Methods Manual*, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment", as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

Direct Association of CR3 with Pathogenic *Neisseria*

Phagocytosis that is mediated by complement receptor type 3 (CR3) occurs independently of a proinflammatory response in immune cells (Caron et al. 1998). CR3 exists as an integrin heterodimer composed of an alpha ($\alpha_M$ or CD11b) and a beta ($\beta_2$ or CD18) subunit. The distribution of CR3 is thought to be limited to professional phagocytes; however, Hussain et al. (1995) demonstrated the expression of CR3 in rectal epithelia. Additionally, Hussain et al. (1995) were able to detect the presence of CD11b in a small subpopulation of cervicovaginal epithelia, although they were unable to detect the presence of CD18.

Up-regulation of CD11b in neutrophils has been documented in response to *Neisseria meningiditis* infection (Kragsbjerg et al. 2000). The direct association of CR3 with pathogenic *Neisseria*, however, has not been demonstrated. The present inventors herein describe the occurrence of CR3 expression in primary human cervical epithelial cells and its co-localization with *N. gonorrhoeae* upon infection of these primary epithelial cells. They also describe the distribution of CR3 in immortalized tissue culture cell lines and within tissue biopsies derived from the male and female urogenital tracts. Monoclonal antibodies directed against CR3 inhibit gonococcal invasion of primary cervical cells and of CR3-transfected CHO cells suggesting that CR3 serves as a receptor for *N. gonorrhoeae* during infection. In addition, these studies help to explain why the inflammatory response initiated by gonococcal infection of the lower female genital tract differs from that observed with gonococcal infection of the male urogenital genital tract.

The distribution of CR3 in tissue biopsies derived from defined sites within the human male and female genital tracts and in primary, immortalized, and malignant epithelial cells derived from these sites is described in Example 2 below. Laser scanning confocal microscopy (LSCM) demonstrated CR3 was not present in tissues and cell derived from the male urogenital tract and from tissue derived from the female urethra; however, CR3 was present on tissues and cells derived from the female genital tract. CR3 expression was greatest within the ectocervix tissue. Surface levels of CR3 appeared to decrease progressively from the ectocervix to the upper female genital tract in these tissues. A low level of CR3-associated immunofluorescence was observed in fallopian tube tissue. Consistent with results obtained with LSCM analysis of tissue biopsies, primary endo- and ecto-cervical cells possessed both CR3 subunits, and CR3 expression appeared to be greater on primary ectocervical cells in comparison to primary endocervical cells.

Figure 2:
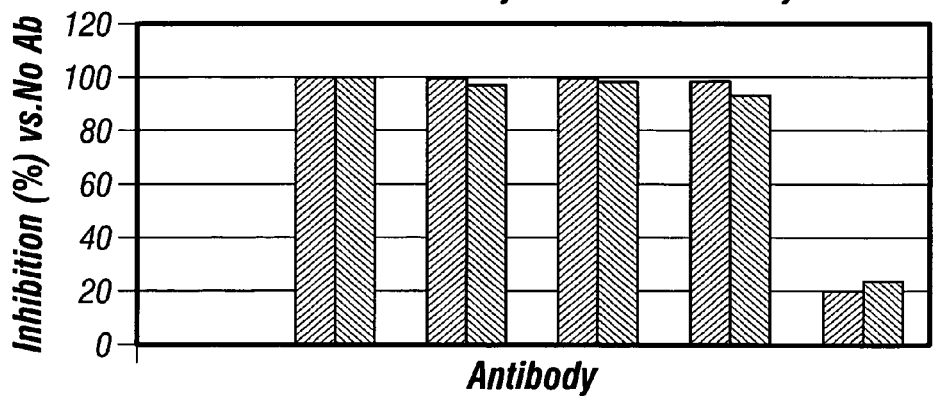

In contrast to results obtained with analysis of tissue biopsies and primary cervical cells, CR3 expression was negligible on immortalized and malignant cell lines (i.e., HCK, End1, ME180, Hec1B). Infection studies using *N. gonorrhoeae* strains 1291, 1291-green, MS11-green, or FA1090-green did not significantly influence the level of CR3 surface expression on these immortalized or malignant cell lines. However, *N. gonorrhoeae* did appear in induce up-regulation of CR3 surface expression on primary endo- and ectocervical cells. Gonococci were observed to co-localize with CR3 on primary cervical cells, and co-localization became increasingly prominent with extended infection. Immunoprecipitation studies confirmed the presence of CD11b and CD18 in primary cervical cells and CR3 co-localization with the gonococcus. Gonococci bound CR3-transfected K562 and CHO cells, and binding could be inhibited by the presence of anti-CD11b or -CD18 antibodies (FIG. 1). Similarly, invasion of primary cervical cells and CHO-CR3 cells could be inhibited by the addition of anti-CR3 antibodies to gentimicin-survival assays (FIGS. 1 and 2). Gonococcal invasion of primary endo- and ectocervical cells was also inhibited by the addition of *Clostridium* C3 neurotoxin to invasion assays (FIG. 3), which is consistent with CR3-mediated phagocytosis (Caron et al. 1998).

Extensive membrane ruffling could be induced to occur in the absence of gonococci in primary endo- and ectocervical cells and in CHO-CR3 cells by the addition of anti-CD11b or -CD18 antibodies to infection assays. This suggests that engagement of CR3 elicits membrane ruffling, which occurs in response to *N. gonorrhoeae* infection of the cervical epithelium.

The role of complement (C') in innate immunity is multifactorial; however, C' predominately serves to eliminate foreign antigens and to regulate the inflammatory response directed towards these exogenous particles. C' protein C3 of the C' alternative pathway (AP) plays a paramount role in AP C' regulation in that it serves to amplify the complement-mediated response by a positive feedback regulatory loop, which converts a relatively inefficient response to a highly efficient defense mechanism. Activation of the AP occurs constitutively at a low rate, which is tightly regulated by C' regulatory proteins, e.g., factors H (fH) and I (fI). Deposition of C3 on an exogenous surface (e.g. a bacterium) results in spontaneous C3 hydrolysis to produce C3b. C3b can bind factor B (fB) to generate C3 convertase activity leading to the formation of the membrane attack complex. Alternatively, C3b can bind fH leading to C' inactivation via cleavage of C3b by fI to produce iC3b, a ligand for CR3.

CR3 distribution has generally been considered to be limited to immune cells (e.g., monocytes, neutrophils, and macrophages); however, CR3 has also been found on renal glomerular (Sandilands et al. 1985) and rectal (Hussain et al. 1995) epithelial cells. By in situ hybridization Hussain et al. (1995) detected CD11b in a sub-population of endocervical tissue specimens, but they were unable to detect CD18. The inability to detect CD18 was attributed to a level of CR3 expression that was below the sensitivity of the antibody and detection method used (Hussain et al. 1995). LSCM of surgical biopsies and of primary endo- and ectocervical cell monolayers (using two, well defined, antibodies to each CR3 subunit) demonstrated CR3 within the ectocervical, endocervical, endometrial, and fallopian tube epithelia; however, CR3 expression appeared to progressively decrease from the ectocervix to the fallopian tubes. Although CR3 is structurally and functionally related to the very late antigen (VLA) sub-family of integrins, which are present within the female genital tract (Sülz et al. 1998), these two distinct groups of proteins are not immunologically cross-reactive (Hynes, R. O. 1987). Additionally, isotype control antibodies failed to label primary cell monolayers or tissue cryosections.

The present inventors' immunohistochemical data provide evidence for the presence of CR3 within the female genital tract. Furthermore, immunoprecipitation of primary cervical cell lysates confirmed the presence of CR3 within the endo- and ectocervix by the presence of the appropriate 95 kDa (CD18) and 170 kDa (CD11b) bands with subsequent western blotting. These data suggest that the distribution of CR3 should now be extended to include the endo- and ectocervix and, possibly, the epithelia of the endometrium and fallopian tubes. The female reproductive tract and seminal fluid have been hypothesized to exhibit anomalous C' regulatory characteristics that exist to ensure successful reproduction by hindering an amplified immune response to seminal plasma (Vanderpuye et al. 1992). Seminal plasma has been demonstrated to contain unidentified C1 and C3 C' component inhibitors, trace amounts of fH and fI, and a soluble form of the C3 regulatory protein, CD46 (Hussain et al. 1995), but fB has not been detected (Vanderpuye et al. 1992).

Full AP complement activity has been reported in cervical mucous (Price et al. 1979; Vanderpuye et al. 1992); however, C4 of the complement classical pathway (CP) was only detected in a small sub-population of luteal-phase cervical secretions (Vanderpuye et al. 1992). Additionally, AP, but not CP, components are produced by the vaginal epithelium (Price et al. 1979), and there are some data to suggest that C' components are synthesized by the endometrium (Vanderpuye et al. 1992). Collectively these data suggest that CR3 present within the female genital tract would function to eliminate exogenous antigens (with the absence of neutrophil influx), following C' inactivation of these antigens in seminal fluid or cervical mucous.

In contrast to the results obtained with female genital tissue and primary endo- and ectocervical cells, the presence of CR3 was not detected in vas deferens or male and female urethral tissue. The absence of CR3 in these tissues may be the result of divergent embryonic development that occurs after differentiation of the nephrogenic mesoderm. CR3 belongs to a large family of cell adhesion molecules that exhibit broad ligand specificity, and, in this respect, differential expression of integrin receptors has been implicated to play a role in morphogenesis and differentiation.

*Drosophila* spp. differentially express surface antigens, which structurally resemble human integrins, during the course of imaginal disc formation (Hynes, R. O. 1987). These cell surface molecules are hypothesized to influence embryonic development through differential cell adhesion (Hynes, R. O. 1987). In terms of evolutionary development, it is generally accepted that the female urogenital systems of apes and humans are more evolved than their male counterparts. In humans, the nephrogenic mesoderm differentiates to form the mesonephros and the metanephros. The metanephros gives rise to the renal glomerulus while the mesonephros regresses. Remnants of the mesonephric tubules exist in males as the vas deferens and in females as blind tubules in the ovarian dorsal mesentery. Muellerian ducts differentiate in females to form that portion of the female genital tract ranging from the fallopian tubes to the cephalic vagina. A complete division of the cloaca gives rise to the rectum and a urogenital sinus in both males and females. In males the muellerian ducts regress, and the urogenital sinus receives the mesonephric ducts, after which the rectum elongates and differentiation occurs. In females an additional portioning event of the urogenital sinus occurs to form the terminal vagina, the rectum, and the urethra. Since CR3 has been demonstrated on renal glomerular epithelium, rectal epithelium, and (considering the data of Hussain et al. (1995) and herein) the cervical epithelium, it is possible, although speculative, that the presence of CR3 in these tissues may correlate with a higher degree of embryonic development or cellular differentiation.

The absence of CR3 on the immortalized (End1, HCK) and the malignant (ME180, Hec1B) cell lines used in these studies may be reflective of the functional properties of integrins in general or CR3 specifically. Tumor cells are frequently altered in their integrin expression patterns (Jones et al. 1999) as well as the expression of other cellular receptors, e.g., complement receptor type 1 (CR1) (Seya et al. 1990) and the insulin-like growth factor-II/mannose-6-phosphate receptor (O'Gorman et al. 1999). Generally, adhesion and/or stimulation of integrins initiate signaling events that allow cytoskeletal rearrangements, cellular migration, and immunological activation. Adhesive and cytoskeletal defects are associated with fibronectin loss on transformed cells; these defects are reasoned to be due to altered integrin function (Hynes, R. O. 1987). CR3 initiates a signaling cascade in which PI 3-kinase functions as one effector (Elemer et al. 1994).

One function of PI-3 kinase is activation of the Rho family of small GTPases that, in turn, activate Jun-N-terminal kinase (JNK) (Hauck et al. 1998; Obermeier et al. 1998). Effector functions of JNK include regulation of gene expression and induction of apoptosis (Hauck et al. 1998). Some tumor cells express proteases most of which have been described to cleave C3 (Jurianz et al. 1999). Binding of C3 cleavage products (e.g., iC3b) to their respective receptors (e.g., CR3) could trigger multiple cellular responses, including apoptosis. Additionally, CR3 can also play a role in antibody-dependent cell-mediated cytotoxicity (ADCC) and complement-dependent cell-mediated cytotoxicity (CDCC) (Perlmann et al. 1983; Ramos et al. 1988; Ramos et al. 1985; Wåhlin et al. 1983), which facilitate tumor killing (Becherer et al. 1989; Erdei et al. 1991). Therefore, it could be reasoned that the absence of CR3 in immortal or malignant cells might confer a survival advantage to these cells.

A number of microorganisms have adapted mechanisms not only to evade complement-mediated killing but also to pilfer C' components for their own advantage. Microorganisms that initiate infection via C' receptors frequently activate C', which subsequently results in C3 deposition on their cell surface (Hondalus et al. 1993). The effect of C' deposition is two-fold: 1) it allows for evasion of immune surveillance, and 2) it allows targeting to the appropriate host cell (Cooper, N. R. 1991). Microbial entry of host cells in a CR3 opsonic-dependent manner is thought to lead to a milder respiratory burst thereby promoting increased intracellular survival (Mosser et al. 1987; Würzner, R. 1999). Additionally, complement-mediated endocytosis occurs independently of a proinflammatory response (Caron et al. 1998).

Asymptomatic gonococcal urethritis develops in a small proportion of men. In contrast, fifty to sixty percent of women with gonorrhea exhibit asymptomatic infections, and seventy percent of women with disseminated gonococcal infection (DGI) lack symptoms of genital track infection (Densen et al. 1982). The ability of pathogenic *Neisseria* to cause the range of disease states associated with infection requires highly efficient methods of immune avoidance. Although strain specific properties have been associated with resistance to complement-mediated killing (i.e., serum resistance) in vitro, most clinically isolated gonococci initially exhibit serum resistance, a property that is lost with sub-culturing (Densen, P. 1989; de la Paz et al. 1995; Ram et al. 1999; Ram et al. 1998; Vogel et al. 1999).

Ram et al. (1998) suggest that an increased conversion of C3b to iC3b on the gonococcal surface might contribute to serum resistance in vivo. This idea is supported by in vitro studies of gonococcal infection of neutrophils where a predominance of iC3b is found on the surface of gonococci in comparison to C3b deposition (Jarvis et al. 1999; McQuillen et al. 1999; Vogel et al. 1999). Conversion of C3b to iC3b on the gonococcal surface would permit efficient internalization of infecting gonococci into the cervical epithelium. Standard gentamicin-resistance assays measuring gonococcal invasion of primary endo- and ectocervical cells in the presence of anti-CR3 antibodies demonstrated greater than ninety-three percent invasion inhibition with the antibody inhibitors used.

Similar studies performed previously in the inventors' laboratory, using antibody inhibitors specific for other gonococcal ligands, failed to inhibit invasion of primary endo- and ectocervical cells. Additional support for a CR3-mediated mode of gonococcal invasion of the cervical epithelium is obtained from LSCM analysis of clinical biopsies derived from women with naturally acquired gonorrhea. Confirmed co-localization of gonococci with CR3 in these tissue sections provide evidence that CR3-mediated gonococcal invasion probably occurs in vivo. Collectively these data suggest that CR3-mediated phagocytosis may serve as the primary mode of gonococcal invasion of the cervical epithelium.

Only a small proportion of total cellular CR3 is found on the surface of resting cells (Frank et al. 1991; Ram et al. 1998). This CR3 population is relatively immobile in the plane of the cell membrane (van Kooyk et al. 1999) and is thought to facilitate phagocytosis triggered by other cell surface receptors, e.g. CR1 and Fcγ receptors (Frank et al. 1991). A mobile, intracellular CR3 store is associated with iC3b-dependent adherence (Frank et al. 1991). Upon activation this latent CR3 population, which resides in peroxidase-negative granules, is rapidly released, resulting in up to a ten-fold increase in CR3 surface expression (Elemer et al. 1994; Frank et al. 1991; Kishimoto et al. 1989). Early in the stages of phagocytosis CR3 aggregation also occurs (Caron et al. 1998; Elemer et al. 1994; Frank et al. 1991; Kishimoto et al. 1989; van Kooyk et al. 1999). LSCM analysis of *N. gonorrhoeae* infected primary endo- and ectocervical cells were reflective of these events. Co-localization of infecting gonococci was readily visible by thirty minutes post-infection of endo- and ectocervical cells, and this association became more pronounced by ninety minutes and three hours post-infection suggesting an increase in surface level expression of CR3. Additionally, co-localization of gonococci with CR3 was evident as clusters on the endo- and ectocervical cell surfaces.

Several studies have demonstrated that efficient signal transduction mediated through CR3 that subsequently allows phagocytosis may require co-operation among receptors that share adherence to a particular organism (Elemer et al. 1994; Frank et al. 1991; Hayashi et al. 1997; Ingalls et al. 1998; Kishimoto et al. 1989; Mesri et al. 1998; Stocks et al. 1995; Stocks et al. 1996; Wright et al. 1983). Cross-linking of this/these co-receptors to CR3 is thought to induce a conformational change in CR3 that leads to its increased ligand avidity and/or affinity followed by an increase in cell surface expression, a process called inside-out signaling. Studies focusing on the interaction of putative neisserial virulence factors with host cells have clearly demonstrated that the establishment of productive infection is multifactorial and several bacterial products may play a synergistic role in successful invasion.

Although the present inventors have demonstrated a role for CR3-mediated invasion of primary endo- and ectocervical cells by the gonococcus, the mechanism used by this bacterium to achieve CR3 adherence remains to be elucidated. Anti-CR3 immunoprecipitation studies of infected, primary endo- and ectocervical cell lysates demonstrated that gonococcal porin, pili, and opa proteins associate with CR3. These data may be indicative of opsonic (i.e., iC3b-mediated) adherence, alternatively, unopsonic binding of porin, pili, and opa proteins each to either CR3 or their respective co-receptor may facilitate CR3-mediated entry. CR3 up-regulation can be blocked by neutrophil treatment with an anion-specific channel blocker, but binding of neutrophils to endothelial cells remained unaffected (Kishimoto et al. 1989). *N. gonorrhoeae* porin proteins are anion selective water-filled channels that are capable of transmigration to and insertion into eukaryotic cell membranes (Bjerknes et al. 1995; Lynch et al. 1984); therefore, it is possible that these proteins play a role in up-regulation of CR3 upon gonococcal attachment.

Recent data has suggested that an association with selective members of the carcinoembryonic antigen family of cell adhesion molecules (CEACAM) (Stocks et al. 1995; Stocks et al. 1996) may augment CR3 activity. CEACAM are suggested to initiate a priming signal in neutrophils that results in activation of adhesion receptors without the release of inflammatory mediators or the induction of a respiratory burst (Stocks et al. 1995). CEACAM1 and CEACAM5 are also present on epithelial cells and have been shown to bind gonococcal Opa. It is tempting to speculate a role for an Opa-CEACAM interaction in CR3-mediated invasion. However, previous data and unpublished work in the inventors' laboratory has demonstrated that invasion of a *N. gonorrhoeae* strain FA1090 Opa deletion mutant and strain 1291 Opa phase variant (isolated on the basis of colony morphology) is comparable to their respective wild type counterparts. Additionally, membrane ruffling was observed upon SEM analysis of these Opa strains. Therefore the significance of Opa proteins to these studies is unclear.

One possibility is that binding of heparin to Opa facilitates fH (which possesses three heparin-binding domains (Zipfel et al. 1999)) adherence to surface bound C3. Support of this idea is that Chen et al. (1995) demonstrated that heparin treatment of gonococci resulted in a fifty-five to eighty-five percent increase in survival in normal human serum. fH has also been demonstrated to bind gonococcal porin. fH possesses a sialic acid binding site that has been shown to bind sialylated gonococcal LOS; consequently, the redundancy of the ability of fH to bind the gonococcus would preclude the absolute requirement for Opa proteins for successful infection by the gonococcus.

Membrane co-factor protein (CD46) serves as a C' regulatory protein on the surface of all nucleated cells thereby protecting them from C' mediated lysis. Similar to fH, CD46 functions on the cell surface as a co-factor for fI-mediated C' inactivation (Seya et al. 1990). CD46 has been shown to function as a receptor for gonococcus pili on unpolarized ME180 cells (Källström et al. 1997); however, in polarized epithelial cells CD46 exists on the basolateral surface (Maisner et al. 1997). Additionally, CD46 is not efficiently endocytosed and those surface molecules that are internalized are rapidly degraded (Maisner et al. 1997). These findings preclude the possibility of receptor recycling to the apical cell surface. The inventors' unpublished data and the work of others strongly suggests that gonococcal pili play a crucial role in gonococcal pathogenesis. A soluble form of CD46 (sCD46) also exists (Jurianz et al. 1999) and is present in seminal fluid (Vanderpuye et al. 1992); however, the significance of this molecule is unclear. In view of this work, its intriguing to speculate that the interaction of gonococcal pili with sCD46 may augment the function of CR3 possibly by binding to or near the divalent cation binding domain of CR3.

The presence of $Mn^{2+}$ and $Ca^{2+}$ are speculated to directly induce integrin changes required for efficient ligand binding by circumventing physiological triggering events (Altieri, D. C. 1991; Stewart et al. 1996; Violette et al. 1995). Kallstrom et al. (2000) recently demonstrated that adherence of non-piliated *N. gonorrhoeae* strain MS11 could be induced to occur on ME180 cells in the presence of $Ca^{2+}$. Although the inventors were unable to detect CR3 in any of the immortalized or malignant cell lines examined in this work (including ME180 cells), the $Ca^{2+}$-mediated invasion of non-piliated gonococci observed by Kallstom et al. might have occurred through an alternative integrin receptor. The cation-dependent induction of receptor function is a property attributed to integrins in general (Altieri, D. C. 1991).

SEM analysis demonstrated that the addition of anti-CR3 antibodies to CHO-CR3 and primary endo- and ectocervical cell monolayers resulted in membrane ruffles, suggesting that this phenomenon is elicited by CR3 activation. Upon gonococcal infection of primary human endo- and ectocervical cells membrane ruffling is induced to occur (Edwards et al. 2000). TEM analysis of clinical, cervical biopsies, which were derived from women with documented gonococcal cervicitis, suggested that membrane ruffling also occurred in vivo (Edwards et al. 2000). Additionally, membrane ruffling was predominately accompanied by a concentrated accumulation of the actin-associated proteins ezrin and vinculin (Edwards et al. 2000).

Jones et al. (1998) recently described two CR3 signaling pathways: 1) FcγR-induced, PI-3 kinase dependent and 2) formylmethionylleucylphenylalanine (fMLP)-induced, PI-3 kinase independent pathways. Both modes of CR3 signaling lead to the activation of p21 activating kinase 1 (PAK1) (Jones et al. 1998). PAK1 is a serine/threonine kinase demonstrated to exhibit multiple effector functions. PAK1 can regulate membrane ruffling both independently and dependently of the action of Rac (Obermeier et al. 1998; Sells 1997). Additionally, PAK1 regulates the formation of vinculin-containing focal complexes (Obermeier et al. 1998; Sells 1997). The ability of PAK1 to regulate membrane ruffling and vinculin accumulation through a CR3-dependent signaling cascade corresponds well with previously described data, and data presented herein. Additionally, this supports evidence for the induction of membrane ruffling of primary, human endo- and ectocervical cells by the binding of the gonococcus to CR3.

It is interesting to note that Shigella are capable of membrane ruffle induction and that these organisms parasitize the rectal epithelium (Tran Van Mhieu et al. 1999), which also exhibits CR3 expression (Hussain et al. 1995). Also of interest is that the sexually transmitted organisms, Candida and HIV, are both capable of CR3-mediated internalization of host cells (Cooper, N. R. 1991; Hussain et al. 1995; Würzner, R. 1999). The pathogenic Neisseria have evolved multiple efficient mechanisms by which to evade host defense mechanisms. Among these immune avoidance mechanisms are the strain-specific attributes that confer serum-resistance e.g., sialylation of some LOS glycoforms and a P.1A porin serotype (Densen, P. 1989; Ram et al. 1999; Vogel et al. 1999; et al. 1992). In vitro gonococcal infection studies and examination of clinically isolated gonococci have revealed C' components (predominately iC3b) on the surface of gonococci (Densen, P. 1989; Jarvis et al. 1999; McQuillen et al. 1999; Ross et al. 1985). Additionally, gonococci have been demonstrated to activate both the classical and alternative C' pathways; however, gonococcal killing primarily occurs via the CP (Densen et al. 1982). This would suggest a role for AP inactivation (and possibly subsequent CR3-mediated internalization) as one mechanism by which the gonococcus persists within its primary niche, the human reproductive tract. The inventors' data suggests that CR3-mediated invasion serves as a primary mechanism by which N. gonorrhoeae invades the cervical epithelium. This process involves ruffling of the cervical epithelium, which appears to be triggered by CR3 engagement.

Vaccine Preparations

The present invention thus provides a vaccine for use to protect mammals against Neisseria gonorrhoeae colonization or infection in women. For example, the vaccine may contain an immunogenic amount of polypeptide p177, p88, p64, p55 or p46 from N. gonorrhoeae, in combination with a physiologically-acceptable, non-toxic vehicle. Vaccines of the present invention can also include effective amounts of immunological adjuvants, known to enhance an immune response.

The neisserial protein can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin.

Further provided are isolated and purified nucleic acid molecules, e.g., DNA molecules, comprising a preselected nucleic acid segment that encodes at least a portion of a neisserial protein. For example, the invention provides an expression cassette comprising a preselected DNA segment that codes for an RNA molecule that is substantially identical (sense) to all or a portion of a messenger RNA ("target" mRNA), i.e., an endogenous or "native" neisserial protein mRNA. The preselected DNA segment in the expression cassette is operably linked to a promoter. As used herein, "substantially identical" in sequence means that two nucleic acid sequences have at least about 65%, preferably about 70%, more preferably about 90%, and even more preferably about 98%, contiguous nucleotide sequence identity to each other. Preferably, the preselected DNA segment hybridizes under hybridization conditions, preferably under stringent hybridization conditions, to a nucleic acid molecule encoding the corresponding native neisserial protein.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof As used herein, the term "derived" with respect to a RNA molecule means that the RNA molecule has complementary sequence identity to a particular DNA molecule.

Nucleic acid molecules encoding amino acid sequence variants of a neisserial protein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the neisserial protein.

To immunize a subject, the neisserial protein is administered parenterally, usually by intramuscular or subcutaneous injection in an appropriate vehicle. Other modes of administration, however, are also acceptable. For example, the vaccine may be administered orally, or via a mucosal route, such as a nasal, gastrointestinal or genital site. Vaccine formulations will contain an effective amount of the active ingredient in a vehicle. The effective amount is sufficient to prevent, ameliorate or reduce the incidence of *N. gonorrhoeae* colonization in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the human subject considered for vaccination. The quantity also depends upon the capacity of the person's immune system to synthesize antibodies, and the degree of protection desired. Effective dosages can be readily established by one of ordinary skill in the art through routine trials establishing dose response curves. The subject is immunized by administration of the neisserial protein in one or more doses. Multiple doses may be administered as is required to maintain a state of immunity to streptococci.

To prepare a vaccine, the purified neisserial protein can be isolated, lyophilized and stabilized. The neisserial protein may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

Antibodies

The antibodies of the invention are prepared by using standard techniques. To prepare polyclonal antibodies or "antisera," an animal is inoculated with an antigen, i.e., a purified immunogenic CR3 peptide or polypeptide, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies against CR3.

Following immunization, Ig is purified from the immunized bird or mammal, e.g., goat, rabbit, mouse, rat, or donkey and the like. For certain applications particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to CR3, or peptides thereof. Antibodies can be purified by affinity chromatography, using purified CR3, or peptides thereof. Purification of antibodies by affinity chromatography is generally known to those skilled in the art (see, for example, U.S. Pat. No. 4,533,630). Briefly, the purified antibody is contacted with the purified CR3, or peptide thereof, bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the $F_{(ab)}$ fragment scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments that retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

Inhibitory Compounds

The present invention provides a method of preventing entry of *Neisseria gonorrhoeae* into a cell (or treating an existing infection) by administering a compound that binds to a CR3 receptor on the cell. In particular, it has been discovered that it is possible to prevent the infection of cervical cells (endocervical or ectocervical cells) by blocking the access of *N gonorrhoeae* to the CR3 receptor on the surface of the cell. Any inhibitor could be used. The inhibitor could be an antibody (e.g., a monoclonal or polyclonal antibody, or a fragment of an antibody). Alternatively, the compound could be peptide, as discussed in detail in Example 3 below. For example the compound could be a *Clostridium* neurotoxin, such as the *Clostridium* C3 neurotoxin. The compound could be Clostridium neurotoxin type 3, Cytochalsin D, wortmannin, an anion channel blocker, a divalent cation chelator (such as EDTA or EGTA), inhibitors of serine/threonine proteases, and/or LY294002.

Formulations of Compounds and Methods of Administration

In cases where compounds are sufficiently basic or acidic to form stable nontoxic acid or base salts, Administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

The compounds may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples are intended to illustrate but not limit the invention.

EXAMPLE 1

Membrane Ruffling and Cytoskeletal Rearrangements in *Neisseria gonorrhoeae*

The sexually transmitted pathogen *Neisseria gonorrhoeae*, the causative agent in gonorrhea, can infect the male and female genital tract. Studies have shown that the organism can discriminate between the sexes and uses different mechanisms for infection of men than for infection of women. During the course of female infection, it appears that the organism releases a group of proteins that initiate a process called membrane ruffling on endocervical and exocervical epithelial cells. Organisms adherent to or proximal to the ruffled area invade the epithelial cell. The gonococcus can proliferate within the intracellular environment, cause the death of the infected cell and are released. They re-enter new cells and the cycle continues until an inflammatory response ensues or the organisms spreads to the endometrium and fallopian tubes.

Bacteria: *N. gonorrhoeae* strains 1291, 1291-green (1291 expressing green fluorescent protein and to be described elsewhere, the plasmid pLES98 was a gift from V. Clark), FA1090, MS11-A, and MS11$_{mk}$C were used in these infection studies. These strains are $P^+$ and $Opa^+$. Strains 1291, 1291-green, MS11-A, and MS11$_{mk}$C contain the pathogenicity island recently described by Dillard (Dillard, J. 1999).

Development of Primary Cervical Cell Culture Systems: Surgical biopsies were obtained from 30 pre-menopausal women undergoing hysterectomy at the University of Iowa Hospitals and Clinics (Iowa City, Iowa). Endocervical (proximal to the cervical os) and ectocervical (distal to the cervical os) tissue biopsies were obtained in 4-6 mm$^2$ sections and further subdivided into 2-3 mm$^2$ sections. Sectioned tissues were rinsed twice for 10 min in Hanks Balanced Salt Solution (HBSS) supplemented with 1% fungizone (Irvine Scientific, Santa Ana, Calif.) and 1% penicillin (100 U/ml)-streptomycin (1 mg/ml). The tissue was placed with the epithelium downward on polystyrene, 35 mm tissue culture dishes (Falcon, Becton Dickinson; Franklin Lake, N.J.). Tissue explants were incubated in filtered airway medium (1 part Dulbecco Modified Eagle Medium, 1 part Ham's F12, 5% fetal calf serum (FCS), 1% nonessential amino acids (Sigma-Aldrich, St. Louis, Mo.), 1% penicillin-streptomycin, and insulin (10 g/ml)). After 48 h, airway medium was replaced with keratinocyte growth medium (KGM)-2 Bullet Kit (Clonetics, San Diego, Calif.). KGM-2 was replaced every 2-3 days until near-confluence was obtained (1-2 weeks) at which time the cells were passaged as outlined below. Although variability exists among tissue samples, this process allows for an average of three passages of cell growth to fresh tissue culture dishes from a single tissue explant prior to fibroblast development, at which time tissue explants were discarded.

Cell Passage: At near-confluent growth cells were passaged by a 5 min, 37° C. incubation in HBSS-0.25% Trypsin-0.1% EDTA. Cell suspensions were collected and centrifuged at 5000 rpm for 5 min. The resulting cell pellet was rinsed in HBSS, resuspended in KGM-2, and used to seed transwell membrane systems (Biocoat Cell Environments, Becton Dickinson, Bedford, Mass.) (to allow for polarized cell growth); glass, 8-well chamber slides (Nalge Nunc International, Naperville, Ill.); or human, placental collagen-coated, 12 mm glass coverslips previously placed in 24-well tissue culture dishes (Falcon). Primary cervical cells were maintained in KGM-2 until near-confluence was again obtained at which time they were infected with *N. gonorrhoeae* as outlined below. Where applicable, cellular polarity was determined as an electrical resistance greater than $2K\Omega/cm^2$ as measured across the cell monolayer. Infected and uninfected (i.e., control) cervical cell-harboring membranes (from transwell systems) were subsequently subdivided into equal sections. Sections to be used for scanning electron microscopy (SEM) were processed while attached to the well apparatus so that the cellular orientation would be maintained. Remaining sections were removed from the well structure and subsequently processed independently for either confocal, transmission electron, or bright-field light microscopy.

Infection of the Primary Cells: *N. gonorrhoeae* cells allowed to grow overnight (37° C., 5% $CO_2$) on GC-IsoVitaleX agar plates were harvested using a sterile swab and resuspended in sterile saline. Culture density was determined spectrophotometrically where an optical density (OD) of 1 at 600 nm was equivalent to $10^9$ bacteria $ml^{-1}$ of cell culture. Bacterial cells were then diluted to a concentration of $10^7$ bacteria $ml^{-1}$ in KGM-2 lacking gentamycin and used to infect $10^5$ primary cervical cells (maintained as outlined above). Gonococcal infection was allowed to progress for variable time periods after which the infection was stopped by the removal of the infection medium, rinsing infected cervical cells with phosphate buffered saline (PBS), and cell fixation. Samples to be used in laser scanning confocal microscopy (LSCM) or differential interference contrast (DIC) analysis were immunolabeled directly following fixation. SEM, transmission electron microscopy (TEM), and bright field light microscopy (BFLM) samples were further processed by graded ethanol dehydration and resin (TEM) or paraffin (BFLM) embedment. Embedded samples were sectioned and immunolabeled as noted. Where indicated, the infection medium was harvested from the cervical cell monolayer and reused to infect fresh, uninfected cell cultures, which were subsequently processed for SEM analysis.

Invasion Assays in the Presence of Inhibitors of Cytoskeletal Motility and Protein Synthesis: Cervical cells were passed to 12 mm collagen-coated coverslips as outlined above. Prior to infection with *N. gonorrhoeae* 1291 wild-type cells, primary cell cultures were left untreated, or they were pre-incubated with 300 nM wortmannin (Sigma), 1 M cytochalasin D (Sigma), or 400 mM ethylene glycol bis-(2-aminoethyl ether)-N,N, N', N'tetraacetic acid ((EGTA) Amresco, Solon, Ohio) for 2 h, 30 min, and 30 min, respectively, or they were pretreated with 100 g/ml nocodazole (Calbiochem-Novabiochem Corp., La Jolla, Calif.) for 1 h at 4° C. followed by a 30 min incubation at 37° C. The requirement for de novo protein synthesis, either by the bacteria or by the primary cervical cells, was tested by pretreatment (30 min, 37° C.) of the bacterial cultures or cervical cell monolayers with 4 g/ml chloramphenicol (Sigma) or 25 mM cycloheximide (Calbiochem-Novabiochem Corp.), respectively. All chemical reagents used were maintained in the infection medium throughout the course of the infection. Trypan blue exclusion revealed no significant toxicity to the primary cervical cells at the indicated concentrations for each of the chemical reagents used. Infection was allowed to progress at 37° C., 5% $CO_2$, for 1.5 h after which the medium was removed, the cells were rinsed with PBS, and then incubated with KGM-2 containing 100 g/ml gentamycin to kill extracellular bacteria. Post incubation the cervical cells were lysed with 0.5% saponin to release invasive bacteria. Percent invasion was determined as a function of the original inoculum and the number of colonies formed with subsequent plating of the cellular lysate. A Kruskal-Wallace ANOVA was used to determine the statistical significance of the calculated percent invasion for each of the cytoskeletal motility inhibitors used with respect to the untreated, infected cell cultures.

Microscopy: Samples were processed for LSCM, SEM, or TEM as previously described (Ketterer et al. 1999). Samples to be analyzed by BFLM were paraffin embedded using an automated tissue processor (RMC 1530 Paraffin Tissue Processor, Tucson, Ariz.), cut into thick (1 m) sections, and mounted onto glass microscope slides. Immunolabeling of infected and uninfected cervical cells for TEM analysis was performed using the monoclonal antibody 2C3, which specifically recognizes the H.8 gonococcal surface protein, or the anti-gonococcal porin monoclonal antibody, 3H1 (a gift from Mylan Blake); in conjunction with a polyclonal antibody to filamentous (F) actin. Secondary labeling proceeded with the use of 30 nm and 10 nm colloidal gold-beaded antibody conjugates (Amersham Pharmacia Biotech, Piscataway, N.J.) to the bacterial- and actin-specific antibodies, respectively. B. A. Evans generously provided clinical biopsies used in TEM analysis. The samples were viewed with an H-7000 Hitachi Transmission Electron Microscope (Hitachi Corporation, Mountain View, Calif.).

Primary antibodies used for LSCM or DIC microscopy were as follows: anti-cytokeratin 8.12 (Sigma), -cytokeratin 4 (Sigma), -talin (Sigma), -vinculin (Sigma), -α-actinin (Sigma), -myosin (Sigma), -ezrin (Santa Cruz Biotechnology, Santa Cruz, Calif.), -CD66 (DAKO, Carpinteria, Calif.), -CD46 (Santa Cruz Biotechnology), and 2C3. Immunolabeling of cervical cell monolayers with anti-cytokeratin, -talin, -vinculin, -myosin, -ezrin, and -α-actinin occurred subsequent to a 15 min incubation in 0.2% Triton X-100 to allow cervical cells to become permeable. Where indicated, counter staining occurred at room temperature (RT) for 6 min. Counter stains used were specific for nucleic acids and consisted of YOYO-1 (Molecular Probes, Eugene, Oreg.) or ethidium bromide. Samples were viewed using the BioRad MRC-1024 or the Zeiss 510 Laser Scanning Confocal viewing systems.

Cervical tissue biopsies (obtained as outlined above) to be used for LSCM cytokeratin analysis were processed (within 1-2 h of obtaining the tissue specimen) for cyrosectioning by a 30 min incubation in 1% paraformaldehyde followed by infiltration with 30% sucrose prior to embedment in Tissue-Tek O. C. T. compound (Sakura Finetek USA, Inc., Torrance, Calif.) and sectioning (6-8 nm). Frozen sections were allowed to stand at RT for 1 h prior to immunolabeling with the indicated anti-cytokeratin antibody. A fluoroscein isothiocyanate (FITC)-conjugated secondary antibody was applied and tissues were subsequently counter-stained with ethidium bromide (0.5 ng/ml, 6 min).

Cervical cells passaged to 12 mm coverslips were used to assay for gonococcal-induced macropinocytosis. Cervical cell monolayers were infected with 1291-green for variable time periods in the presence of 1 mg/ml tetramethylrhodamine B isothiocyanate (TRITC)-dextran (MW 150, 000). Infection was stopped by the removal of the infection medium. Infected monolayers were extensively washed prior to fixation with 2% paraformaldehyde. Coverslips were mounted onto glass microscope slides and viewed using the BioRad MRC-1024 Laser Scanning Confocal viewing system.

Slides prepared for BFLM were hematoxylin-eosin stained using a standard protocol and viewed with a Leitz Diaplan microscope with an Optronics Engineering viewing system. SEM analysis was performed using an H-4000 Hitachi Scanning Electron Microscope (Hitachi).

Results

Characterization of Primary Human Endocervical Epithelial Cells: Primary cervical epithelial cells were allowed to grow as described above. Epithelial cells could be seen extending from the cervical explants within two to three days from the start of the cultures. Growth radiated from the tissue foci in a contiguous monolayer, and confluence was observed within ten to fourteen days. Transfer of endocervical-derived cells to transwell membrane systems resulted in polarized cell growth.

Figure 4:
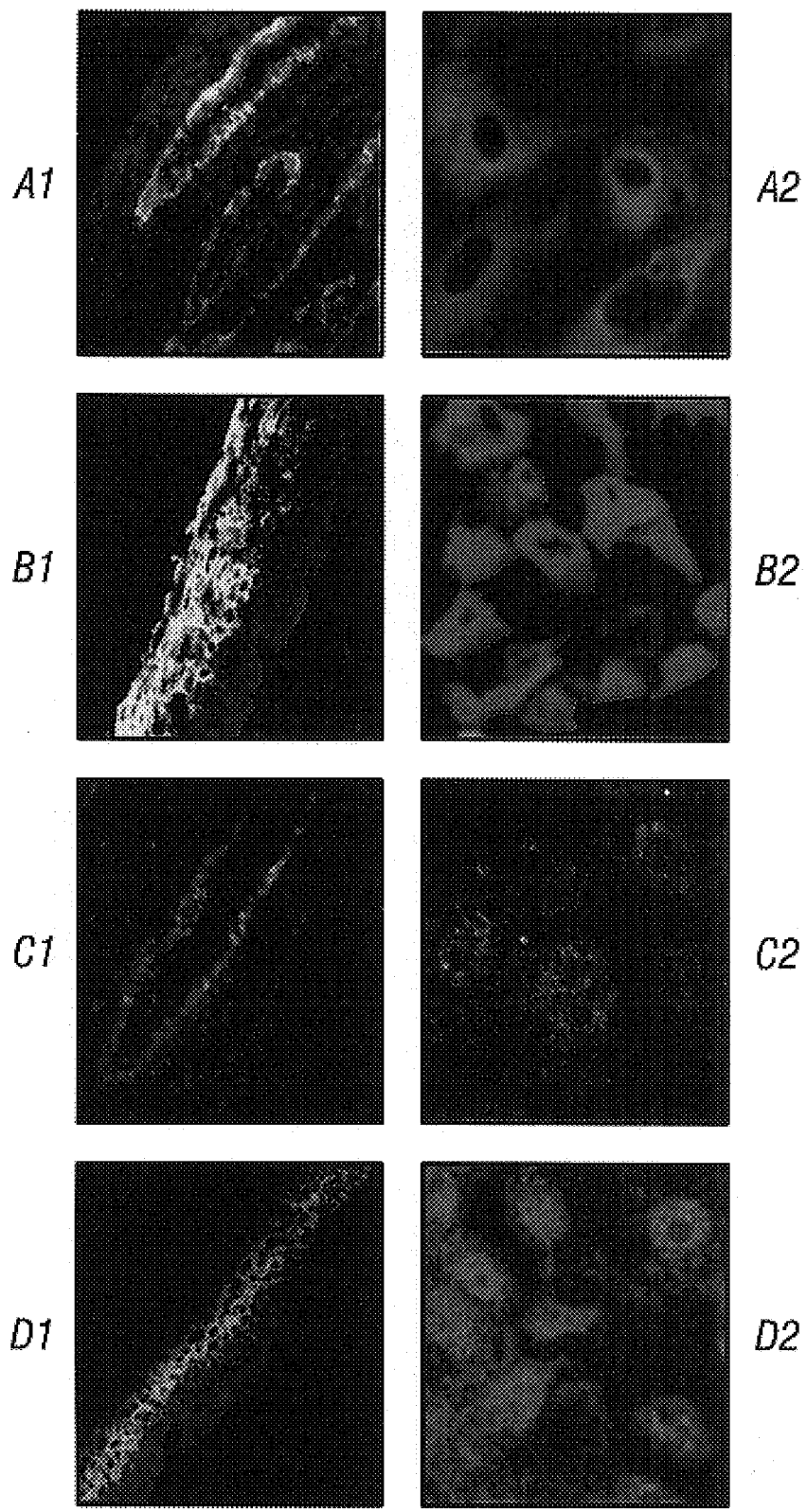

The cytokeratin expression pattern of the normal human uterine cervix has been well characterized. LSCM was used to determine the cytokeratin expression pattern of the primary cervical cell monolayers with respect to the tissue from which they were derived. Sectioned tissue biopsies (obtained from the endo- and ectocervix) and the cervical-derived cell monolayers were immunohistochemically examined with antibodies to cytokeratins 4, 13, 15, and 16. The results of these studies can be seen in FIG. 4. The specific cytokeratin staining character of the endo- and ectocervical tissue was retained in the primary cell monolayers (FIG. 4).

LSCM analysis of sectioned tissue biopsies and cervical-derived cell monolayers demonstrated the expression of CD66 and CD46 in both the endo- and ectocervix.

Figure 5A:
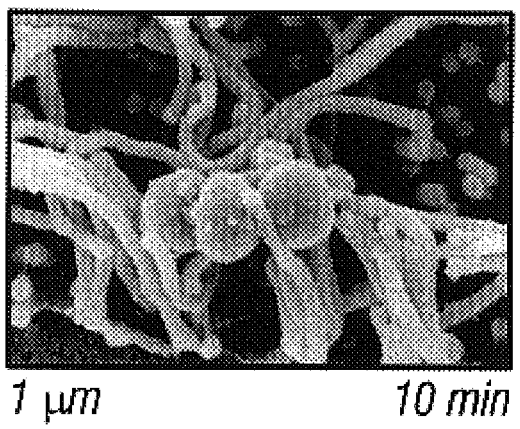
Figure 5B:
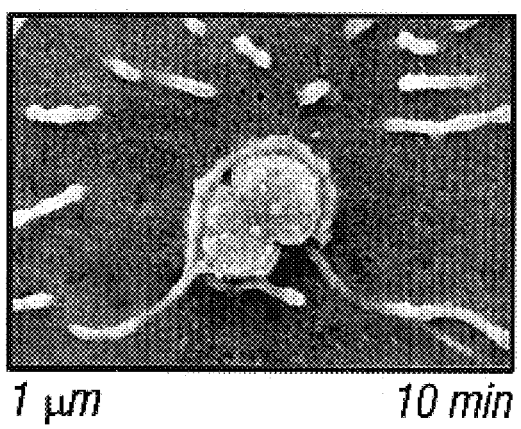
Figure 5C:
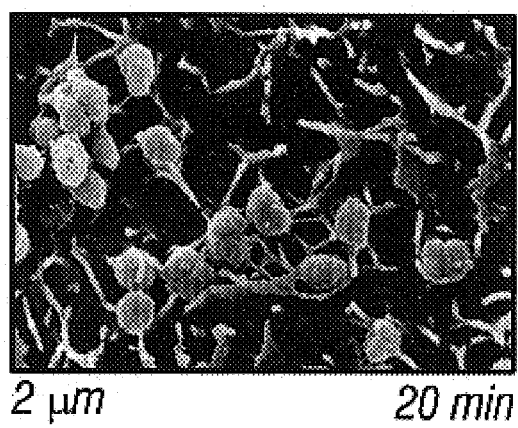
Figure 5D:
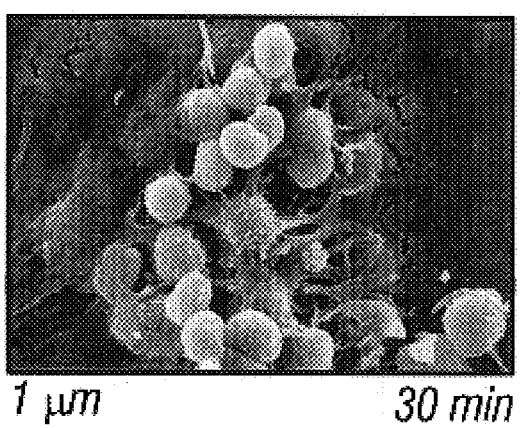
Figure 5E:
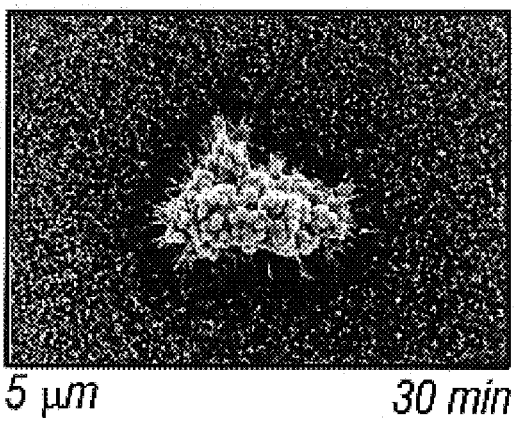
Figure 5F:
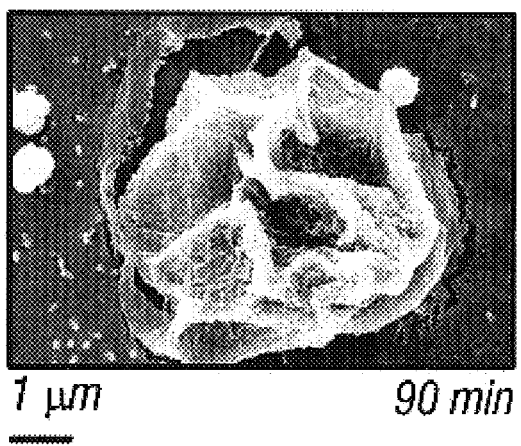
Figure 5G:
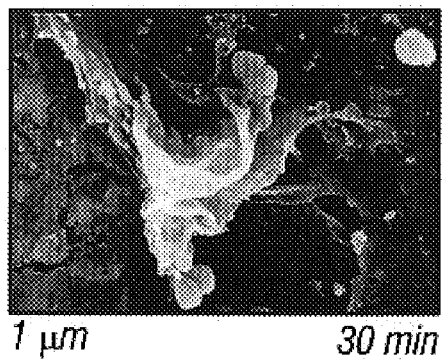
Figure 5H:
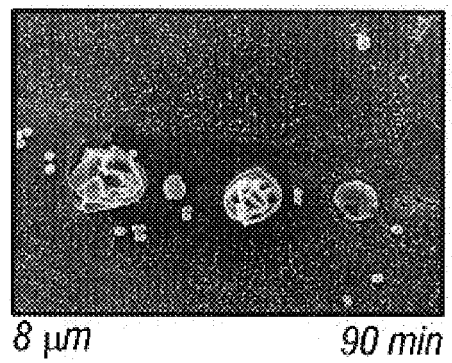
Figure 6A:
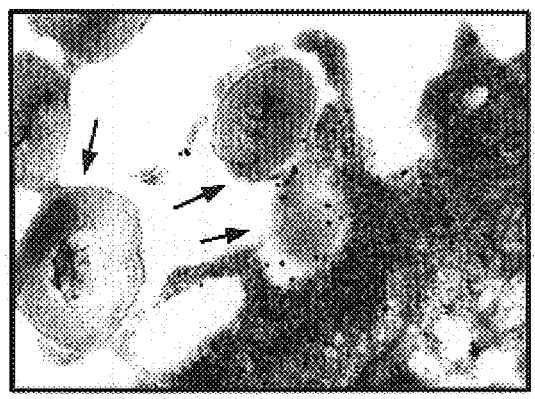
Figure 6B:
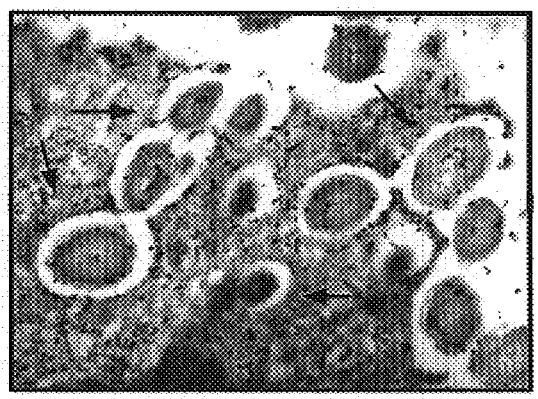
Figure 6C:
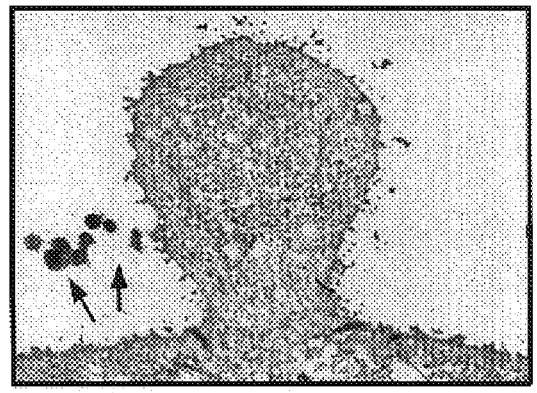
Figure 6D:
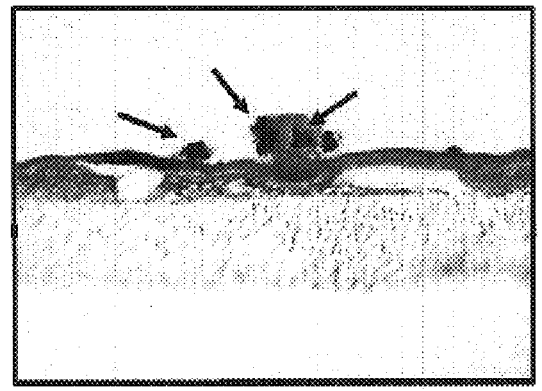

*N. gonorrhoeae* Infection of Primary Cervical Epithelial Cells: SEM analysis of *N. gonorrhoeae* 1291 infected polarized and non-polarized cells showed bacteria could adhere to both types of primary cervical cells. Bacteria were found distributed across the monolayer surface. The interaction of the bacteria with the cervical cell surface appeared to occur by multiple mechanisms. At approximately ten minutes post infection gonococci could be found associated with the cervical cell membrane both dependent (FIG. 5A) and independent of microvilli (FIG. 5B). Small tufts of microvilli were associated with bacteria on some cervical cells. Gonococci associated with the cervical cells independent of microvilli appeared to be entering the cervical cell by an endocytic process. At approximately 20 and 30 minutes post-infection, filopodia and lamellipodia formation was readily observed (FIG. 5C) and bacteria appeared to be undergoing internalization (FIG. 5D). Additionally, a visible smoothing of the cervical cell membrane was evident around the periphery of some sites of bacterial infection (FIG. 5E). By 60 minutes post-infection, the filopodia and lamellipodia became less prominent. Large membrane ruffles (FIGS. 5F and 5G) became prominent at about 90 minutes post infection of cervical cells. Membrane ruffles were abutting and contiguous with gonococci. Generally, ruffles could be readily identified by a smoothing of the cervical cell membrane that encircled the ruffle (FIG. 5H). At 3 h post-gonococcal infection, membrane ruffles and bacteria associated with microvilli were still evident. Perturbations of the cell membrane that were reminiscent of ruffles were also evident. Ruffling could be induced to occur at approximately thirty minutes post-gonococcal infection in both primary cell systems when uninfected cervical cells were infected with a primed infection inoculum (i.e., infection medium transferred from an immediately prior *N. gonorrhoeae* cervical cell infection) derived from one hour (ectocervical) (FIG. 5G) and ninety minute (endocervical) infections.

Figure 7A:
Figure 7B:
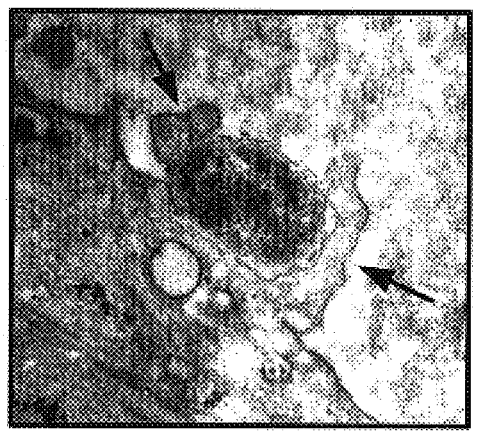
Figure 8A:
Figure 8B:
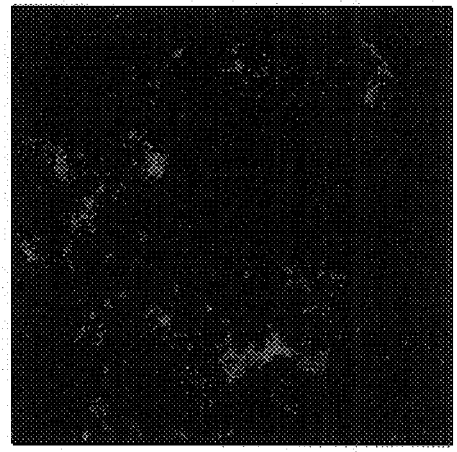
Figure 8C:
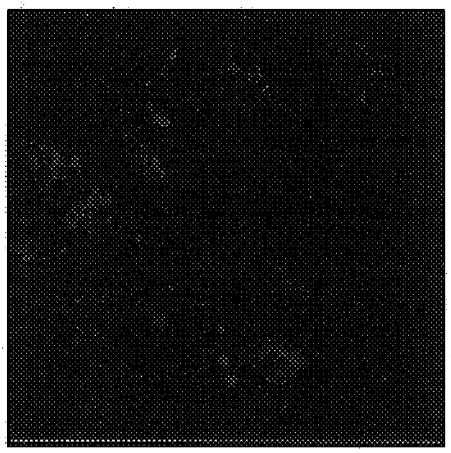
Figure 8D:
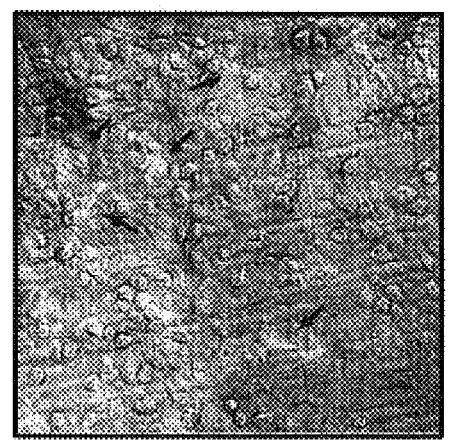

Bright-field light microscopy and TEM analysis of polarized endocervical cells infected with *N. gonorrhoeae* 1291 confirmed the observation made with SEM analysis (FIG. 6). Actin-filled membrane protrusions were readily observed encompassing gonococci at ninety minutes and three hours post infection. Clusters of bacteria were found breaching the superficial cervical epithelial layer; however, bacteria entered the cervical cells as single entities with each bacterium being surrounded by its own actin-lined vacuole (FIG. 6B). Consistent with SEM analysis, gonococcus-associated membrane ruffles were readily observed at 3 h post-infection by both high-powered (TEM, FIG. 6C) and low-powered (BFLM, FIG. 6D) magnification with microscopy. TEM analysis revealed that, within the host cell cytoplasm, bacteria-containing vacuoles appeared to coalesce prior to bacterial exocytosis to the subepithelial space. TEM analysis of epon-embedded, clinically-derived cervical biopsies from women naturally infected with gonococci revealed similar processes (FIG. 7). Large membrane protrusions (indicative of ruffles) (FIG. 7B) and smaller, less organized membrane structures (FIG. 7A), were readily observed. Gonococci were, again, observed to enter the cervical cells as single entities in spacious vacuoles.

Primary cell monolayers infected with gonococci in the presence of a TRITC-conjugated dextran, which would be excluded by non-macropinocytic cellular events, demonstrated that, upon invasion, gonococci reside within macropinosomes.

LSCM analysis of infection studies performed using polarized endocervical cells and ectocervical cell monolayers suggested co-localization of CD66 and CD46 with gonococci. With extended infection (i.e., six hours) clustering of CD46 molecules, which was not observed to occur at earlier time points in the infection, became prevalent in response to gonococci.

Cytoskeletal Changes Occur in Cervical Cells with Gonococcal Infection: Immunolabeling of *N. gonorrhoeae* infected primary cells with antibody-conjugates to actin-associated proteins confirmed that changes of the cervical cell cytoskeletal network were occurring (FIG. 8). Antibodies to talin, vinculin, ezrin, myosin, and α-actinin demonstrated a focused accumulation of these proteins, in membrane projections, at ten minutes post infection with gonococci. Membrane projections were also observed to co-localize with gonococci. This effect was most pronounced with the use of vinculin and ezrin; however, a modest accumulation of talin and α-actinin was also observed to occur. Immunolabeled projections were not observed upon analysis of uninfected cervical cells.

Gonococcal Invasion of Cervical Cells Occurs Primarily in an Actin-Dependent Manner and Does Not Require de novo Protein Synthesis: Standard gentamycin-resistance assays performed with endo- and ectocervical-derived cells confirmed results obtained by BFLM and TEM analysis and the invasive nature of gonococci with respect to both the endo- and ectocervix. Gonococci were found to invade endocervical-derived cells at a proportion of 1.57% (table 1). A slightly higher percentage (2.70%) was observed to occur with gonococcal invasion of the ectocervical-derived cells (table 1). The inclusion of wortmannin, cytochalasin D, and EGTA in the invasion assay prohibited bacterial entry into both cell types (table 1). Pretreatment of primary cervical cell monolayers with the microtubule-specific depolymerizing agent, nocodazole, resulted in an approximate 67% decrease in gonococcal invasion (table 1). Chloramphenicol and cycloheximide, which inhibit gonococcal and eukaryotic cell protein synthesis (respectively), did not inhibit gonococcal invasion of the primary cervical cell monolayers (table 1).

TABLE 1

Percent invasion of N. gonorrhoeae 1291 in primary cervical cells

| Cell treatment | Endocervical cells | | | Ectocervical cells | | |
|---|---|---|---|---|---|---|
| | Mean % invasion[a] | Variance of the mean | p[b] | Mean % invasion[a] | Variance of the mean | p[b] |
| None | 1.5517 | 0.3030 | NA[c] | 2.6953 | 1.3569 | NA |
| Cytochalasin D | 0.0358 | 0.0186 | 0.05 | 0.0233 | 0.0046 | 0.025 |
| Wortmannin | 0.0177 | 0.0180 | 0.05 | 0.0260 | 0.0158 | 0.025 |
| EGTA | 0.0431 | 0.0087 | 0.05 | 0.0303 | 0.0052 | 0.025 |
| Nocodazole | ND[d] | ND | ND | 0.9000 | 0.7906 | 0.25 |
| Cycloheximide | ND | ND | ND | 2.5601 | 1.8816 | 0.75 |
| Chloramphenicol | ND | ND | ND | 2.6688 | 1.9590 | 0.50 |

[a]The mean is the average percentage of at least three trials in which the percent invasion was determined as a function of the original inoculum and the subsequent CFU.
[b]P values given were determined using a Kruskal-Wallis κ-sample test of the percent gonococcal invasion determined for each cellular treatment applied to primary cervical cells in comparison to the percent gonococcal invasion of untreated, primary cervical cells.
[c]NA, not applicable.
[d]ND, not determined.

Discussion

Primary human ecto- and endocervical epithelial cell models have been described whose cytokeratin, CD66, and CD46 profiles are identical to the tissue from which they were derived. Confocal and electron microscopic analysis of primary, human, cervical cells infected with N. gonorrhoeae 1291, FA1090, and MS11 have demonstrated the ability of gonococci to adhere to and to induce cytoskeletal changes within both of these cell systems. Bacteria were found to associate with the primary cervical cells by more than one mechanism as evidenced by microvillus-dependent and -independent modes of bacterial attachment. Membrane perturbations resulted in the formation of membrane ruffles, which became prominent by ninety minutes post infection and after which ruffles remained readily observable. Ruffling could be induced to occur at thirty minutes post gonococcal infection in both primary cell systems when uninfected cervical cells were infected with a primed infection inoculum; however, de novo protein synthesis was not required to prime the infection process for invasion. Actin-associated proteins were also observed to accumulate in response to gonococcal infection. Gonococci were found to be internalized within the cervical cells in actin-lined spacious vacuoles.

The ability of gonococci to attach to the endocervical epithelium is well accepted. In contrast, attachment to the stratified squamous epithelium of the ectocervix and to transitional cells of the cervical squamocolumnar junction (Draper et al. 1980; Evans, B. A. 1977) remains controversial. Studies, in vitro, with the inventors' primary cell culture systems demonstrated gonococcal adherence to both the endo- and ectocervix. Considerable anatomical variation exists in the length of the squamocolumnar transition zone of the cervix (Fluhmann, C. F. 1959). Additionally, to a variable measure, columnar epithelium may overlap the stratified squamous epithelium (of the ectocervix) at the transition zone. This may, in part, account for the controversy associated with gonococcal attachment to the cervical epithelium. Cervical biopsies, used in the studies described herein, were obtained from sites distinct from the transformation zone i.e., greater than 0.5 cm from the squamocolumnar junction. Of the thirty cervical specimens used to generate primary cell cultures for use in these studies, all have supported gonococcal adherence with minimal variability. Gonococcal adherence, to date, has primarily been associated with microvilli formation; however, gonococci associated with the cervical epithelium were found both dependent and independent of microvilli.

Attachment is not synonymous with tissue damage or with the initiation of a diseased state; it is a discrete event from phagocytic internalization i.e., invasion. Four general mechanisms of bacterial invasion of host cells have been proposed to occur: receptor mediated endocytosis (Robinson, M. S. 1994), microtubule-dependent endocytosis (Mukherjee et al. 1997; Oelschlager et al. 1993; Silverstein et al. 1977), zippering (Griffin, Jr., et al. 1976; Griffin, Jr., et al. 1975), and triggering (Dramsi et al. 1998; Finlay et al. 1997; Moulder, J. W. 1985; Rabinovitch, M. 1995; Watarai et al. 1996). Several eukaryotic cell surface molecules have been proposed to serve as receptors for gonococcal invasion (for review Dehio et al. 1998; Dramsi et al. 1998; Jerse et al. 1997; McGee et al. 1983; Meyer, T. F. 1999; Nassif et al. 1999; Nassif et al. 1995; Naumann et al. 1999). In fallopian tube organ culture (FTOC) gonococcal invasion has been proposed to occur in a manner reminiscent of "zipper" type phagocytosis. (Dramsi et al. 1998; McGee et al. 1983; Stephens, D. S. 1989).

The observation that gonococci appear to induce membrane ruffling is a novel finding. Ruffling is the result of a complex interaction that occurs between a bacterium and a host cell and is associated with a triggering mechanism (Silverstein et al. 1977) that leads to macropinocytosis (Alpuche-Aranda et al., 1994; Francis et al. 1993; Garcia-del Portiilo et al. 1994; Swanson et al. 1995). Infection of the inventors' primary cell culture systems resulted in ruffling of both the endo- and ectocervical-derived cells. Ruffling was evident in the endocervical cells as convoluted spheres whereas ruffling of the ectocervical cells was observed to occur as long, ribbon-like folds. The characteristic structural morphology of endo- and ectocervical-associated ruffles appeared to be specific for each of their respective cell types; hence, the ruffles found on the ectocervical cells were termed "ribbons."

Salmonella and Shigella have been shown to induce membrane ruffling in a contact-dependent manner in which a (highly conserved) type III secretion system (TTSS) allows for the secretion of numerous effector proteins that initiate the cellular response required for the observed cytoskeletal rearrangements (Finlay et al. 1991; Rosqvist et al. 1995; Tran Van Mhieu et al. 1999). A TTSS has not been described for N. gonorrhoeae. A search of the N. gonorrhoeae strain FA 1090 genome data base (University of Oklahoma Advanced Center for Genome Technology) for the possible existence of Salmonella and Shigella TTSS and effector protein homologs yielded no significant matches to ruffling-associated proteins. Dillard et al. (1999) recently described the existence of a pathogenicity island in N. gonorrhoeae strain MS11, which encodes a secretion system. This pathogenicity island is also present in N. gonorrhoeae strain 1291, but it is absent in N. gonorrhoeae strain FA 1090. This pathogenicity island (and its encoded secretion system) may, therefore, share homology to Salmonella and Shigella TTSS and effector proteins; however, this data is currently unavailable.

Ruffling and subsequent invasion by Salmonella and Shigella shows an actin-dependence but occurs independent of microtubules. It has previously been demonstrated that gonococcal invasion of tissue culture cell lines is dependent upon microtubules and a functional actin cytoskeleton (Bessen et al. 1986; Grassme et al. 1996; Richardson et al. 1998). Using standard gentamycin-resistance assays endo- and ectocervical cells were examined to determine if these primary cells displayed a microtubule- or actin-dependence for gonococcal invasion. Cytochalasin D, wortmannin, and EGTA brought invasion levels down to (essentially) zero in both cell systems suggesting that gonococcal entry is dependent upon actin rearrangements. TEM analysis of *N. gonorrhoeae* infected polarized cervical cells supported a role for actin in the gonococcal invasion process in that actin-filled ruffles and large, spacious, actin-lined vacuoles encompassed invading gonococci. The latter finding is in contrast to Grassme et al. (1996) who demonstrated that gonococcal association with actin was transient. In multiple experiments, using cervical cell monolayers derived from different patients, invasion was not significantly inhibited when primary cervical cells were pretreated with nocadazole to disrupt microtubules.

A concentrated accumulation of actin-associated proteins has been demonstrated to occur in response to membrane ruffling (Clerc et al. 1987; Finlay et al 1991; Skoudy et al. 1999). To the knowledge of the present inventors, the role of actin-associated proteins in gonococcal infection has not been examined. It was found that in response to gonococcal invasion a concentrated accumulation of predominately ezrin and vinculin occurs in a manner analogous to *Shigella*. A modest accumulation of talin and α-actinin also was observed during gonococcal infection of cervical cells. Additionally, although myosin was observed to accumulate in response to, and co-localize with, gonococci at five and ten minutes post infection, myosin was also observed to be fairly diffuse throughout some of the infected cervical cells. This may reflect the relative abundance of this protein in comparison to the other actin-associated proteins that were examined. Alternatively, the observed myosin distribution may be indicative of the initiation of a concurrent change occurring in the actin cytoskeleton, or it is possible that gonococci elicit only a minimal recruitment of myosin upon ruffle induction.

The host cell surface molecule exploited by *Salmonella* to initiate ruffling has, to date, not been elucidated. The *Shigella* protein complex of IpaB/C/D has been shown to bind the fibronectin receptor, integrin $\alpha_5\beta_1$ (Watarai et al. 1996). The predominant accumulation of ezrin and vinculin in *N. gonorrhoeae* infected primary cervical cells and the ability of these actin-associated proteins to directly interact with integrin molecules to initiate cellular responses (Clarke et al. 1977; Schmidt et al. 1998) make integrin molecules attractive candidates as potential gonococcal receptors that serve to initiate gonococcal-induced ruffling. Studies using the larynx carcinoma cell line, HEp-2, have demonstrated that gonococcal binding of fibronectin results in co-ligation of heparan sulphate proteoglycan (HSPG) to gonococcal Opa proteins and subsequent binding to the $\alpha_5\beta_1$ integrin (Naumann et al. 1999). Ruffling was not observed to occur in these cells suggesting that gonococcal induction of ruffles may be unique to the cervical epithelium. Investigation of male primary urethral cells has shown that some gonococci can enter these cells by focal macropinocytosis, but no evidence of ruffling was seen. This would suggest that perhaps a cell surface molecule unique to the cervical epithelium may be involved in ruffle induction and that gonococci invoke membrane ruffles by a mechanism distinct from that observed for *Shigella*. *Salmonella* and *Shigella* share many common characteristics with respect to their ability to induce membrane ruffles; however, they each also display ruffling characteristics that are unique to their genus.

Through co-evolution with their exclusive human hosts the pathogenic *Neisseria* have developed several mechanisms by which they successfully persist in the general population. Previous studies of *N. gonorrhoeae* have demonstrated the ability of these organisms to invade eukaryotic cells by receptor-mediated endocytosis, microtubule-dependent endocytosis, and zippering. Here yet another mechanism by which gonococci are able to exploit their human host is described. Ruffling, via a triggering mechanism, has not been observed to occur in male primary urethral cells, tissue culture cell lines, or FTOC nor has ruffling been described to occur with *Neisseria meningiditis* infections. Ruffling of primary cervical cells, which is induced with gonococcal infection, therefore, is a novel finding.

EXAMPLE 2

Complement Receptor 3 (CR3) is the Factor Responsible for Ruffling

Tissues and Cell Culture. Surgical biopsies derived from the endo- and the ectocervix that were used to seed primary cervical epithelial cell systems were procured and maintained as described (Example 1 above) in Defined Keratinocyte Serum Free Medium (dk-SFM) (Life Technologies, Rockville, Md.). Urethra epithelia was obtained from adult males undergoing urologic surgery at the University of Iowa Hospitals and Clinics and used to seed primary urethral cell culture systems as described by Harvey et al. (1997). Primary male urethral cells were immortalized with the E6 and E7 genes from the Human Papilloma Virus prior to use. E6E7 immortalized human ectocervical keratinocytes (HCK) and endocervical (End1) cells (generously provided by A. Klinglehutz (University of Iowa, Iowa City, Iowa) and D. Anderson (Fearing Research Laboratory, Boston, Mass.), respectively) were cultured in dk-SFM. ME180 cervical carcinoma cells (ATCC # HTB-33) were cultured in McCoy's 5A medium (Life Technologies) according to ATCC recommendations. Hec1B endometrial carcinoma cells, Chinese hamster ovary cells (CHO-K1), and K562 myeloid cells were maintained in RPMI tissue culture medium (Life Technologies). CR3-expressing CHO(CHO-CR3) and K562 (K562-CR3) cells were maintained in RPMI-G418 (100 μg/ml). CHO cells were generously provided by L. A. Allen and L. Schlsinger (University of Iowa) with permission from D. Golenbock (Boston Medical Center, Boston, Mass.). E. Brown (University of Calif., San Francisco, Calif.) generously provided K562 and K562-CR3 cells. McCoy's 5A and RPMI media were replaced with dk-SFM 48 h prior to infection studies. Surgical biopsies derived from the fallopian tube, endometrium, endocervix, ectocervix, vas deferens, and the male and the female urethra that were to be used for immunohistochemical tissue analysis were processed for cryosectioning as previously described in Example 1 above. Clinical biopsies derived from the cervix of women with documented gonorrhea were provided by D. Fortenberry (Indiana University School of Medicine, Indianapolis, Ind.) and were processed for immunohistochemical analysis as previously described in Example 1 above.

Bacteria and Infection Studies. *N. gonorrhoeae* strains 1291, 1291-green, FA1090-green, and MS11-green were used in the infection studies described below. *N. gonorrhoeae* strains 1291-green, FA1090-green, and MS11-green express green fluorescent protein and will be described elsewhere; the plasmid pLES98 was a gift from V. Clark (University of Rochester, Rochester, N.Y.). *N. gonorrhoeae* 1291 and FA1090- and MS11-green parental strains (*N. gonorrhoeae* FA1090 and MS11-A, respectively) are clinically isolated gonococci. *N. gonorrhoeae* FA1090 is a serum-resistant, genital isolate from a patient with disseminated gonococcal infection. *N. gonorrhoeae* 1291 is a serum-sensitive, urethral isolate obtained from a male patient with gonococcal urethritis. *N. gonorrhoeae* 1291, 1291-green, and MS11-green contain the pathogenicity island described by Dillard et al. (1999). For infection studies bacteria were allowed to grow overnight (37° C., 5% $CO_2$) on GC-IsoVitaleX agar plates prior to harvesting with a sterile swab and resuspending in sterile saline. Culture density was determined spectrophotometrically where an optical density of 1 at 600 nm was equivalent to $10^9$ bacteria/ml. Bacterial cultures were further diluted in dk-SFM to a density of $10^7$ bacteria/ml and used to infect cell monolayers at a multiplicity of infection of 100. Infection was allowed to progress for variable time periods after which the infection medium was removed and the cell monolayers were extensively washed with phosphate-buffered saline (PBS) prior to fixation with 2% paraformaldehyde. Uninfected, control cell monolayers were simultaneously processed with challenged cell monolayers. Infected and uninfected (control) cell monolayers were subsequently processed for Laser Scanning Confocal Microscopy (LSCM), Scanning Electron Microscopy (SEM), or Transmission Electron Microscopy (TEM) as described previously in Example 1 above; or the cells were harvested for immunoprecipitation assays.

Immunolabeling and Microscopy. Immunolabeling of frozen tissue sections and cell monolayers was performed as described in Example 1 above. Primary antibodies used for immunolabeling were specific for CD11b (H5A4 (Developmental Studies Hybridoma Bank (DSHB), the University of Iowa, Iowa City, Iowa) and Bear1 (Immunotech, Marseille, France)) or CD18 (anti-CD18 (Santa Cruz Biotechnology, Santa Cruz, Calif.) and IB4, generously provided by E. Brown (University of Calif.)). Tetramethyl rhodamine isothiocyanate (TRITC)- or fluorescein isothiocyanate (FITC)-conjugated secondary antibodies were applied to cell monolayers and bacteria, as noted. Uninfected, tissue cryosections were labeled with FITC-conjugated secondary antibodies and counter stained with ethidium bromide (0.5 ng/ml, 6 min). Clinical biopsy cryosections were incubated with 2C3 and anti-CD18 primary antibodies followed by immunolabeling with TRITC- and FITC-conjugated secondary antibodies, respectively. The 2C3 monoclonal antibody recognizes the H.8 gonococcal surface protein. Infected and uninfected (control) K562 and K562-CR3 cells to be used for TEM analysis were labeled with colloidal-gold secondary antibodies as indicated. Immunolabeled cryosections, cell monolayers, and K562 cells were viewed using the Bio-Rad MRC-1024, the Zeiss 510 Laser Scanning Confocal, or the H-7000 (Hitachi Corp., CA) transmission electron viewing systems. Primary cervical cell and CHO cell monolayers processed for SEM analyses were viewed using the Hitachi S-4000 scanning electron microscope.

Immunoprecipitation and Western Blot Analysis. Immunoprecipitation was performed as described by Wen et al. (2000). Anti-CD18 or H5A4 were used as capture antibodies. Western blotting was subsequently performed using monoclonal antibodies to gonococcal porin (3H1), pili ($IE_8G_8$), or to the opacity associated outer membrane protein, Opa, (4B12), all of which were generously provided by M. Blake (North American Vaccine, Beltsville, Md.). Antibody 6B4, which recognizes the Galβ1-4GlcNAc conserved epitope of gonococcal lipooligosaccharide (LOS), was used to probe for the association of LOS with CR3.

Inhibition of *N. gonorrhoeae* Attachment and Invasion. Primary cervical cell monolayers, CHO-CR3 and -K1 cells, and K562-CR3 and K562 cells were pretreated (30 min, 4° C.) with 20 µg/ml H5A4, Bear1, IB4, or anti-CD18 antibody competitors prior to infection with gonococci as outlined above. Where indicated anti-CD18 blocking peptide (Santa Cruz Biotechnology) was included in the inhibition assay. Infected, control cell assays (devoid of antibody competitors) and uninfected, control cell assays (with anti-CR3 antibodies) were treated in parallel with inhibition assays. The ability of gonococci to bind primary cervical, K562-CR3, or CHO-CR3 cells in the presence or absence of antibody competitors was assessed by LSCM, TEM, or SEM qualitative analysis. Quantitative analysis of the ability of gonococci to invade primary endo- and ectocervical cells and CHO-CR3 and -K1 cells was determined by standard gentimicin-resistance assays as described previously in Example 1 above and in which antibody competitors were included or excluded from the invasion assay as described above. Where indicated primary endo- and ectocervical cell monolayers were pretreated (2 h, 37° C.) with 10 ng/ml *Clostridium* C3 neurotoxin prior to infection. The ability of anti-CR3 antibodies to inhibit gonococcal invasion was determined as a normalized function of the ability of gonococci to invade primary endo- and ectocervical cells and CHO cells in the absence of antibody inhibitors. A Kruskal-Wallis non-parametric analysis of variance was used to determine the statistical significance of invasion assays performed in the presence of the C3 neurotoxin.

Results

Analysis of CR3 Expression in Tissue Biopsies. LSCM of surgical biopsies derived from the ectocervix, endocervix, endometrium, and fallopian tube revealed the presence of both the alpha and beta subunits of CR3. Immunolabeling of tissue sections with anti-CD18 and anti-CD11b (H5A4) antibodies revealed comparable levels of immunofluorescence for each antibody in each of the tissues examined. CR3 expression appeared to be greatest in the ectocervix. Expression levels decreased progressively from the ectocervix to the upper female genital tract with a low level of CR3 expression being observed in the fallopian tube tissue. Immunohistological examination of male urethra and vas deferens tissues failed to reveal the presence of either CR3 subunit. Similarly, tissue derived from the female urethra failed to label positively for CR3. An isotype control antibody yielded no immunofluorescence.

Analysis of CR3 expression in Primary Human Cervical Epithelial Cells. Consistent with results obtained by immunohistochemical examination of endocervical and ectocervical tissue biopsies, primary endo- and ectocervical epithelial cells labeled positive for both CD11b and CD18, and no immunofluorescence was observed with an isotype control. Equivalent fluorescence was observed with either anti-CD18 or H5A4 antibodies. Immunofluorescence paralleled results obtained with immunohistological examination of tissue biopsies in that a lower level of expression was qualitatively observed in endocervical-derived cells in comparison to ectocervical-derived cells. LSCM analysis of infection studies using *N. gonorrhoeae* strains 1291, 1291-green, MS11-green, and FA1090-green suggested that a higher level of CR3 surface expression occurred in the presence of the gonococcus. However, the level of CR3 expression in infected endocervical cells did not obtain that level observed for infected ectocervical cells. Infected ectocervical cells exhibited very high levels of CR3 expression. Co-localization of gonococci with CR3 was observed to occur by thirty minutes post-infection; however, the gonococcus-CR3 association became more prominent by ninety minutes and three hours post-infection.

Analysis of CR3 Expression in Immortalized Epithelial Cells. In contrast to results obtained with primary cervical epithelial cells, cervical and endometrial carcinoma cell lines (ME180 and Hec1B, respectively) failed to demonstrate CR3 expression as determined by LSCM. CR3 could not be identified on E6E7 transfected endo- and ectocervical or male urethral cells by immunofluorescence using anti-CD18 antibody or monoclonal antibody H5A4. Infection of these cell lines with gonococci revealed the presence of minimal amounts of CD18 after ninety minutes and three hours; however, in comparison to results obtained with the primary cervical cells, the level of CR3 expression in the immortalized and carcinoma-derived cells was negligible. CD11b expression was not observed in ME 180, Hec1B, HCK, or End1 cells subsequent to gonococcal infection.

Western Blot Analysis Confirmed the Presence of CR3 in Primary Cervical Cells. To confirm the presence of CR3 in primary cervical epithelial cells immunoprecipitation was performed in which an antibody to CD11b or CD18 was used to capture CR3. Confirmation of CR3 expression was subsequently demonstrated by Western Blot analysis using antibodies to CD18 or CD11b and chemiluminescence. Immunoprecipitation using the monoclonal antibody, H5A4, specific for CD11b and subsequent western blotting with anti-CD18 antibody revealed the presence of an approximately 90 kDa band consistent with CD18. The reverse experiment, in which immunoprecipitation was performed with an anti-CD18 antibody and which the respective western blot was probed with H5A4, demonstrated the presence of an approximately 150 kDa band indicative of CD11b. Parallel immunoprecipitation and Western Blot experiments using male urethral epithelial cells did not reveal the presence of either CR3 subunit. Control immunoprecipitation experiments in which the H5A4 or anti-CD18 capture antibody was omitted, or in which an isotype control was used as the capture antibody, failed to show the 90 or 150 kDa bands with subsequent western blotting.

CR3 Associates with *N. gonorrhoeae* Porin, Pilus, and Opa Proteins. To confirm LSCM analysis of gonococcal co-localization with CR3, immunoprecipitation was performed in which antibodies to CD11b or CD18 were used to capture CR3 on infected and uninfected primary endo- and ectocervical cells. The association of gonococci with CR3 was subsequently examined by Western Blot analysis using antibodies to gonococcal porin, opa, or pili proteins or to LOS. Membranes probed with antibodies to LOS failed to reveal a CR3 association. Western blots probed with the monoclonal antibodies; 3H1, specific for gonococcal porin, $IE_8G_8$, specific for gonococcal pili, or 4B12, which recognizes a conserved epitope of gonococcal Opa proteins, revealed that these proteins associated with CR3 present on primary endo- and ectocervical epithelial cells. Antibody probes to porin, Opa, pili, and LOS did not reveal the presence of these *N. gonorrhoeae*-associated molecules in uninfected endo- and ectocervical cells. Immunoprecipitation (control) experiments in which the antibody to CR3 was omitted also failed to demonstrate the presence of the gonococcal-associated molecules examined.

Anti-CR3 Antibodies Inhibit *N. gonorrhoeae* Binding to Cell Surfaces.

To more closely examine the association of the gonococcus with CR3 TEM and SEM analysis was performed of the ability of *N. gonorrhoeae* to bind CR3-transformed K562 myeloid cells and CHO cells in the presence of antibodies to both the alpha and beta subunits of CR3. TEM analysis demonstrated *N. gonorrhoeae* binding to K562-CR3 cells and inhibition of *N. gonorrhoeae* binding in the presence of the anti-CR3 antibodies H5A4, Bear1, IB4, and anti-CD18. Similar results were obtained with SEM analysis of infected endo- and ectocervical cells and CHO-CR3 cells. Binding of gonococci could be inhibited by the addition of the same anti-CR3 antibodies. Binding inhibition that occurred in the presence of anti-CD18 could be reversed by the addition of the anti-CD18 blocking peptide to the infection assay. Binding of gonococci to CHO-K1 (control) cells, which do not express CR3, was not observed.

*N. gonorrhoeae* Co-localizes with CD18 in vivo. The studies outlined above demonstrate that CR3 serves as a receptor for gonococcal attachment and invasion of the cervical epithelium in vitro. To determine if CR3 is bound by the gonococcus in vivo, LSCM analysis was performed of cervical biopsies derived from women with documented gonorrhea. Immunolabeling of these tissue cryosections demonstrated the presence of CD18 as a green fluorescence and gonococci as a red fluorescence. Gonococci were found to co-localize with CD18, which was visible as a yellow fluorescence. Co-localization was confirmed as a profile plot where the individual fluorescence of each fluorophore (within a designated area of presumed co-localization) was recorded and plotted, individually, by the Zeiss 510 Laser Scanning Confocal viewing system (FIGS. 9A, B). These studies confirm in vitro studies using primary endo- and ectocervical cells and provide evidence that CR3 can serve as a receptor for *N. gonorrhoeae* infection in vivo.

Binding of CR3 Stimulates Membrane Ruffling. Extensive membrane ruffling of *N. gonorrhoeae*-infected K562-CR3, CHO-CR3, and primary cervical cells was observed by TEM, SEM, and LSCM analysis. Ruffles were observed in the presence of gonococci or gonococci in the presence of anti-CR3 antibody, but membrane ruffles were not observed in uninfected cells to which antibody had not been added. Uninfected endocervical, ectocervical, and CHO-CR3 cell monolayers treated with the anti-CR3 antibodies H5A4, Bear1, IB4, and anti-CD18 also revealed extensive membrane ruffling by SEM analysis. Membrane ruffling was most pronounced with the use of the anti-CD18 antibody, IB4. Control assays using CHO-K1 cells failed to reveal the presence of membrane ruffles. These studies suggest that engagement of these cells by anti-CR3 antibodies can initiate membrane ruffling.

*N. gonorrhoeae* Invasion of Primary Endocervical and Ectocervical Cells is Dependent on CR3. Standard gentamicin-resistance assays of infected endo- and ectocervical cells performed in the presence of antibodies to both the alpha and beta subunits of CR3 confirmed results obtained by TEM and SEM analysis of CR3-transfected myeloid and CHO cells. The addition of anti-CD11b and anti-CD18 antibodies to the invasion assays resulted in greater than 93% invasion inhibition of both endo- and ectocervical cells (FIG. 2) with greatest inhibition (99.86% for endocervical cells, 100% for ectocervical cells) being observed with the addition of the anti-CD11b monoclonal antibody, H5A4. Invasion inhibition that occurred in the presence of the anti-CD18 antibody could be reversed by the addition (to the invasion assay) of a blocking peptide to the anti-CD18 antibody. Pretreatment of endo- and ectocervical cells with *Clostridium* C3 neurotoxin, which inactivates the effector domain of the Rho subfamily of GTPases, also significantly inhibited gonococcal invasion supporting a role for CR3-mediated phagocytosis (FIG. 3).

EXAMPLE 3

Identification of Inhibitory Peptides

The present inventors have a phage display library that contains 100 million different copies of 15-mer amino acids. This library is used to screen for phage particles that bind to the CR3 receptor. Briefly, the library is amplified and approximately $10^{12}$ phage are applied to a petri dish contain CHO cells expressing CR3. The phage are allowed to interact with the cells for 1 hour and the dish is washed to remove unbound phage. The bound phage are released with a high pH (9.6-10) buffer, reamplified and the process repeated six more times to enrich for phages particles specific for the CHO-CR3 cells. After the final enrichment, the resulting phage are placed over CHO cells lacking CR3. In this case, the unbound phage (containing CR3 binding peptides) are collected after one hour and amplified, and this process repeated six times.

At that point, enriched CR3 binding phage are plaque purified and tested for the ability to inhibit gonococcal interaction with CHO-CR3 cells. It is estimated that 100 plaque purified phages will be examined to find a phage that inhibits this interaction. When this phage is identified, the 15 mer peptide is sequenced and the peptide synthesized. Gonococcal-CHO-CR3 inhibition studies are then performed with the purified peptide.

EXAMPLE 4

Radiolabeling and Collection of Gonococcal Products Released with Infection of Primary Cervical Cells Gonococci allowed to grow overnight on GC agar were harvested with a sterile swab and used to inoculate 5 ml cultures of Morse's Defined Medium (MDM). MDM was prepared such that half the recommended methionine and cysteine was replaced with 125 µCi Redivue Pro-mix L-[$^{35}$S] in vitro cell labeling mix (Amersham Pharmacia Biotech Inc, Piscataway, N.J.). After approximately 4 h gonococci were collected by centrifugation (4000 rpm, 5 min), rinsed with sterile physiological saline to remove excess label, and resuspended in cold MDM such that a culture density of $10^7$ bacteria ml$^{-1}$ was obtained. MDM containing the $^{35}$S-labeled gonococci was then used to infect approximately $10^5$ primary, human, ecto- and endocervical cells or 35 mm tissue culture dishes devoid of cervical cells. Prior to infection ecto- and endocervical cells were pre-treated (30 min, 37° C.) with 250 mM cycloheximide to inhibit cervical cell protein synthesis. Cycloheximide was maintained in the culture medium through out the course of the infection. Cervical cells and tissue culture plates lacking cervical cells were challenged with gonococci for 90 min and 3 h time periods after which the culture supernatants were collected. Gonococci were removed from the culture supernatants by filtration through low-protein binding 0.22 mm syringe filter units. Supernatant filtrates were concentrated using Centricon YM-3 centrifugal filter units (Millipore Corporation, Bedford, Mass.) prior to suspension in 1M Tris-1% SDS. Concentrated supernatants were separated on a SDS 12% to 4% polyacrylamide gradient gel prior to gel-extraction for mass spectrometry at the Mass Spectrometry Facility located at the University of California (San Francisco, Calif.). Analysis of mass data was performed using Protein Prospector (University of California San Francisco, Calif.) (Clauser et al., 1999) and ProFound (Rockefeller University, New York, N.Y.) (Zhang et al., 2000) database systems for protein identification.

During in vitro infection of primary endocervical and exocervical cells, the inventors have found that there is a 60 to 90 minute delay in the onset of ruffle formation after infection begins. This suggested as one possibility that the gonococcus must be releasing a factor that needed to be at a critical concentration to be effective to induce ruffling. Using bacteria labeled with $^{35}$S cysteine/methionine, the inventors studied the tissue culture supernatant being released by the bacteria (FIG. 10). Using mass spectroscopy and proteomic analysis of a SDS-Gel, the inventors identified a number of the proteins being released by the bacteria. These proteins include the following (see, FIG. 11): gonococcal protein p177, gonococcal protein p88, gonococcal protein p64, gonococcal protein p55, gonococcal protein p46, gonococcal porin, gonococcal pilE, and gonococcal pilC.

Five of these proteins have not been previously described as important in gonococcal pathogenesis (p177, p88, p64, p55, and p46). Homologues of three of the five genes are present in the *Neisseria meningitidis* genomic database. The inventors have confirmed that the genes for two of the proteins (p177 and p55) were present in gonococcal DNA. Protein p177 encodes a 100 amino acid region that has high homology to the filamentous hemagglutinin of *Bordetella pertussis*. This protein is a bridging molecules (can span two structures) that has been shown capable of engaging and activating CR3. Protein p55 has enzymatic activity that involves modification of phospholipid membranes and could be involved in modification of the cell membrane enhancing bacterial entry.

EXAMPLE 5

Inhibition of Cellular Invasion by *Neisseria gonorrhoeae*

Experiments have been performed showing that recombinant murine I-domain from the Alpha-subunit of the complement type 3 receptor inhibits *Neisseria gonorrhoeae* from invading primary human cervical cells.

The recombinant murine I-domain (rI domain) is a 23 kilodalton peptide that contains Myc and His domains. It is recognized by monoclonal antibodies specific for human CR3 I-domain. The amino acid identity to the human I domain is over 90%. The amino acid sequence of the peptide is given below (SEQ ID NO:11).

FPQQESDIVFLIDGSGSINNIDFQKMKEFVSTVMEQFKKSKTLFSLMQYS

DEFRIHFTFNDFKRNPSPRSHVSPIKQLNGRTKTASGIRKVVRELFHKTN

GARENAAKILVVITDGEKFGDPLDYKDVIPEADRAGVIRYVIGVGNAFNK

PQSRRELDTIASKPAGEHVFQVDNFEALNTIQNQLQEKIFAIPAAASFL

The peptide is encoded by the nucleotide sequence given below (SEQ ID NO:12).

```
TTCCCTCAGCAGGAGAGTGACATTCTCTTCTTGATTGATGGCTCCGGTAG
CATCAACAACATTGACTTTCAGAAGATGAAGGAGTTTGTCTCAACTGTGA
TGGAGCAGTTCAAAAAGTCTAAAACCTTGTTCTCTTTGATGCAGTACTCG
GACGAGTTCCGGATTCACTTCACCTTCAATGACTTCAAGAGAAACCCTAG
CCCAAGATCACATGTGAGCCCCATAAAGCAGCTGAATGGAGGACAAAAA
CTGCCTCAGGGATCCGAAAGTAGTGAGAGAACTGTTTCACAAAACCAAT
GGGGCCCGGGAGAATGCTGCCAAGATCCTAGTTGTCATCACAGATGGAGA
AAAATTCGGTGATCCCTTGGATTATAAGGATGTCATCCCCGAGGCAFACA
GAGCAGGGGTCATTCGCTACGTAATTGGGGTGGGAAATGCCTTCAACAAA
CCACAGTCCCGCAGAGAGCTCGACACCATCGCATCTAAGCCAGCTGGTGA
ACACGTGTTCCAAGTGGACAACTTTGAAGCCCTGAATACCATTCAGAACC
AGCTTCAGGAAAAGATCTTTGCAATTCCCGCGGCCGCCAGCTTTCTA
```

Studies were performed evaluating the ability of the rI-domain to inhibit adherence and invasion of primary human ectocervical cells by *Neisseria gonorrhoeae*. The cervical cells were infected with $10^7$ *N. gonorrhoeae* strain 1291. The results of these studies are shown in table 2 below. Recombinant I-domain is a potent inhibitor of ectocervical cell association by *Neisseria gonorrhoeae*. As little as 1 ng of rI-domain gives over 90% inhibition of invasion. With decreasing amounts of rI-domain the inhibition decreases in a dose dependent fashion.

TABLE 2

| rI domain concentration | % inhibition of invasion of primary exocervical cells |
|---|---|
| 1 μg/ml | 98.56 |
| 100 ng/ml | 96.8 |
| 10 ng/ml | 94.6 |
| 1 ng/ml | 92.1 |
| 100 pg/ml | 77.5 |
| 10 pg/ml | 56.3 |
| 1 pg/ml | 17.4 |

Individual, smaller peptides based on the sequence of rI-domain duplicate the inhibitory activity of the rI-domain.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

REFERENCES

Alpuche-Aranda, C. M., E. L. Racoosin, J. A. Swanson, and S. I. Miller. 1994. *Salmonella* stimulate macrophage macropinocytosis and persist within spacious phagosomes. J. Exp. Med. 179:601-608.

Altieri, D. C. 1991. Occupancy of CD11b/CD18 (Mac-1) divalent ion binding site(s) induces leukocyte adhesion. J. Immunol. 147:1891-1898.

Becherer, J. D., J. Alsenz, C. Servis, B. L. Myones, and J. D. Lambris. 1989. Cell surface proteins with activated complement components. Complement Inflamm. 6:142-165.

Bessen, D. and E. C. Gotschlich. 1986. Interactions of gonococci with HeLa cells: attachment, detachment, replication, penetration, and the role of protein II. Infect. Immun. 54(11):154-160.

Bjerknes, R., H.-K. Guttormsen, C. O. Solberg, and L. M. Wetzler. 1995. Neisserial porins inhibit human neutrophil actin polymerization, degranulation, opsonin receptor expression, and phagocytosis but prime the neutrophils to increase their oxidative burst. Infect. Immun. 63:160-167.

Caron, E. and A. Hall. 1998. Identification of two distinct mechanisms of phagocytosis controlled by different Rho GTPases. Science 282:1717-1720.

Chen, T., J. Swanson, J. Wilson, and R. J. Belland. 1995. Heparin protects $Opa^+$ *Neisseria gonorrhoeae* from the batericidal action of normal human serum. Infect. Immun. 63:1790-1795.

Christodoulides, M., J. S. Everson, B. L. Liu, P. R. Lambden, P. J. Watt, E. J. Thomas, and J. E. Heckels. 2000. Interaction of primary human endometrial cells with *Neisseria gonorrhoeae* expressing green fluorescent protein. Mol. Microbiol. 35:32-43.

Clarke, M. and J. A. Spudich. 1977. Non-muscle contractile proteins: the role of actin and myosin in cell motility and shape determination. Ann. Rev. Biochem. 46:797-822.

Clauser, K. R., Baker P. R., and Burlingame A. L. 1999. Role of accurate mass measurement (+/−10 ppm) in protein identification strategies employing MS or MS/MS and database searching. Anal. Chem. 71: 2871-1999.

Clerc, P. and P. J. Sansonetti. 1987. Entry of *Shigella flexneri* into HeLa cells: evidence for directed phagocytosis involving actin polymerization and myosin accumulation. Infect. Immun. 55:2681-2688.

Cooper, N. R. 1991. Complement evasion strategies of microorganisms. Immunol. Today 12:327-331.

Dehio, C., S. D. Gray-Owen, and T. F. Meyer. 1998. The role of neisserial Opa proteins in interactions with host cells. Trends Microbiol. 6:489-495.

Densen, P. 1989. Interaction of complement with *Neisseria meningitidis* and *Neisseria gonorrhoeae*. Cin. Microbiol. Rev. 2:S11-S17.

Densen, P., L. A. MacKeen, and R. A. Clark. 1982. Dissemination of gonococcal infection is associated with delayed stimulation of complement-depenedent neutrophil chemotaxis in vitro. Infect. Immun. 38:563-572.

Dillard, J. 1999. A variable pathogenicity island associated with disseminated gonococcal infection. Midwest Microbial Pathogenesis Group, Sixth Annual Midwest Microbial Pathogenesis Meeting, Milwaukee, Wis.

DiPaolo, J. A., N. C. Popescu, L. Alvarez, and C. D. Woodworth. 1993. Cellular and molecular alterations in human epithelial cells transformed by recombinant human papillomavirus DNA. Crit. Rev. Oncogen. 4:337-360.

Dramsi, S. and P. Cossart. 1998. Intracellular pathogens and the actin cytoskeleton. Ann. Rev. Cell Dev. Biol. 14:137-166.

Draper, D. L., E. A. Donegan, J. F. James, R. L. Sweet, and G. F. Brooks. 1980. Scanning electron microscopy of attachment of *Neisseria gonorrhoeae* colony phenotypes to surfaces of human genital epithelia. Am. J. Obstet. Gynecol. 138:818-826.

Edwards, J. L., J. Q. Shao, K. A. Ault, M. A. Apicella. 2000. *Neisseria gonorrhoeae* elicits membrane ruffling and cytoskeletal rearrangements upon infection of primary human endocervical and ectocervical cells.

Elemer, G. S. and T. S. Edgington. 1994. Microfilament reorganization is associated with functional activation of $\alpha_M\beta_2$ on monocytic cells. J. Biol. Chem. 269:3159-3166.

Erdei, A., G. Füst, and J. Gergely. 1991. The role of C3 in the immune response. Immun. Today 12:332-337.

Evans, B. A. 1977. Ultrastructure study of cervical gonorrhea. J. Infect. Dis. 136(2):248-255.

Finlay, B. B. and S. Falkow. 1997. Common themes in microbial pathogenicity revisited. Microbiol. Mol. Biol. Rev. 61:136-169.

Finlay, B. B. and S. Ruschkowski. 1991. Cytoskeletal rearrangements accompany Salmonella entry into epithelial cells. J. Cell Sci. 99:283-296.

Fluhmann, C. F. 1959. The squamocolumnar transitional zone of the cervix uteri. Obstet. Gynecol. 14:133-148.

Francis, C. L., T. A. Ryan, B. D. Jones, S. J. Smith, and S. Falkow. 1993. Ruffles induced by Salmonella and other stimuli direct macropinocytosis of bacteria. Nature. 364: 639-642.

Frank, M. M. and L. F. Fries. 1991. Complement interactions and functions. Immunol. Today 12:322-326.

Gadzar, A. F., V. Kurvari, A. Virmani, L. Gollahon, M. Sakaguchi, M. Westerfield, D. Kodagoda, V. Stasny, H. T. Cunningham, I. I. Wistuba, G. Tomlinson, V. Tonk, R. Ashfaq, A. M. Leitch, J. D. Minna, and J. W. Shay. 1998. Characterization of paired tumor and non-tumor cell lines established from patients with breast cancer. Int. J. Cancer 78:766-774.

Garcia-del Portiilo, F. and B. B. Finlay. 1994. Salmonella invasion of nonphagocytic cells induces formation of macropinosomes in the host cell. Infect. Immun. 62:4641-4645.

Goeddel et al., Nucleic Acids Res., 8, 4057 (1980).

Grassmé, H. U. C., R. M. Ireland, and J. P. M. van Putten. 1996. Gonococcal opacity protein promotes bacterial entry-associated rearrangements of the epithelial cell actin cytoskeleton. Infect. Immun. 64(5):1621-1630.

Griffin, Jr., F. M., J. A. Griffin, and S. C. Silverstein. 1976. Studies on the mechanisms of phagocytosis II. The interaction of macrophages with anti-immunoglobulin IgG-coated bone marrow-derived lymphocytes. J. Exp. Med. 144:788-809.

Griffin, Jr., F. M., J. A. Griffin, J. E. Leider, and S. C. Silverstein. 1975. Studies on the mechanism of phagocytosis I. Requirements for circumferential attachment of particle-bound ligands to specific receptors on the macrophage plasma membrane. J. Exp. Med. 142:1263-1282.

Handsfield, H. H. 1990. Neisseria gonorrhoeae in Principles and Practice of Infectious Disease 3$^{rd}$ Ed. Mandell, G. L., R. G. Douglas, Jr., and J. E. Bennett (eds) Churchill Livingstone, New York.

Harkness, A. H. 1948. The pathology of gonorrhoea. Br. J. Vener. Dis. 24:137-147.

Harvey, H. A., M. R. Ketterer, A. Preston, D. Lubaroff, R. Williams, and M. A. Apicella. 1997. Ultrastructure analysis of primary human urethral epithelial cell cultures infected with Neisseria gonorrhoeae. Infect. Immun. 65:2420-2427.

Hauck, C. R., T. F. Meyer, F. Lang, and E. Gulbins. 1998. CD66-mediated phagocytosis requires a Src-like tyrosine kinase- and Rac1-dependent signaling pathway. EMBO J. 17:443-454.

Hayashi, T., S. A. Rao, and A. Catanzaro. 1997. Binding of the 68-kilodalton protein of Mycobacterium avium to $\alpha_v\beta_3$ on human monocyte-derived macrophages enhances complement receptor type 3 expression. Infect. Immun. 65:1211-1216.

Hondalus, M. K., M. S. Diamond, L. A. Rosenthal, T. A. Springer, and D. M. Mosser. 1993. The intracellular bacterium Rhodococcus equi requires Mac-1 to bind mammalian cells. Infect. Immun. 61:2919-2929.

Hook, E. W., III and H. H. Handsfield. 1999. Gonococcal infections in the adult in Sexually Transmitted Diseases 3$^{rd}$ Ed. Holmes, K. K., P-A Mårdh, P. F. Sparling, S. M. Lemon, W. E. Stamm, P. Piot, and J. N. Wasserheit (eds). McGraw-Hill, New York.

Hussain, L. A., C. G. Kelly, A. Rodin, M. Jourdan, and T. Lehner. 1995. Investigation of the complement receptor 3 (CD11b/CD18) in human rectal epithelium. Clin. Exp. Imunnol. 102:384-388.

Hynes, R. O. 1987. Integrins: a family of cell surface receptors. Cell 48:549-554.

Iglesias, M., G. D. Plowman, and C. D. Woodworth. 1995. Interleukin-6 and interleukin-6 soluble receptor regulate proliferation of normal, human papillomavirus-immortalized, and carcinoma-derived cervical cells in vitro. Am. J. Pathol. 146:944-952.

Ingalls, R. R., M. Amin Arnaout, R. L. Delude, S. Flaherty, R. Savedra, Jr., and D. T. Golenbock. 1998. The CD11/Cd18 integrins: characterization of three novel LPS signaling receptors. Prog. Clin. Biol. Res. 397:107-117.

Jarvis, G. A., J. Li, and K. V. Swanson. 1999. Invasion of human mucosal epithelial cells by Neisseria gonorrhoeae upregulates expression of intercellular adhesion molecule 1 (ICAM-1). Infect. Immun. 67:1149-1156.

Jerse, A. E. and R. F. Jerse. 1997. Adhesion and invasion by the pathogenic Neisseria. Trends Microbiol. 5:217-221.

Jones, J. L. and R. A. Walker. 1999. Integrins: a role as signaling molecules. 1999. J. Clin. Pathol: Mol. Pathol. 52:208-213.

Jones, S. L., U. G. Knaus, G. M. Bokoch, and E. J. Brown. 1998. Two signaling mechanisms for activation of $\alpha_M\beta_2$ avidity in polymorphonuclear neutrophils. J. Biol. Chem. 273:10556-10566.

Jurianz, K., S. Ziegler, H. Garcia-Schüler, S. Kraus, O. Bohana-Kashtan, Z. Fishelson, and M. Kirschfink. 1999. Complement resistance of tumor cells: basal and induced mechanisms. Mol. Immunol. 36:929-939.

Källström, H., P. Hansson-Palo, and A.-B. Jonsson. 2000. Cholera toxin and extracellular $Ca^{2+}$ induce adherence of non-piliated Nesseria: evidence for an important role of G-proteins and Rho in the bacteria-cell interaction.

Källström, H., M. K. Liszewski, J. P. Atkinson, and A.-B. Jonsson. 1997. Membrane co-factor protein (MCP or CD46) is a cellular pilus receptor for pathogenic Neisseria. Mol. Micobiol. 25:639-647.

Kaur,P. and J. K. McDougall. 1988. Characterization of primary human keratinocytes transformed by human papillomavirus type 18. J. Virol. 62:1917-1924.

Ketterer, M. R., J. Q. Shao, D. B. Homick, B. Buscher, V. K. Bandi, and M. A. Apicella. 1999. Infection of primary human bronchial epithelial cells by Haemophilus influenzae: macropinocytosis as a mechanism of airway epithelial cell entry. Infect. Immun. 67(8):4161-4170.

Kishimoto, T. K., R. S. Larson, A. L. Corbi, M. L. Dustin, D. E. Staunton, and T. A. Springer. 1989. The leukocyte integrins. Adv. Immunol. 46:149-182.

Kondo, T., K. Mihara, Y. Inoue, and M. Namba. 1996. Two-dimensional electrophoretic studies on down-regulated intracellular transferrin in human fibroblasts immortalized by treatment with either 4-nitroquinoline 1-oxide or 60Co gamma rays. Electrophoresis 17:1638-1642.

van Kooyk, Y., S. J. van Vliet, and C. G. Figdor. 1999. The actin cytoskeleton regulates LFA-1 ligand binding through avidity rather than affinity changes. J. Biol. Chem. 274:26869-26877.

Kragsbjerg, P. M. Fogelqvist, and H. Fredlund. 2000. The effects of live Neisseria meningitidis and tumor necrosis factor-α on neutrophil oxidative burst and $β_2$-integrin expression. APMIS 108:276-282.

Lawn et al., Nucleic Acids Res., 9, 6103 (1981).

Lin, J., Z. M. Lei, S. Lojun, Ch. V. Rao, P. G. Satyaswaroop, and T. G. Day. 1994. Increased expression of luteinizing hormone/human chorionic gonadotropin receptor gene in human endometrial carcinomas. J. Clin. Endocrinol. Metab. 79:1483-1491.

Lynch, E. C., M. S. Blake, E. C. Gotschlich, and A. Mauro. 1984. Studies of porins: spontaneously transferred from whole cells and reconstituted from purified proteins of Neisseria gonorrhoeae and Neisseria meningitidis. Biophys. J. 45:104-107.

Maisner, A., G. Zimmer, M. K. Liszewski, D. M. Lublin, J. P. Atkinson, and G. Herrler. 1997. Membrane co-factor protein (CD46) is a basolateral protein that is not endocytosed. J. Biol. Chem. 272:20793-20799.

Maitra, A., I. I. Wistuba, A. K. Virmani, M. Sakaguchi, I. Park, A. Stucky, S. Milchgrub, D. Gibbons, J. D. Minna, and A. F. Gazdar. 1999. Enrichment of epithelial cells for molecular studies. Nature Med. 5:459-463.

McGee, Z. A., D. S. Stephens, L. H. Hoffman, W. F. Schlech III, and R. G. Horn. 1983. Mechanisms of mucosal invasion by pathogenic Neisseria. Rev. Infect. Dis. 5:S708-S714.

McGhee, J. R., et al., "On vaccine development," Sem. Hematol., 30:3-15 (1993).

McNeely, S. G. 1989. Gonococcal infections in women. Sex. Trans. Dis. 16:467-478.

McQuillen, D. P., S. Gulati, S. Ram, A. K. Turner, D. B. Jani, T. C. Heeren, and P. A. Rice. 1999. Complement processing and immunoglobulin binding to Neisseria gonorrhoeae determined in vitro simulates in vivo effects. J. Infect. Dis. 179:124-135.

Mesri, M., J. Plescia, and D. C. Altieri. 1998. Dual regulation of ligand binding by CD11b I domain. J. Biol. Chem. 273:744-748.

Meyer, T. F. 1999. Pathogenic Neisseriae: complexity of pathogen-host cell interplay. Clin. Infect. Dis. 28:433-441.

Moll, R., W. W. Franke, and D. L. Schiller. 1982. The catalog of human cytokeratins: patterns of expression in normal epithelia, tumors and cultured cells. Cell 31:11-24.

Mosser, D. M. and P. J. Edelson. 1987. The third component of complement (C3) is responsible for the intracellular survival of Leishmania major. Nature 327:329-331.

Moulder, J. W. 1985. Comparative biology of intracellular parasitism. Microbiol. Rev. 49:298-337.

Mukherjee, S., R. N. Ghosh, and F. R. Maxfield. 1997. Endocytosis. Physiol. Rev. 77:759-803.

Nassif, X., C. Pujol, P. Morand, and E. Eugéne. 1999. Interactions of pathogenic Neisseria with host cells. Is it possible to assemble the puzzle? Mol. Microbiol. 32:1124-1132.

Nassif, X. and M. So. 1995. Interaction of pathogenic Neisseriae with nonphagocytic cells. Clin. Microbiol. Rev. 8:376-388.

Naumann, M. T. Rudel, and T. F. Meyer. 1999. Host cell interactions and signaling with Neisseria gonorrhoeae. Curr. Opin. Microbiol. 2:62-70.

Obermeier, A., S. Ahmed, E. Manser, S. C. Yen, C. Hall, and L. Lim. 1998. PAK promotes morphological changes by acting upstream of Rac. EMBO J. 17:4328-4339.

Oelschlager, T. A., P. Guerry, and D. J. Kopecko. 1993. Unusual microtubule-dependent endocytosis mechanisms triggered by Campylobacter jejuni and Citrobacter freundii. Proc. Natl. Acad. Sci. 90:6884-6888.

O'Gorman, D. B., M. Costello, J. Weiss, S. M. Firth, and C. D. Scott. 1999. Decreased insulin-like growth factor-II/mannose 6-phosphate receptor expression enhances tumorigenicity in JEG-3 cells. Cancer Res. 59:5692-5694.

de la Paz, H., S. J. Cooke, and J. E. Heckels. 1995. Effect of sialylation of lipopolysaccharide of Neisseria gonorrhoeae on recognition and complement-mediated killing by monoclonal antibodies directed against different outer-membrane antigens. Microbiol. 141:913-920.

Perlmann, H., P. Perlmann, R. D. Schreiber, and H. J. Müller-Eberhard. 1983. C3 receptors on human lymphocyte subsets and recruitment of ADCC effector cells by C3 fragments. J. Immunol. 130:2831-2836.

Price, R. J. and B. Boettcher. 1979. The presence of complement in human cervical mucus and its possible relevance to infertility in women with complement-dependent sperm-immobilizing antibodies. Fertil. Steril. 32:61-66.

Rabinovitch, M. 1995. Professional and non-professional phagocytes: an introduction. Trends Cell Biol. 5:85-88.

Ram, S., F. G. Mackinnon, S. Gulati, D. P. McQuillen, U. Vogel, M. Frosch, C. Elkins, H.-K. Guttormsen, L. M. Wetzler, M. Oppermann, M. K. Pangbum, and P. A. Rice. 1999. The contrasting mechanisms od serum resistance of Neisseria gonorrhoeae and group B Neisseria meningitidis. Mol. Immunol. 36:915-928.

Ram, S., A. K. Sharma, S. D. Simpson, S. Gulati, D. P. McQuillen, M. K. Pangbum, and P. A. Rice. 1998. A novel sialic acid binding site on factor H mediates serum resistance of sialylated Neisseria gonorrhoeae. J. Exp. Med. 187:743-752.

Ramos, O. F., C. Kai, E. Yefenof, and E. Klein. 1988. The elevated natural killer sensitivity of targets carrying surface-attached C3 fragments require the availability of the iC3b receptor (CR3) on the effectors. J. Immunol. 140:1239-1243.

Ramos, O. F., G. Särmay, E. Klein, E. Yefenof, and J. Gergely. 1985. Complement-dependent cellular cytotoxicity: lymphoblastoid lines that activate complement component 3 (C3) and express C3 receptors have increased sensitivity to lymphocyte-mediated lysis in the presence of fresh human serum. Proc. Natl. Acad. Sci. USA 82:5470-5474.

Relman, D., E. Tuomanen, S. Falkow, D. T. Golenbock, K. Saukkonen, and S. D. Wright. 1990. Recognition of a bacterial adhesion by an integrin: macrophage CR3 ($α_Mβ_2$, CD11b/CD18) binds filamentous hemagglutinin of Bordetella pertussis. Cell 61:1375-1382.

Richardson, W. P. and J. C. Sadoff. 1998. Induced engulfinent of Neisseria gonorrhoeae by tissue culture cells. Infect. Immun. 56:2512-2514.

Robinson, M. S. 1994. The role of clathrin, adaptors and dynamin in endocytosis. Curr. Opin. Cell Biol. 6:538-544.

Rosqvist, R., S. Håkansson, Å. Forsberg, and H. Wolf-Watz. 1995. Functional conservaton of the secretion and trans location machinery for the virulence proteins of *Yersiniae, Salmonellae,* and *Shigellae.* EMBO J. 14:4187-4195.

Ross, S. C. and P. Densen. 1985. Opsonophagocytosis of *Neisseria gonorrhoeae*: interaction of local and disseminated isolates with complement and neutrophils. J. Infect. Dis. 151:33-41.

Sandilands, G. P. and K. Whaley. 1985. Receptors for C3b, iC3b, and C3d, p. 140-159, In K. Whaley (Ed.) Methods in Complement for Clinical Immunologists. Butler and Tanner, Ltd. Great Britain.

Schmidt A. and M. N. Hall. 1998. Signaling to the actin cytoskeleton. Annu. Rev. Cell Dev. Biol. 14:305-338.

Sells, M. A., U. G. Knaus, S. Bagrodia, D. M. Ambrose, G. M. Bokoch, and J. Chernoff. 1997. Human p21-activated kinase (PAK1) regulates actin organization in mammalian cells. Curr. Biol. 7:202-210.

Seya, T., T. Hara, M. Matsumoto, and H. Akedo. 1990. Quantitative analysis of membrane cofactor protein (MCP) of complement. High expression of MCP on human leukemia cell lines, which is down-regulated during cell differentiation. J. Immunol. 145:238-245.

Silverstein, S. C., R. M. Steinman, and Z. A. Cohn. 1977. Endocytosis. Ann. Rev. Biochem. 46:669-722.

Sizemore, N. and E. A. Rorke. 1993. Human papillomavirus 16 immortalization of normal ectocervical epithelial cells alters retinoic acid regulation of cell growth and epidermal growth factor receptor expression. Cancer Res. 53:4511-4517.

Skoudy, A., G. Tran Van Nhieu, N. Mantis, M. Arpin, J. Mounier, P. Gounon, and P. Sansonetti. 1999. A functional role for ezrin during *Shigella flexneri* entry into epithelial cells. J. Cell Sci. 112:2059-2068.

Smedts, F., F. Ramaekers, H. Robben, M. Pruszczynski, G. van Muijen, B. Lane, I. Leigh, and P. Vooijs. 1990. Changing patterns of keratin expression during progression of cervical intraepithelial neoplasia. Am. J. Pathol. 136:657-668.

Smedts, F., F. Ramaekers, S. Troyanovsky, M. Pruszczynski, M. Link, B. Lane, I. Leigh, C. Schijf, and P. Vooijs. 1992. Keratin expression in cervical cancer. Am. J. Pathol. 141:497-511.

Stephens, D. S. 1989. Gonococcal and meningococcal pathogenesis as defined by human cell, cell culture, and organ culture assays. Clin. Microbiol. Rev. 2:S104-S111.

Stewart, M. P., C. Cabañas, and N. Hogg. 1996. T cell adhesion to intracellular adhesion molecule-1 (ICAM-1) is controlled by cell spreading and the activation of integrin LFA-1. J. Immunol. 156:1810-1817.

Stocks, S. C., M. A. Kerr, C. Haslett, and I. Dransfield. 1995. CD66-dependent neutrophil activation: a possible mechanism for vascular selectin-mediated regulation of neutrophil adhesion. J. Leuk. Biol. 58:40-48.

Stocks, S. C., M. H. Ruchaud-Sparagano, M. A. Kerr, F. Grunert, C. Haslett, and I. Dransfield. 1996. CD66: role in regulation of neutrophil effector function. Eur. J. Immunol. 2924-2932.

Stryer, L. *Biochemistry* (2d edition) W. H. Freeman and Co. San Francisco (1981), p. 14-15; Lehninger, A. *Biochemistry* (2d ed., 1975), p. 73-75.

Sülz, L., J. P. Valenzuela, A. M. Salvatierra, M. E. Ortiz, and H. B. Croxatto. 1998. The expression of $\alpha_v$ and $\beta_3$ integrin subunits in the normal human fallopian tube epithelium suggests the occurrence of a tubal implantation window. Hum. Reprod. 13:2916-2920.

Sun, Q., K. Tsutsumi, M. Yokoyama, M. M. Pater, and A. Pater. 1993. In vivo cytokeratin-expression pattern of stratified squamous epithelium from human papillomavirus-type-16-immortalized ectocervical and foreskin keratinocytes. Int. J. Cancer 54:656-662.

Swanson, J. A. and S. C. Baer. 1995. Phagocytosis by zippers and triggers. Trends Cell Biol. 5:89-93.

Swanson, J. A. and C. Watts. 1995. Macropinocytosis. Trends Cell Biol. 5:424-428.

Tran Van Mhieu, G. and P. J. Sansonetti. 1999. Mechanisms of *Shigella* entry into epithelial cells. Curr. Opin. Microbiol. 2:51-55.

Vanderpuye, O. A., C. A. Labarrere, and J. A. McIntyre. 1992. The complement system in reproduction. Fertil. Immunol. 27:145-155.

Violette, S. M., J. R. Rusche, S. R. Purdy, J. G. Boyd, J. Cos, and S. Silver. 1995. Differences in the binding of blocking anti-CD11b monoclonal antibodies to the A-domain of CD11b. J. Immunol. 155:3092-3101.

Vogel, U. and M. Frosch. 1999. Mechanisms of neisserial serum resistance. Mol. Microbiol. 32:1133-1139.

Wåhlin, B., H. Perlman, P. Perlman, R. D. Schreiber, and H. J. Müller-Eberhard. 1983. C3 receptors on human lymphocyte subsets and recruitment of ADCC effector cells by C3 fragments. J. Immunol. 130:2831-2836.

Watarai, M., S. Funato, and C. Sasakawa. 1996. Interaction of Ipa proteins of *Shigella flexneri* with $a_5b_1$ integrin promotes entry of the bacteria into mammlian cells. J. Exp. Med. 183:991-999.

Wen, K.-K., P. C. Giardina, M. S. Blake, J. L. Edwards, M. A. Apicella, and P. A. Rubenstein. 2000. Interaction of the gonococcal porin P.IB with G- and F-actin. Biochem. 39:8638-8647.

Wetzler, L. M., K. Barry, M. S. Blake, and E. C. Gotschlich. 1992. Gonococcal lipooligosaccharide sialylation prevents complement-dependent killing by immune sera. Infect. Immun. 60:39-43.

Wright, S. D., P. E. Rao, W. C. Van Voorhis, L. S. Craigmyle, K. Iida, M. A. Talle, E. F. Westberg, G. Goldstein, and S. C. Silverstein. 1983. Icentification of the iC3b receptor of human monocytes and macrophages by using monoclonal antibodies. Proc. Natl. Acad. Sci. USA 80:5699-5703.

Würzner, R. 1999. Evasion of pathogens by avoiding recognition or eradication by complement, in part via molecular mimicry. Mol. Immunol. 36:249-260.

Zhang, W. and B. T. Chait. 2000. Profound-an expert system for protein identification using mass spectrometric peptide mapping information. Anal. Chem. 72:2482-2489.

Zipfel, P. F., J. Hellwage, M. A. Friese, G. Hegasy, S. T. Jokiranta, and S. Meri. 1999. Factor H and disease: a complement regulator affects vital body functions. Mol. Immunol. 36:241-248.

U.S. Pat. No. 4,533,630.

U.S. Pat. No. 4,554,101.

EP 184187A, 2188638A.

What is claimed is:

1. A purified or isolated secreted protein comprising a 55 kD polypeptide from *Neisseria gonorrhoeae*, wherein the molecular weight of the 55 kD polypeptide is determined by electrophoresis of gonococci supernatant filtrate suspended in 1 M Tris-1% SDS in a sodium dodecyl sulfate 12% to 4% polyacrylamide gradient gel under reducing conditions, wherein the protein is involved in modification of cell membrane enhancing bacterial entry.

2. A purified or isolated protein comprising the amino acid sequence of SEQ ID NO:4.

3. The purified or isolated protein of claim 1, wherein the protein is expressed from an isolated nucleic sequence encoding the protein.

4. The purified or isolated protein of claim 1, wherein the protein is conjugated or linked to a second peptide.

5. The purified or isolated protein of claim 1, wherein the polypeptide is conjugated or linked to a polysaccharide.

6. The purified or isolated protein of claim 2, wherein the protein is expressed from an isolated nucleic sequence encoding the protein.

7. The purified or isolated protein of claim 2, wherein the protein is conjugated or linked to a second peptide.

8. The purified or isolated protein of claim 2, wherein the protein is conjugated or linked to a polysaccharide.

9. A composition prepared by combining the purified or isolated protein of claim 1 with a carrier.

10. A composition prepared by combining the purified or isolated protein of claim 2 with a carrier.

11. A composition comprising the purified or isolated protein of claim 1 in combination with a physiologically acceptable, non-toxic vehicle.

12. A composition comprising the purified or isolated protein of claim 2 in combination with a physiologically acceptable, non-toxic vehicle.

13. The composition of claim 12, which further comprises an effective amount of an immunological adjuvant.

14. The composition of claim 11 which further comprises an effective of an immunological adjuvant.

15. A composition comprising the isolated or purified protein of claim 4 combination with a physiologically acceptable, non-toxic vehicle.

16. A composition comprising the isolated or purified protein of claim 7 in combination with a physiologically acceptable, non-toxic vehicle.

17. A composition comprising the isolated or purified protein of claim 5 in combination with a physiologically acceptable, non-toxic vehicle.

18. A composition comprising the isolated or purified protein of claim 8 in combination with a physiologically acceptable, non-toxic vehicle.

* * * * *

SEQUENCE LISTING

<160> NUMBER OF SEQ ID NOS: 12

<210> SEQ ID NO 1
<211> LENGTH: 2015
<212> TYPE: PRT
<213> ORGANISM: Neisseria gonorrhoeae

<400> SEQUENCE: 1

```
Met Asn Lys Gly Leu His Arg Ile Ile Phe Ser Lys Lys His Ser Thr
 1               5                  10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
    50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Asn Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Ser Ile Glu Thr Thr Glu Lys Gly Ala Ala
            340                 345                 350

Gly Thr Phe Ile Ser Asn Gly Gly Arg Ile Glu Ser Lys Gly Leu Leu
```

```
              355                 360                 365
Val Ile Glu Thr Gly Glu Asp Ile Ser Leu Arg Asn Gly Ala Val Val
370                 375                 380

Gln Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
                405                 410                 415

Ala Asn Leu Ser Ala Gly Gly Arg Thr Thr Ile Asn Asp Ala Thr Ile
                420                 425                 430

Gln Ala Gly Ser Ser Val Tyr Ser Ser Thr Lys Gly Asp Thr Glu Leu
                435                 440                 445

Gly Glu Asn Thr Arg Ile Ile Ala Glu Asn Val Thr Val Leu Ser Asn
450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
                485                 490                 495

Asn Ile Arg Leu Asn Asn Gly Asn Ile Lys Gly Gly Lys Gln Leu Ala
                500                 505                 510

Leu Leu Ala Asp Asp Asn Ile Thr Ala Lys Thr Thr Asn Leu Asn Thr
                515                 520                 525

Pro Gly Asn Leu Tyr Val His Thr Gly Lys Asp Leu Asn Leu Asn Val
                530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Leu Leu Asn Val Thr Asn Thr Asn Leu Arg Thr
                580                 585                 590

Asn Ser Gly Asn Leu His Ile Gln Ala Ala Lys Gly Asn Ile Gln Leu
                595                 600                 605

Arg Asn Thr Lys Leu Asn Ala Ala Lys Ala Leu Glu Thr Thr Ala Leu
610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Asn Ala Gly Ser Val Gly Lys Gly
                660                 665                 670

Arg Leu Lys Ala Asp Asn Thr Asn Ile Thr Ser Ser Gly Asp Ile
                675                 680                 685

Thr Leu Val Ala Gly Asn Gly Ile Gln Leu Gly Asp Gly Lys Gln Arg
690                 695                 700

Asn Ser Ile Asn Gly Lys His Ile Ser Ile Lys Asn Gly Gly Asn
705                 710                 715                 720

Ala Asp Leu Lys Asn Leu Asn Val His Ala Lys Ser Gly Ala Leu Asn
                725                 730                 735

Ile His Ser Asp Arg Ala Leu Ser Ile Glu Asn Thr Lys Leu Glu Ser
                740                 745                 750

Thr His Asn Thr His Leu Asn Ala Gln His Glu Arg Val Thr Leu Asn
                755                 760                 765

Gln Val Asp Ala Tyr Ala His Arg His Leu Ser Ile Thr Gly Ser Gln
770                 775                 780
```

-continued

```
Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
                805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
        835                 840                 845

Asp Asn Ala Glu Leu Lys Pro Leu Ala Gly Arg Leu Asn Ile Glu Ala
    850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Ser Ala Lys
                885                 890                 895

Gly Gly Asn Ala Gly Ala Pro Ser Ala Gln Val Ser Ser Leu Glu Ala
                900                 905                 910

Lys Gly Asn Ile Arg Leu Val Thr Gly Glu Thr Asp Leu Arg Gly Ser
        915                 920                 925

Lys Ile Thr Ala Gly Lys Asn Leu Val Val Ala Thr Thr Lys Gly Lys
    930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
                965                 970                 975

Ile Ala Gln Leu Lys Lys Ser Ser Pro Lys Ser Lys Leu Ile Pro Thr
                980                 985                 990

Leu Gln Glu Glu Arg Asp Arg Leu Ala Phe Tyr Ile Gln Ala Ile Asn
        995                 1000                1005

Lys Glu Val Lys Gly Lys Lys Pro Lys Gly Lys Glu Tyr Leu Gln Ala
    1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
                1045                1050                1055

Ala Gly Val Leu Pro Lys Ala Ala Asp Ser Glu Ala Ala Ile Leu
                1060                1065                1070

Ile Asp Gly Ile Thr Asp Gln Tyr Glu Ile Gly Lys Pro Thr Tyr Lys
        1075                1080                1085

Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
            1140                1145                1150

Tyr Thr Phe Leu Lys Thr Lys Gly Lys Ser Gly Lys Ile Ile Arg Lys
        1155                1160                1165

Thr Lys Phe Thr Ser Thr Arg Asp His Leu Ile Met Pro Ala Pro Val
    1170                1175                1180

Glu Leu Thr Ala Asn Gly Ile Thr Leu Gln Ala Gly Gly Asn Ile Glu
1185                1190                1195                1200
```

-continued

```
Ala Asn Thr Thr Arg Phe Asn Ala Pro Ala Gly Lys Val Thr Leu Val
            1205                1210                1215
Ala Gly Glu Glu Leu Gln Leu Leu Ala Glu Glu Gly Ile His Lys His
            1220                1225                1230
Glu Leu Asp Val Gln Lys Ser Arg Arg Phe Ile Gly Ile Lys Val Gly
            1235                1240                1245
Lys Ser Asn Tyr Ser Lys Asn Glu Leu Asn Glu Thr Lys Leu Pro Val
            1250                1255                1260
Arg Val Val Ala Gln Thr Ala Ala Thr Arg Ser Gly Trp Asp Thr Val
1265                1270                1275                1280
Leu Glu Gly Thr Glu Phe Lys Thr Thr Leu Ala Gly Ala Asp Ile Gln
            1285                1290                1295
Ala Gly Val Gly Glu Lys Ala Arg Val Asp Ala Lys Ile Ile Leu Lys
            1300                1305                1310
Gly Ile Val Asn Arg Ile Gln Ser Glu Glu Lys Leu Glu Thr Asn Ser
            1315                1320                1325
Thr Val Trp Gln Lys Gln Ala Gly Arg Gly Ser Thr Ile Glu Thr Leu
            1330                1335                1340
Lys Leu Pro Ser Phe Glu Ser Pro Thr Pro Lys Leu Ser Ala Pro
1345                1350                1355                1360
Gly Gly Tyr Ile Val Asp Ile Pro Lys Gly Asn Leu Lys Thr Glu Ile
            1365                1370                1375
Glu Lys Leu Ser Lys Gln Pro Glu Tyr Ala Tyr Leu Lys Gln Leu Gln
            1380                1385                1390
Val Ala Lys Asn Ile Asn Trp Asn Gln Val Gln Leu Ala Tyr Asp Arg
            1395                1400                1405
Trp Asp Tyr Lys Gln Glu Gly Leu Thr Glu Ala Gly Ala Ala Ile Ile
            1410                1415                1420
Ala Leu Ala Val Thr Val Val Thr Ser Gly Ala Gly Thr Gly Ala Val
1425                1430                1435                1440
Leu Gly Leu Asn Gly Ala Ala Ala Ala Thr Asp Ala Ala Phe Ala
            1445                1450                1455
Ser Leu Ala Ser Gln Ala Ser Val Ser Phe Ile Asn Asn Lys Gly Asp
            1460                1465                1470
Val Gly Lys Thr Leu Lys Glu Leu Gly Arg Ser Ser Thr Val Lys Asn
            1475                1480                1485
Leu Val Val Ala Ala Thr Ala Gly Val Ala Asp Lys Ile Gly Ala
            1490                1495                1500
Ser Ala Leu Asn Asn Val Ser Asp Lys Gln Trp Ile Asn Asn Leu Thr
1505                1510                1515                1520
Val Asn Leu Ala Asn Ala Gly Ser Ala Ala Leu Ile Asn Thr Ala Ile
            1525                1530                1535
Asn Gly Gly Ser Leu Lys Asp Asn Leu Gly Asp Ala Ala Leu Gly Ala
            1540                1545                1550
Ile Val Ser Thr Val His Gly Glu Val Ala Ser Lys Ile Lys Phe Asn
            1555                1560                1565
Leu Ser Glu Asp Tyr Ile Thr His Lys Ile Ala His Ala Ile Ala Gly
            1570                1575                1580
Cys Ala Ala Ala Ala Asn Lys Gly Lys Cys Gln Asp Gly Ala Ile
1585                1590                1595                1600
Gly Ala Ala Val Gly Glu Ile Val Gly Glu Ala Leu Thr Asn Gly Lys
            1605                1610                1615
Asn Pro Ala Thr Leu Thr Ala Lys Glu Arg Glu Gln Ile Leu Ala Tyr
```

-continued

```
                1620                1625                1630
Ser Lys Leu Val Ala Gly Thr Val Ser Gly Val Val Gly Gly Asp Val
            1635                1640                1645

Asn Thr Ala Ala Asn Ala Ala Lys Val Ala Ile Glu Asn Asn Leu Leu
        1650                1655                1660

Ser Gln Glu Glu Tyr Ala Leu Arg Glu Lys Leu Ile Lys Lys Ala Lys
1665                1670                1675                1680

Gly Lys Gly Leu Leu Ser Leu Asp Trp Gly Ser Leu Thr Glu Gln Glu
                1685                1690                1695

Ala Arg Gln Phe Ile Tyr Leu Ile Glu Lys Asp Arg Tyr Ser Asn Gln
            1700                1705                1710

Leu Leu Asp Arg Tyr Gln Lys Asn Pro Ser Ser Leu Asn Asn Gln Glu
        1715                1720                1725

Lys Asn Ile Leu Ala Tyr Phe Ile Asn Gln Thr Ser Gly Gly Asn Thr
    1730                1735                1740

Ala Trp Ala Ala Ser Ile Leu Lys Thr Pro Gln Ser Met Gly Asn Leu
1745                1750                1755                1760

Thr Ile Pro Ser Lys Asp Ile Asn Asn Thr Leu Ser Lys Ala Tyr Gln
                1765                1770                1775

Thr Leu Ser Arg Tyr Asp Ser Phe Asp Tyr Lys Ser Ala Val Ala Ala
            1780                1785                1790

Gln Pro Ala Leu Tyr Leu Leu Asn Gly Pro Leu Gly Phe Ser Val Lys
        1795                1800                1805

Ala Ala Thr Val Ala Ala Gly Gly Tyr Asn Ile Gly Gln Gly Ala Lys
    1810                1815                1820

Ala Ile Ser Asn Gly Glu Tyr Leu His Gly Thr Val Gln Val Val Asn
1825                1830                1835                1840

Gly Thr Leu Met Val Ala Gly Ser Val Ser Ala Gln Ala Ala Ile Ser
                1845                1850                1855

Ala Lys Pro Ala Pro Val Thr Arg Tyr Leu Ser Asn Asp Ser Ala Pro
            1860                1865                1870

Ala Leu Arg Gln Ala Leu Thr Ala Glu Ser Gln Arg Ile Arg Met Lys
        1875                1880                1885

Leu Pro Glu Glu Tyr Arg Gln Ile Gly Asn Leu Ala Ile Ala Lys Ile
    1890                1895                1900

Asp Val Lys Gly Leu Pro Gln Arg Met Glu Ala Phe Ser Ser Phe Gln
1905                1910                1915                1920

Lys Gly Glu His Gly Phe Ile Ser Leu Pro Glu Thr Lys Ile Phe Lys
                1925                1930                1935

Pro Ile Ser Val Asp Lys Tyr His Asn Ile Ala Ser Pro Pro Arg Gly
            1940                1945                1950

Thr Leu Arg Asn Ile Asp Gly Glu Tyr Lys Leu Leu Glu Thr Ile Ala
        1955                1960                1965

Gln Gln Leu Gly Asn Asn Arg Asn Val Ser Gly Arg Ile Asp Leu Phe
    1970                1975                1980

Thr Glu Leu Lys Ala Cys Gln Ser Cys Ser Asn Val Ile Leu Glu Phe
1985                1990                1995                2000

Arg Asn Arg Tyr Pro Asn Ile Gln Leu Asn Ile Phe Thr Gly Lys
                2005                2010                2015

<210> SEQ ID NO 2
<211> LENGTH: 764
<212> TYPE: PRT
<213> ORGANISM: Neisseria gonorrhoeae
```

```
<400> SEQUENCE: 2

Met Arg Arg Glu Ala Lys Met Ala Gln Thr Thr Leu Lys Pro Ile Val
 1               5                  10                  15

Leu Ser Ile Leu Leu Ile Asn Thr Pro Leu Leu Ser Gln Ala His Gly
            20                  25                  30

Thr Glu Gln Ser Val Gly Leu Glu Thr Val Ser Val Val Gly Lys Ser
        35                  40                  45

Arg Pro Arg Ala Thr Ser Gly Leu Leu His Thr Ser Thr Ala Ser Asp
50                  55                  60

Lys Ile Ile Ser Gly Asp Thr Leu Arg Gln Lys Ala Val Asn Leu Gly
65                  70                  75                  80

Asp Ala Leu Asp Gly Val Pro Gly Ile His Ala Ser Gln Tyr Gly Gly
                85                  90                  95

Gly Ala Ser Ala Pro Val Ile Arg Gly Gln Thr Gly Arg Arg Ile Lys
            100                 105                 110

Val Leu Asn His His Gly Glu Thr Gly Asp Met Ala Asp Phe Ser Pro
        115                 120                 125

Asp His Ala Ile Met Val Asp Ser Ala Leu Ser Gln Gln Val Glu Ile
130                 135                 140

Leu Arg Gly Pro Val Thr Leu Leu Tyr Ser Ser Gly Asn Val Ala Gly
145                 150                 155                 160

Leu Val Asp Val Ala Asp Gly Lys Ile Pro Glu Lys Met Pro Glu Asn
                165                 170                 175

Gly Val Ser Gly Glu Leu Gly Leu Arg Leu Ser Ser Gly Asn Leu Glu
            180                 185                 190

Lys Leu Thr Ser Gly Gly Ile Asn Ile Gly Leu Gly Lys Asn Phe Val
        195                 200                 205

Leu His Thr Glu Gly Leu Tyr Arg Lys Ser Gly Asp Tyr Ala Val Pro
210                 215                 220

Arg Tyr Arg Asn Leu Lys Arg Leu Pro Asp Ser His Ala Asp Ser Gln
225                 230                 235                 240

Thr Gly Ser Ile Gly Leu Ser Trp Val Gly Glu Lys Gly Phe Ile Gly
                245                 250                 255

Ala Ala Tyr Ser Asp Arg Arg Asp Gln Tyr Gly Leu Pro Ala His Ser
            260                 265                 270

His Glu Tyr Asp Asp Cys His Ala Asp Ile Ile Trp Gln Lys Ser Leu
        275                 280                 285

Ile Asn Lys Arg Tyr Leu Gln Leu Tyr Pro His Leu Leu Thr Glu Glu
290                 295                 300

Asp Ile Asp Tyr Asp Asn Pro Gly Leu Ser Cys Gly Phe His Asp Asp
305                 310                 315                 320

Asp Asp Ala His Ala His Ala His Asn Gly Lys Pro Trp Ile Asp Leu
                325                 330                 335

Arg Asn Lys Arg Tyr Glu Leu Arg Ala Glu Trp Lys Gln Pro Phe Pro
            340                 345                 350

Gly Phe Glu Ala Leu Arg Val His Leu Asn Arg Asn Asp Tyr Arg His
        355                 360                 365

Asp Glu Lys Ala Gly Asp Ala Val Glu Asn Phe Phe Asn Asn Gln Thr
370                 375                 380

Gln Asn Ala Arg Ile Glu Leu Arg His Gln Pro Ile Gly Arg Leu Lys
385                 390                 395                 400

Gly Ser Trp Gly Val Gln Tyr Leu Gly Gln Lys Ser Ser Ala Leu Ser
```

```
                    405                 410                 415
Ala Thr Ser Glu Ala Val Lys Gln Pro Met Leu Leu Asp Asn Lys Val
            420                 425                 430
Gln His Tyr Ser Phe Phe Gly Val Glu Gln Ala Asn Trp Asp Asn Phe
        435                 440                 445
Thr Leu Glu Gly Gly Val Arg Val Glu Lys Gln Lys Ala Ser Ile Arg
    450                 455                 460
Tyr Asp Lys Ala Leu Ile Asp Arg Glu Asn Tyr Asn His Pro Leu
465                 470                 475                 480
Pro Asp Leu Gly Ala His Arg Gln Thr Ala Arg Ser Phe Ala Leu Ser
            485                 490                 495
Gly Asn Trp Tyr Phe Thr Pro Gln His Lys Leu Ser Leu Thr Ala Ser
        500                 505                 510
His Gln Glu Arg Leu Pro Ser Thr Gln Glu Leu Tyr Ala His Gly Lys
    515                 520                 525
His Val Ala Thr Asn Thr Phe Glu Val Gly Asn Lys His Leu Asn Lys
530                 535                 540
Glu Arg Ser Asn Asn Ile Glu Leu Ala Leu Gly Tyr Glu Gly Asp Arg
545                 550                 555                 560
Trp Gln Tyr Asn Leu Ala Leu Tyr Arg Asn Arg Phe Gly Asn Tyr Ile
            565                 570                 575
Tyr Ala Gln Thr Leu Asn Asp Gly Arg Gly Pro Lys Ser Ile Glu Asp
        580                 585                 590
Asp Ser Glu Met Lys Leu Val Arg Tyr Asn Gln Ser Gly Ala Asp Phe
    595                 600                 605
Tyr Gly Ala Glu Gly Glu Ile Tyr Phe Lys Pro Thr Pro Arg Tyr Arg
610                 615                 620
Ile Gly Val Ser Gly Asp Tyr Val Arg Gly Arg Leu Lys Asn Leu Pro
625                 630                 635                 640
Ser Leu Pro Gly Arg Glu Asp Ala Tyr Gly Asn Arg Pro Leu Ile Ala
            645                 650                 655
Gln Ala Asp Gln Asn Ala Pro Arg Val Pro Ala Ala Arg Leu Gly Val
        660                 665                 670
His Leu Lys Ala Ser Leu Thr Asp Arg Ile Asp Ala Asn Leu Asp Tyr
    675                 680                 685
Tyr Arg Val Phe Ala Gln Asn Lys Leu Ala Arg Tyr Glu Thr Arg Thr
690                 695                 700
Pro Gly His His Met Leu Asn Leu Gly Ala Asn Tyr Arg Arg Asn Thr
705                 710                 715                 720
Arg Tyr Gly Glu Trp Asn Trp Tyr Val Lys Ala Asp Asn Leu Leu Asn
            725                 730                 735
Gln Ser Val Tyr Ala His Ser Ser Phe Leu Ser Asp Thr Pro Gln Met
        740                 745                 750
Gly Arg Ser Phe Thr Gly Gly Val Asn Val Lys Phe
    755                 760

<210> SEQ ID NO 3
<211> LENGTH: 720
<212> TYPE: PRT
<213> ORGANISM: Neisseria gonorrhoeae

<400> SEQUENCE: 3

Met Asn Thr Pro Leu Phe Arg Leu Ser Leu Leu Ser Leu Thr Leu Ala
1               5                   10                  15
```

```
Ala Gly Phe Ala His Ala Ala Glu Asn Asn Ala Lys Val Val Leu Asp
            20                  25                  30

Thr Val Thr Val Lys Gly Asp Arg Gln Gly Ser Lys Ile Arg Thr Asn
        35                  40                  45

Ile Val Thr Leu Gln Gln Lys Asp Glu Ser Thr Ala Thr Asp Met Arg
    50                  55                  60

Glu Leu Lys Glu Glu Pro Ser Ile Asp Phe Gly Gly Asn Gly
65                  70                  75                  80

Thr Ser Gln Phe Leu Thr Leu Arg Gly Met Gly Gln Asn Ser Val Asp
                85                  90                  95

Ile Lys Val Asp Asn Ala Tyr Ser Asp Ser Gln Ile Leu Tyr His Gln
            100                 105                 110

Gly Arg Phe Ile Val Asp Pro Ala Leu Val Lys Val Ser Val Gln
        115                 120                 125

Lys Gly Ala Gly Ser Ala Ser Ala Gly Ile Gly Ala Thr Asn Gly Ala
    130                 135                 140

Ile Ile Ala Lys Thr Val Asp Ala Gln Asp Leu Leu Lys Gly Leu Asp
145                 150                 155                 160

Lys Asn Trp Gly Val Arg Leu Asn Ser Gly Phe Ala Ser Asn Glu Gly
                165                 170                 175

Val Ser Tyr Gly Ala Ser Val Phe Gly Lys Glu Gly Asn Phe Asp Gly
            180                 185                 190

Leu Phe Ser Tyr Asn Arg Asn Asp Glu Lys Asp Tyr Glu Ala Gly Lys
        195                 200                 205

Gly Phe Arg Asn Val Asn Gly Gly Lys Thr Val Pro Tyr Ser Ala Leu
    210                 215                 220

Asp Lys Arg Ser Tyr Leu Ala Lys Ile Gly Thr Thr Phe Gly Asp Asp
225                 230                 235                 240

Asp His Arg Ile Val Leu Ser His Met Lys Asp Gln His Arg Gly Ile
                245                 250                 255

Arg Thr Val Arg Glu Glu Phe Thr Val Gly Asp Lys Ser Ser Arg Ile
            260                 265                 270

Asn Ile Asp Arg Gln Ala Pro Ala Tyr Arg Glu Thr Thr Gln Ser Asn
        275                 280                 285

Thr Asn Leu Ala Tyr Thr Gly Lys Asn Leu Gly Phe Val Glu Lys Leu
    290                 295                 300

Asp Ala Asn Ala Tyr Val Leu Glu Lys Glu Arg Tyr Ser Ala Asp Asp
305                 310                 315                 320

Ser Gly Thr Gly Tyr Ala Gly Asn Val Lys Gly Pro Asn His Thr Arg
                325                 330                 335

Ile Thr Thr Arg Gly Ala Asn Phe Asn Phe Asp Ser Arg Leu Ala Glu
            340                 345                 350

Gln Thr Leu Leu Lys Tyr Gly Ile Asn Tyr Arg His Gln Glu Ile Lys
        355                 360                 365

Pro Gln Ala Phe Leu Asn Ser Lys Phe Ser Ile Pro Thr Thr Glu Glu
    370                 375                 380

Lys Asn Gly Gln Lys Val Asp Lys Pro Met Glu Gln Gln Met Lys Asp
385                 390                 395                 400

Arg Ala Asp Glu Asp Thr Val His Ala Tyr Lys Leu Ser Asn Pro Thr
                405                 410                 415

Lys Thr Asp Thr Gly Val Tyr Val Glu Ala Ile His Asp Ile Gly Asp
            420                 425                 430

Phe Thr Leu Thr Gly Gly Leu Arg Tyr Asp Arg Phe Lys Val Lys Thr
```

-continued

```
                435                 440                 445
His Asp Gly Lys Thr Val Ser Ser Asn Leu Asn Pro Ser Phe Gly
                450                 455                 460

Val Ile Trp Gln Pro His Glu His Trp Ser Phe Ser Ala Ser His Asn
465                 470                 475                 480

Tyr Ala Ser Arg Ser Pro Arg Leu Tyr Asp Ala Leu Gln Thr His Gly
                485                 490                 495

Lys Arg Gly Ile Ile Ser Ile Ala Asp Gly Thr Lys Ala Glu Arg Ala
                500                 505                 510

Arg Asn Thr Glu Ile Gly Phe Asn Tyr Asn Asp Gly Thr Phe Ala Ala
                515                 520                 525

Asn Gly Ser Tyr Phe Trp Gln Thr Ile Lys Asp Ala Leu Ala Asn Pro
                530                 535                 540

Gln Asn Arg His Asp Ser Val Ala Val Arg Glu Ala Val Asn Ala Gly
545                 550                 555                 560

Tyr Ile Lys Asn His Gly Tyr Glu Leu Gly Ala Ser Tyr Arg Thr Gly
                565                 570                 575

Gly Leu Thr Ala Lys Val Gly Val Ser His Ser Lys Pro Arg Phe Tyr
                580                 585                 590

Asp Thr His Lys Asp Lys Leu Leu Ser Ala Asn Pro Glu Phe Gly Ala
                595                 600                 605

Gln Val Gly Arg Thr Trp Thr Ala Ser Leu Ala Tyr Arg Phe Gln Asn
                610                 615                 620

Pro Asn Leu Glu Ile Gly Trp Arg Gly Arg Tyr Val Gln Lys Ala Thr
625                 630                 635                 640

Gly Ser Ile Leu Ala Ala Gly Gln Lys Asp Arg Lys Gly Asn Leu Glu
                645                 650                 655

Asn Val Val Arg Lys Gly Phe Gly Val Asn Asp Val Phe Ala Asn Trp
                660                 665                 670

Lys Pro Leu Gly Lys Asp Thr Leu Asn Val Asn Leu Ser Val Asn Asn
                675                 680                 685

Val Phe Asn Lys Phe Tyr Tyr Pro His Ser Gln Arg Trp Thr Asn Thr
                690                 695                 700

Leu Pro Gly Val Gly Arg Asp Val Arg Leu Gly Val Asn Tyr Lys Phe
705                 710                 715                 720

<210> SEQ ID NO 4
<211> LENGTH: 525
<212> TYPE: PRT
<213> ORGANISM: Neisseria gonorrhoeae

<400> SEQUENCE: 4

Met Arg Ala Asn Pro Lys Thr Gln Ala Met Pro Ser Glu Thr Ile Ser
1               5                   10                  15

Leu Met Lys Thr Arg Ser Leu Ile Ser Leu Cys Leu Leu Cys
                20                  25                  30

Ser Cys Ser Ser Trp Leu Pro Pro Leu Glu Glu Arg Thr Glu Ser Arg
                35                  40                  45

His Phe Asn Thr Ser Lys Pro Val Arg Leu Asp Asn Ile Leu Gln Ile
                50                  55                  60

Arg His Thr Pro His Thr Asn Gly Leu Ser Asp Ile Tyr Leu Leu Asn
65                  70                  75                  80

Asp Pro His Glu Ala Phe Ala Ala Arg Ala Ala Leu Ile Glu Ser Ala
                85                  90                  95
```

```
Glu His Ser Leu Asp Leu Gln Tyr Tyr Ile Trp Arg Asn Asp Ile Ser
            100                 105                 110

Gly Arg Leu Leu Phe Asn Leu Val Tyr Leu Ala Ala Glu Arg Gly Val
            115                 120                 125

Arg Val Arg Leu Leu Asp Asp Asn Thr Arg Gly Leu Asp Asp
        130                 135                 140

Leu Leu Leu Ala Leu Asp Ser His Pro Asn Ile Glu Val Arg Leu Phe
145                 150                 155                 160

Asn Pro Phe Val Leu Arg Lys Trp Arg Ala Leu Gly Tyr Leu Thr Asp
                165                 170                 175

Phe Pro Arg Leu Asn Arg Arg Met His Asn Lys Ser Phe Thr Ala Asp
            180                 185                 190

Asn Arg Ala Thr Ile Leu Gly Gly Arg Asn Ile Gly Asp Glu Tyr Phe
            195                 200                 205

Lys Val Gly Glu Asp Thr Val Phe Ala Asp Leu Asp Ile Leu Ala Thr
        210                 215                 220

Gly Ser Val Val Gly Glu Val Ser His Asp Phe Asp Arg Tyr Trp Ala
225                 230                 235                 240

Ser His Ser Ala His Asn Ala Thr Arg Ile Ile Arg Ser Gly Asn Ile
                245                 250                 255

Gly Lys Gly Leu Gln Ala Leu Gly Tyr Asn Asp Glu Thr Ser Arg His
            260                 265                 270

Ala Leu Leu Arg Tyr Arg Glu Thr Val Glu Gln Ser Pro Leu Tyr Gln
            275                 280                 285

Lys Ile Gln Thr Gly Arg Ile Asp Trp Gln Ser Val Gln Thr Arg Leu
        290                 295                 300

Ile Ser Asp Asp Pro Ala Lys Gly Leu Asp Arg Asp Arg Arg Lys Pro
305                 310                 315                 320

Pro Ile Ala Gly Arg Leu Gln Asp Ala Leu Lys Gln Pro Glu Lys Ser
                325                 330                 335

Val Tyr Leu Val Ser Pro Tyr Phe Val Pro Thr Lys Ser Gly Thr Asp
            340                 345                 350

Ala Leu Ala Lys Leu Val Gln Asp Gly Ile Asp Val Thr Val Leu Thr
            355                 360                 365

Asn Ser Leu Gln Ala Thr Asp Val Ala Ala Val His Ser Gly Tyr Val
        370                 375                 380

Lys Tyr Arg Lys Pro Leu Leu Lys Ala Gly Ile Lys Leu Tyr Glu Leu
385                 390                 395                 400

Gln Pro Asn His Ala Val Pro Ala Thr Lys Asp Lys Gly Leu Thr Gly
                405                 410                 415

Ser Ser Val Thr Ser Leu His Ala Lys Thr Phe Ile Val Asp Gly Lys
            420                 425                 430

Arg Ile Phe Ile Gly Ser Phe Asn Leu Asp Pro Arg Ser Ala Arg Leu
            435                 440                 445

Asn Thr Glu Met Gly Val Val Ile Glu Ser Pro Lys Ile Ala Glu Gln
        450                 455                 460

Met Glu Arg Thr Leu Ala Asp Thr Ser Pro Glu Tyr Ala Tyr Arg Val
465                 470                 475                 480

Thr Leu Asp Arg His Asn Arg Leu Gln Trp His Asp Pro Ala Thr Arg
                485                 490                 495

Lys Thr Tyr Pro Asn Glu Pro Glu Ala Lys Leu Trp Lys Arg Ile Ala
            500                 505                 510

Ala Lys Ile Leu Ser Leu Leu Pro Ile Glu Ser Leu Leu
```

<210> SEQ ID NO 5
<211> LENGTH: 330
<212> TYPE: PRT
<213> ORGANISM: Neisseria gonorrhoeae

<400> SEQUENCE: 5

```
Met Gly Lys Gly Ile Leu Ser Leu Gln Gln Glu Met Ser Leu Glu Tyr
 1               5                  10                  15
Ser Glu Lys Ser Tyr Gln Glu Val Leu Lys Ile Arg Gln Glu Ser Tyr
            20                  25                  30
Trp Lys Arg Met Lys Ser Phe Ser Leu Phe Glu Val Ile Met His Trp
        35                  40                  45
Thr Ala Ser Leu Asn Lys His Thr Cys Arg Ser Tyr Arg Gly Ser Phe
    50                  55                  60
Leu Ser Leu Glu Lys Ile Gly Leu Leu Ser Leu Asp Met Asn Leu Gln
65                  70                  75                  80
Glu Phe Ser Leu Leu Asn His Asn Leu Ile Leu Asp Ala Ile Lys Lys
                85                  90                  95
Val Ser Ser Ala Lys Thr Ser Trp Thr Glu Gly Thr Lys Gln Val Arg
            100                 105                 110
Ala Ala Ser Tyr Ile Ser Leu Thr Arg Phe Leu Asn Arg Met Thr Gln
        115                 120                 125
Gly Ile Val Ala Ile Ala Gln Pro Ser Lys Gln Glu Asn Ser Arg Thr
    130                 135                 140
Phe Phe Lys Thr Arg Glu Ile Val Lys Thr Asp Ala Met Asn Ser Leu
145                 150                 155                 160
Gln Thr Ala Ser Phe Leu Lys Glu Leu Lys Lys Ile Asn Ala Arg Asp
                165                 170                 175
Trp Leu Ile Ala Gln Thr Met Leu Gln Gly Gly Lys Arg Ser Ser Glu
            180                 185                 190
Val Leu Ser Leu Glu Ile Ser Gln Ile Cys Phe Gln Gln Ala Thr Ile
        195                 200                 205
Ser Phe Ser Gln Leu Lys Asn Arg Gln Thr Glu Lys Arg Ile Ile Ile
    210                 215                 220
Thr Tyr Pro Gln Lys Phe Met His Phe Leu Gln Glu Tyr Ile Gly Gln
225                 230                 235                 240
Arg Arg Gly Phe Val Phe Val Thr Arg Ser Gly Lys Met Val Gly Leu
                245                 250                 255
Arg Gln Ile Ala Arg Thr Phe Ser Gln Ala Gly Leu Gln Ala Ala Ile
            260                 265                 270
Pro Phe Lys Ile Thr Pro His Val Leu Arg Ala Thr Ala Val Thr Glu
        275                 280                 285
Tyr Lys Arg Leu Gly Cys Ser Asp Ser Asp Ile Met Lys Val Thr Gly
    290                 295                 300
His Ala Thr Ala Lys Met Ile Phe Ala Tyr Asp Lys Ser Ser Arg Glu
305                 310                 315                 320
Asp Asn Ala Ser Lys Lys Met Ala Leu Ile
                325                 330
```

<210> SEQ ID NO 6
<211> LENGTH: 6048
<212> TYPE: DNA
<213> ORGANISM: Neisseria gonorrhoeae

<400> SEQUENCE: 6

```
atgaataaag gtttacatcg cattatcttt agtaaaaagc acagcaccat ggttgcagta      60
gccgaaactg ccaacagcca gggcaaaggt aaacaggcag gcagttcggt ttctgtttca     120
ctgaaaactt caggcgacct ttgcggcaaa ctcaaaacca cccttaaaac cttggtctgc     180
tctttggttt ccctgagtat ggtattgcct gcccatgccc aaattaccac cgacaaatca     240
gcacctaaaa accagcaggt cgttatcctt aaaaccaaca ctggtgcccc cttggtgaat     300
atccaaactc cgaatggacg cggattgagc cacaaccgct atacgcagtt tgatgttgac     360
aacaaagggg cagtgttaaa caacgaccgt aacaataatc cgtttctggt caaaggcagt     420
gcgcaattga ttttgaacga ggtacgcggt acggctagca aactcaacgg catcgttacc     480
gtaggcggtc aaaaggccga cgtgattatt gccaaccca acggcattac cgttaatggc     540
ggcggcttta aaaatgtcgg tcgggcatc ttaactatcg gtgcgcccca aatcggcaaa     600
gacggtgcac tgacaggatt tgatgtgcgt caaggcacat tgaccgtagg agcagcaggt     660
tggaatgata aaggcggagc cgactacacc ggggtacttg ctcgtgcagt tgctttgcag     720
gggaaattac agggtaaaaa cctggcggtt tctaccggtc ctcagaaagt agattacgcc     780
agcggcgaaa tcagtgcagg tacggcagcg ggtacgaaac cgactattgc ccttgatact     840
gccgcactgg gcgtatgta cgccgacagc atcacactga ttgccaatga aaaaggcgta     900
ggcgtcaaaa atgccggcac actcgaagcg gccaagcaat tgattgtgac ttcgtcaggc     960
cgcattgaaa acagcggccg catcgccacc actgccgacg gcaccgaagc ttcaccgact    1020
tatctctcca tcgaaaccac cgaaaaagga gcggcaggca catttatctc caatggtggt    1080
cggatcgaga gcaaaggctt attggttatt gagacgggag aagatatcag cttgcgtaac    1140
ggagccgtgg tgcagaataa cggcagtcgc ccagctacca cggtattaaa tgctggtcat    1200
aatttggtga ttgagagtaa aactaatgtg aacaatgcca aaggctcggc taatctgtcg    1260
gccggcggtc gtactacgat caatgatgct actattcaag cgggcagttc cgtgtacagc    1320
tccaccaaag cgatactga attgggtgaa atacccgta ttattgctga aaacgtaacc    1380
gtattatcta acggtagtat tggcagtgct gctgtaattg aggctaaaga cactgcacac    1440
attgaatcgg gcaaaccgct ttctttagaa acctcgaccg ttgcctccaa catccgtttg    1500
aacaacggta acattaaagg cggaaagcag cttgctttac tggcagacga taacattact    1560
gccaaaacta ccaatctgaa tactcccggc aatctgtatg ttcatacagg taaagatctg    1620
aatttgaatg ttgataaaga tttgtctgcc gccagcatcc atttgaaatc ggataacgct    1680
gcccatatta ccggcaccag taaaaccctc actgcctcaa aagacatggg tgtggaggca    1740
ggcttgctga atgttaccaa taccaatctg cgtaccaact cgggtaatct gcacattcag    1800
gcagccaaag gcaatattca gcttcgcaat accaagctga acgcagccaa ggctctcgaa    1860
accaccgcat tgcagggcaa tatcgtttca gacggccttc atgctgtttc tgcagacggt    1920
catgtatcct tattggccaa cggtaatgcc gactttaccg gtcacaatac cctgacagcc    1980
aaggccgatg tcaatgcagg atcggttggt aaaggccgtc tgaaagcaga caataccaat    2040
atcacttcat cttcaggaga tattacgttg gttgccggca acggtattca gcttggtgac    2100
ggaaaacaac gcaattcaat caacggaaaa cacatcagca tcaaaacaa cggtggtaat    2160
gccgacttaa aaaaccttaa cgtccatgcc aaaagcgggg cattgaacat tcattccgac    2220
cgggcattga gcatagaaaa taccaagctg gagtctaccc ataatacgca tcttaatgca    2280
caacacgagc gggtaacgct caaccaagta gatgcctacg cacaccgtca tctaagcatt    2340
```

```
accggcagcc agatttggca aaacgacaaa ctgccttctg ccaacaagct ggtggctaac    2400
ggtgtattgg cactcaatgc gcgctattcc caaattgccg acaacaccac gctgagagcg    2460
ggtgcaatca accttactgc cggtaccgcc ctagtcaagc gcggcaacat caattggagt    2520
accgtttcga ccaagacttt ggaagataat gccgaattaa aaccattggc cggacggctg    2580
aatattgaag caggtagcgg cacattaacc atcgaacctg ccaaccgcat cagtgcgcat    2640
accgacctga gcatcaaaac aggcggaaaa ttgctgttgt ctgcaaaagg aggaaatgca    2700
ggtgcgccta gtgctcaagt ttcctcattg gaagcaaaag gcaatatccg tctggttaca    2760
ggagaaacag atttaagagg ttctaaaatt acagccggta aaaacttggt tgtcgccacc    2820
accaaaggca agttgaatat cgaagccgta acaactcat tcagcaatta ttttcctaca     2880
caaaaagcgg ctgaactcaa ccaaaaatcc aaagaattgg aacagcagat tgcgcagttg    2940
aaaaaaagct cgcctaaaag caagctgatt ccaaccctgc aagaagaacg cgaccgtctc    3000
gctttctata ttcaagccat caacaaggaa gttaaggta aaaacccaa aggcaaagaa      3060 tacctgcaag ccaagctttc tgcacaaaat attgacttga tttccgcaca aggcatcgaa    3120
atcagcggtt ccgatattac cgcttccaaa aaactgaacc ttcacgccgc aggcgtattg    3180
ccaaaggcag cagattcaga ggcggctgct attctgattg acggcataac cgaccaatat    3240
gaaattggca agcccaccta caagagtcac tacgacaaag ctgctctgaa caagccttca    3300
cgtttgaccg gacgtacggg ggtaagtatt catgcagctg cggcactcga tgatgcacgt    3360
attattatcg gtgcatccga aatcaaagct ccctcaggca gcatagacat caaagcccat    3420
agtgatattg tactggaggc tggacaaaac gatgcctata ccttcttaaa aaccaaaggt    3480
aaaagcggca aaatcatcag aaaaaccaag tttaccagca cccgcgacca cctgattatg    3540 ccagccccg tcgagctgac cgccaacggt atcacgcttc aggcaggcgg caacatcgaa     3600
gctaatacca cccgcttcaa tgcccctgca ggtaaagtta ccctggttgc gggtgaagag    3660
ctgcaactgc tggcagaaga aggcatccac aagcacgagt tggatgtcca aaaaagccgc    3720
cgctttatcg gcatcaaggt aggtaagagc aattacagta aaaacgaact gaacgaaacc    3780
aaattgcctg tccgcgtcgt cgcccaaact gcagccaccc gttcaggctg ggataccgtg    3840
ctcgaaggta ccgaattcaa aaccacgctg gccggtgccg acattcaggc aggtgtaggc    3900
gaaaaagccc gtgtcgatgc gaaaattatc ctcaaaggca ttgtgaaccg tatccagtcg    3960
gaagaaaaat tagaaaccaa ctcaaccgta tggcagaaac aggccggacg cggcagcact    4020
atcgaaacgc taaaactgcc cagcttcgaa agccctactc cgcccaaatt gtccgcaccc    4080
ggcggctata tcgtcgacat tccgaaaggc aatctgaaaa ccgaaatcga aaagctgtcc    4140
aaacagcccg agtatgccta tctgaaacag ctccaagtag cgaaaaacat caactggaat    4200
caggtgcagc ttgcttacga cagatgggac tacaaacagg agggcttaac cgaagcaggt    4260
gcggcgatta tcgcactggc cgttaccgtg gtcacctcag gcgcaggaac cggagccgta    4320
ttgggattaa acggtgcggc cgccgccgca accgatgcag cattcgcctc tttggccagc    4380
caggcttccg tatcgttcat caacaacaaa ggcgatgtcg gcaaaaccct gaaagagctg    4440
ggcagaagca gcacggtgaa aaatctggtg gttgccgccg ctaccgcagg cgtagccgac    4500
aaaatcggcg cttcggcact gaacaatgtc agcgataagc agtggatcaa caacctgacc    4560
gtcaacctag ccaatgcggg cagtgccgca ctgattaata ccgccatcaa cggcggcagc    4620
ctcaaagaca acttgggcga tgccgcactg ggtgcgatag tcagtaccgt acacgggagaa   4680
```

-continued

```
gtagcgagca aaatcaaatt taatctcagc gaagactaca ttacccacaa gattgcccat    4740
gccatagcgg gctgtgcggc agcggcggcg aataagggta agtgtcagga tggtgcgatc    4800
ggtgcggctg tgggcgagat agtcggggag gctttgacaa acggcaaaaa tcctgccact    4860
ttgacagcta aagaacgcga acagattttg gcatacagca aactggttgc cggtacggta    4920
agcggtgtgg tcggcggcga tgtgaataca gcggcgaatg cggctaaagt cgcgattgaa    4980
aataacctat tatctcaaga gagtatgct cttagagaaa aattgatcaa aaaagccaaa    5040
gggaaaggcc tattatcttt agattggggc agcctgaccg aacaagaggc aaggcagttt    5100
atctatttga ttgagaaaga tcgatattct aatcaattgc ttgaccgata tcaaaaaaat    5160
ccaagtagtt taaataatca agaaaaaaat attcttgcat attttattaa ccaaacctct    5220
ggaggtaaca cagcttgggc agcttcgata ctgaaaacgc cccagtcaat gggtaatctc    5280
actattcctt ccaaagatat taataacacc ttatcgaaag cctatcaaac attgagtcgt    5340
tatgattctt ttgattacaa atcagctgtt gccgcacaac ctgcactttta cttattaaac    5400 ggaccgcttg gcttcagtgt caaagcagct actgtggcag caggaggata taacattgga    5460
cagggagcga aagcaatctc taatggagaa tatctgcatg gtacagttca ggttgttaat    5520
ggcacattga tggttgcagg atctgtatct gcacaggctg caatatcggc caagcctgca    5580
cctgttaccc gttatctgag caatgacagt gctcctgctt taagacaagc tttaactgct    5640
gaaagccaga gaatccgcat gaaactgccg gaagagtatc gacaaatagg gaatcttgcg    5700
atagcaaaaa ttgatgttaa aggattaccg caaaggatgg aagcatttag ttcttttccaa   5760 aaagggggaac atggatttat ttcgttacct gaaacaaaaa ttttttaaacc tatatctgtt    5820 gataaatatc ataatattgc ctctcctcct agaggaacat taagaaatat agatggagaa    5880
tataaattac ttgaaactat agcacagcaa ctcggaaata atcgtaatgt atcaggtaga    5940
attgatctat ttacagaatt aaaggcctgt caatcttgca gcaatgttat tttagagttt    6000
agaaatcgct atccaaatat tcaattaaat attttttacag gaaaatag                 6048
```

<210> SEQ ID NO 7
<211> LENGTH: 2295
<212> TYPE: DNA
<213> ORGANISM: Neisseria gonorrhoeae

<400> SEQUENCE: 7

```
atgcgacgag aagccaaaat ggcacaaact acactcaaac ccattgtttt atcaattctt      60
ttaatcaaca caccctcct ctcccaagcg catggaactg agcaatcagt gggcttggaa       120
acggtcagcg tcgtcggcaa aagccgtccg cgcgccactt cggggctgct gcacacttct     180
accgcctccg acaaaatcat cagcggcgac accttgcgac aaaaagccgt caacttgggt     240
gatgctttag acggcgtacc gggcattcat gcctcgcaat acggcggcgg cgcatccgct    300
cccgttattc gcggtcaaac aggcagacgg attaaagtgt tgaaccatca cggcgaaacg    360
ggcgacatgg cggacttctc tccagaccat gcaatcatgg tggacagcgc cttgtcgcaa    420
caggtcgaaa tcctgcgcgg tccggttacg ctccttgtaca gctcgggcaa tgtggcgggg    480
ctggtcgatg ttgccgatgg caaaatcccc gaaaaaatgc ctgaaaacgg cgtatcgggc    540
gaactcggat tgcgtttgag cagcggcaat ctggaaaaac tcacgtccgg cggcatcaat    600 atcggttttgg gcaaaaactt tgtattgcac acggaagggc tgtaccgcaa atcgggggat    660
tacgccgtac cgcgttaccg caatctgaaa cgcctgcccg acagccacgc cgattcgcaa    720
acgggcagca tcgggctgtc ttgggttggc gaaaaaggct ttatcggcgc agcatacagc    780
```

-continued

```
gaccgtcgcg accaatatgg tctgcctgcc cacagccacg aatacgatga ttgccacgcc      840
gacatcatct ggcaaaagag tttgattaac aaacgctatt tgcagctttta tccgcacctg     900 ttgaccgaag aagacatcga ttacgacaat ccgggcttga gctgcggctt tcacgacgac      960
gatgatgcac acgcccatgc ccacaacggc aaaccttgga tagacctgcg caacaaacgc     1020
tacgaactcc gcgccgaatg gaagcaaccg ttccccggtt ttgaagccct gcgcgtacac     1080
ctgaaccgca acgactaccg ccacgacgaa aaagcaggcg atgcagtaga aaacttttt      1140 aacaaccaaa cgcaaaacgc ccgtatcgag ttgcgccacc aacccatagg ccgtctgaaa     1200
ggcagctggg gcgtgcaata tttgggacaa aaatccagtg ctttatctgc cacatccgaa     1260
gcggtcaaac aaccgatgct gcttgacaat aaagtgcaac attacagctt tttcggtgta     1320
gaacaggcaa actgggacaa cttcacgctt gaaggcggcg tacgcgtgga aaaacaaaaa     1380
gcctccatcc gctacgacaa agcattgatt gatcgggaaa actactacaa ccatcccctg     1440
cccgacctcg gcgcgcaccg ccaaaccgcc cgctcattcg cactttcggg caactggtat     1500
ttcacgccac aacacaaact cagcctgacc gcctcccatc aggaacgcct gccgtcaacg     1560
caagagctgt acgcacacgg caaacacgtc gccaccaaca cctttgaagt cggcaacaaa     1620
cacctcaaca aagagcgttc caacaatatc gaactcgcgc tgggctacga aggcgaccgc     1680
tggcaataca atctggcact ctaccgcaac cgcttcggca actacattta cgcccaaacc     1740
ttaaacgacg gacgcggccc caaatccatc gaagacgaca gcgaaatgaa gctcgtgcgc     1800
tacaaccaat ccggtgcgga cttctacggc gcggaaggcg aaatctactt caaaccgaca     1860
ccgcgctacc gcatcggcgt ttccggcgac tatgtacgag gccgtctgaa aaacctgcct     1920
tccctacccg gcagggaaga cgcctacggc aaccgcccac tcattgccca gccgaccaa     1980 aacgcccctc gcgttccggc tgcgcgcctc ggcgtccacc tgaaagcctc gctgaccgac     2040
cgcatcgatg ccaatttgga ctactaccgc gtgttcgccc aaaacaaact cgcccgctac     2100
gaaacgcgca cgcccggaca ccatatgctc aacctcggcg caaactaccg ccgcaatacg     2160
cgctatggcg agtggaattg gtacgtcaaa gccgacaacc tgctcaacca atccgtttac     2220
gcccacagca gcttcctctc tgatacgccg caaatgggcc gcagctttac cggcggcgtg     2280
aacgtgaagt tttaa                                                       2295
```

<210> SEQ ID NO 8
<211> LENGTH: 2307
<212> TYPE: DNA
<213> ORGANISM: Neisseria gonorrhoeae

<400> SEQUENCE: 8

```
tgttaatata aataaaaata attattaatt attttcttta tcctgccaaa tcttaacggt       60
ttggatttac ttcccttcat actcaagagg acgattgaat gaatacccca ttgttccgtc      120
tcagcctgct ctcgctcaca cttgcggcag gttttgccca cgcggcagaa aataatgcca     180
aggtcgtact ggataccgtt actgtaaaag gcgaccgcca aggcagcaaa atccgtacca     240
acatcgttac gctgcaacaa aaagacgaaa gcaccgcaac cgatatgcgc gaactcttaa     300
aagaagagcc gtccatcgat ttcggcggcg caacggcac gtcccaattc ctgacgctgc     360
gcggcatggg tcagaactct gtcgacatca aggtggacaa cgcctattcc gacagccaaa     420
tcctttacca ccaaggcaga tttattgtcg atcccgcttt ggttaaagtc gttccgtac     480 aaaaaggcgc gggttccgcc tctgccggta tcggcgcgac caacggcgcg atcatcgcca    540
```

```
aaaccgtcga tgcccaagac ctgctcaaag gcttggataa aaactggggc gtgcgcctca      600
acagcggctt tgccagcaac gaaggcgtaa gctacggcgc aagcgtattc ggaaaagagg      660
gcaacttcga cggcttgttc tcttacaacc gcaacgatga aaaagattac gaagccggca      720
aaggtttccg caatgtcaac ggcggcaaaa ccgtaccgta cagcgcgctg acaaacgca       780 gctacctcgc caaaatcgga caaccttcg cgacgacga ccaccgcatc gtgttgagcc        840
acatgaaaga ccaacaccgg ggcatccgca ctgtgcgtga agaatttacc gtcggcgaca      900
aaagttcacg gataaatatt gaccgccaag cccctgctta ccgcgaaact acccaatcca      960
acaccaactt ggcgtacacg ggtaaaaacc tgggctttgt cgaaaaactg gatgccaacg     1020
cctatgtgtt ggaaaagaa cgctattccg ccgatgacag cggcaccggc tacgcaggca      1080
atgtaaaagg ccccaaccat acccgaatca ccactcgtgg tgcgaacttc aacttcgaca     1140
gccgccttgc cgaacaaacc ctgttgaaat acggtatcaa ctaccgccat caggaaatca     1200
aaccgcaagc attttttgaac tcgaaattct ccatcccgac gacagaagag aaaaacggtc    1260
aaaaagtcga taaccgatg gaacaacaaa tgaaagaccg tgcagatgaa gacactgttc      1320
acgcctacaa actttccaac ccgaccaaaa ccgataccgg cgtatatgtt gaagccattc     1380
acgacatcgg cgatttcacg ctgaccggcg ggctgcgtta cgaccgcttc aaggtgaaaa     1440
cccatgacgg caaaaccgtt tcaagcagca accttaaccc gagtttcggt gtgatttggc     1500
agccgcacga acactggagc ttcagcgcga gccacaacta cgccagccgc agcccgcgcc     1560
tgtatgacgc gctgcaaacc cacggtaaac gcggcatcat ctcgattgcc gacggcacaa     1620
aagccgaacg cgcgcgcaat accgaaatcg gcttcaacta caacgacggc acgtttgccg     1680
caaacggcag ctacttctgg cagaccatca agacgcgct tgccaatccg caaaaccgcc     1740
acgactctgt cgccgtccgt gaagccgtca atgccggtta catcaaaaac cacggttacg     1800
aattgggcgc gtcctaccgc accggcggcc tgactgccaa agtcggcgtc agccacagca     1860
aaccgcgctt ttacgatacg cacaaagaca agctgttgag cgcgaatcct gaatttggcg     1920
cacaagtcgg ccgcacttgg acggcctccc ttgcctaccg cttccaaaat ccgaatctgg     1980
aaatcggctg gcgcggccgt tatgttcaaa aagctacggg ttcgatattg gcggcaggtc     2040
aaaaagaccg caaaggcaac ttggaaaacg ttgtacgcaa aggtttcggt gtgaacgatg     2100
tcttcgccaa ctggaaaccg ctgggcaaag acacgctcaa tgtcaatctt tcggttaaca     2160
acgtgttcaa caagttctac tatccgcaca gccaacgctg gaccaatacc ctgccgggcg     2220
tgggacgtga tgtacgcttg ggcgtgaact acaagttcta aaacgcacat cccgaaaaaa     2280
tgccgtctga agcctttca gacggca                                        2307
```

<210> SEQ ID NO 9
<211> LENGTH: 1578
<212> TYPE: DNA
<213> ORGANISM: Neisseria gonorrhoeae

<400> SEQUENCE: 9

```
atgcgcgcca acccccaaaac acaggcaatg ccgtctgaaa ccatatccct gatgaaaaca       60
cgcagcctaa tttcccttttt atgcctcctt ctctgttcat gttcttcatg gttgccccca       120
ctggaagaac ggacggaaag ccgtcatttc aatacttcca aacccgtccg cctggacaac       180
atcctgcaaa tccggcacac ccctcatacc aacgggctat ccgatatcta tctgttgaac       240
gacccccacg aagcctttgc cgcccgcgcc gcccttatcg aatctgccga acacagcctc       300
gatttgcaat actacatctg gcgcaacgac atttccggcc gactgctgtt caacctcgtg       360
```

-continued

```
taccttgccg cagaacgcgg tgtgcgcgta cgcctgctgt tggacgacaa caacacgcgc    420
ggattggacg acctcctgct cgccctcgac agccatccca atatcgaagt gcgcctgttc    480 aacccettcg tcttacgaaa atggcgcgca ctcggctacc tgaccgactt ccccegecte    540 aaccgccgca tgcacaacaa atcctttacc gccgacaacc gcgccaccat actcggcgga    600
cgcaatatcg gcgacgaata cttcaaagtc ggtgaggaca ccgttttcgc cgacctggac    660
atcctcgcca ccggcagcgt cgtcggcgaa gtatcgcacg acttcgaccg ctactgggca    720
agccattccg cccacaacgc cacgcgcatc atccgcagcg gcaacatcgg caagggtctt    780
caagcactcg gatacaacga cgaaacgtcc agacacgcgc tcctgcgcta ccgcgaaacc    840
gtcgaacagt cgcccctcta ccaaaaaata cagacaggac gcatcgactg gcagagcgtc    900
caaacccgcc tcatcagcga cgaccctgca aaaggactcg accgcgaccg ccgcaaaccg    960
ccgattgccg gcggctgca agacgcgctc aaacagcccg aaaaaagcgt ctatctggtt   1020
tcaccctatt tcgtccccac aaaatccggc acagacgcac tggcaaaact ggtgcaggac   1080
ggcatagacg ttaccgtcct gaccaactcg ctacaggcga ccgacgttgc cgccgtccat   1140
tccggctatg tcaaataccg aaaaccgctg ctcaaagccg gcatcaaact ctacgagctg   1200
caacccaacc atgccgtccc tgccacaaaa gacaaaggcc tgaccggcag ctccgtaacc   1260
agcctgcatg ccaaaaacctt cattgtggac ggcaaacgca tcttcatcgg ctcattcaac   1320
ctcgaccccc gttccgcacg gctcaatact gaaatgggcg ttgttatcga aagccccaaa   1380
atcgcagaac agatggagcg cacccttgcc gatacctcac ccgaatacgc ctaccgcgtt   1440
accctcgaca ggcacaaccg cctgcaatgg cacgatcccg ccacccgaaa aacctacccg   1500
aacgaacccg aagccaaact ttggaaacgc atcgccgcaa aatcctatcc cctgctgccc   1560
atagaaagtt tattatag                                                 1578
```

<210> SEQ ID NO 10
<211> LENGTH: 993
<212> TYPE: DNA
<213> ORGANISM: Neisseria gonorrhoeae

<400> SEQUENCE: 10

```
atgggtaaag ggattttatc tttgcagcaa gaaatgtcgt tagaatatag tgaaaagtct     60
tatcaggaag ttttaaaaat tcgccaagaa tcctattgga aacgcatgaa aagcttctcc    120
ttattcgaag ttattatgca ttggaccgca tcactcaaca aacatacttg tagatcatat    180
cgaggatctt ttttgtcttt agaaaagatt ggtctattgt ccttggatat gaatctgcaa    240
gagttttccc ttttaaatca taatctaatc ctagatgcga ttaaaaaagt ttcctctgcc    300
aagacttctt ggaccgaagg tactaaacaa gttcgagcag caagctatat tccttaaca     360 agattcctaa acaggatgac tcaaggaata gtcgctatag cgcaaccttc taaacaagaa    420
aatagtcgaa catttttttaa aaccagggaa atagtaaaaa cggatgcgat gaacagtttg    480
caaacagcat ccttcctaaa agagctaaaa aaaatcaatg cccgggattg gttgatcgcc    540
cagacaatgc tccaaggagg taaacgctcc tctgaagtct taagcttgga gattagtcag    600
atttgtttcc aacaagctac catttctttc tcccagctta agaaccgtca gacagaaaag    660
aggattatta aacttatcc tcagaagttt atgcactttc tacaagagta catcggtcaa    720
cgaagaggtt ttgtcttcgt aactcgctcc ggaaaaatgg tggggttaag gcaaatcgcc    780
cgcacgttct ctcaagcagg actacaagct gcaatccctt ttaaaataac cccgcacgtg    840
```

```
cttcgagcaa ccgctgtgac ggagtacaaa cgcctagggt gctcagactc cgacataatg    900
aaggtcacag gacacgcaac cgcaaagatg atatttgcgt acgataaatc ttctcgagaa    960
gacaacgctt caaagaagat ggctctaata tag                                  993
```

<210> SEQ ID NO 11
<211> LENGTH: 199
<212> TYPE: PRT
<213> ORGANISM: Mus musculus

<400> SEQUENCE: 11

```
Phe Pro Gln Gln Glu Ser Asp Ile Val Phe Leu Ile Asp Gly Ser Gly
 1               5                  10                  15

Ser Ile Asn Asn Ile Asp Phe Gln Lys Met Lys Glu Phe Val Ser Thr
            20                  25                  30

Val Met Glu Gln Phe Lys Lys Ser Lys Thr Leu Phe Ser Leu Met Gln
        35                  40                  45

Tyr Ser Asp Glu Phe Arg Ile His Phe Thr Phe Asn Asp Phe Lys Arg
    50                  55                  60

Asn Pro Ser Pro Arg Ser His Val Ser Pro Ile Lys Gln Leu Asn Gly
65                  70                  75                  80

Arg Thr Lys Thr Ala Ser Gly Ile Arg Lys Val Val Arg Glu Leu Phe
                85                  90                  95

His Lys Thr Asn Gly Ala Arg Glu Asn Ala Ala Lys Ile Leu Val Val
            100                 105                 110

Ile Thr Asp Gly Glu Lys Phe Gly Asp Pro Leu Asp Tyr Lys Asp Val
        115                 120                 125

Ile Pro Glu Ala Asp Arg Ala Gly Val Ile Arg Tyr Val Ile Gly Val
    130                 135                 140

Gly Asn Ala Phe Asn Lys Pro Gln Ser Arg Arg Glu Leu Asp Thr Ile
145                 150                 155                 160

Ala Ser Lys Pro Ala Gly Glu His Val Phe Gln Val Asp Asn Phe Glu
                165                 170                 175

Ala Leu Asn Thr Ile Gln Asn Gln Leu Gln Glu Lys Ile Phe Ala Ile
            180                 185                 190

Pro Ala Ala Ala Ser Phe Leu
        195
```

<210> SEQ ID NO 12
<211> LENGTH: 597
<212> TYPE: DNA
<213> ORGANISM: Mus musculus

<400> SEQUENCE: 12

```
ttccctcagc aggagagtga cattgtcttc ttgattgatg gctccggtag catcaacaac     60
attgactttc agaagatgaa ggagtttgtc tcaactgtga tggagcagtt caaaaagtct    120
aaaaccttgt tctctttgat gcagtactcg gacgagttcc ggattcactt caccttcaat    180
gacttcaaga gaaaccctag cccaagatca catgtgagcc cataaagca gctgaatggg    240 aggacaaaaa ctgcctcagg gatccggaaa gtagtgagag aactgtttca caaaaccaat    300
ggggcccggg agaatgctgc gaagatccta gttgtcatca cagatggaga aaaattcggt    360
gatcccttgg attataagga tgtcatcccc gaggcagaca gagcagggt cattcgctac    420 gtaattgggg tgggaaatgc cttcaacaaa ccacagtccc gcagagagct cgacaccatc    480
```

-continued

```
gcatctaagc cagctggtga acacgtgttc caagtggaca actttgaagc cctgaatacc    540
attcagaacc agcttcagga aaagatcttt gcaattcccg cggccgccag ctttcta       597
```